United States Patent
Nicholls et al.

(10) Patent No.: US 12,297,262 B2
(45) Date of Patent: May 13, 2025

(54) RGMC-SELECTIVE INHIBITORS AND USE THEREOF

(71) Applicant: Scholar Rock, Inc., Cambridge, MA (US)

(72) Inventors: Samantha Nicholls, Arlington, MA (US); Adriana Donovan, West Roxbury, MA (US); Meghan McDonald, London (GB); Abhishek Datta, Boston, MA (US); Allan Capili, Somerville, MA (US); Kevin B. Dagbay, Brighton, MA (US); Lorena Lerner, Newton, MA (US); Leonard Ira Zon, Wellesley, MA (US); Kevin Schutz, Lebanon, NH (US); John Bukowski, Lebanon, NH (US); Justin W. Jackson, Cambridge, MA (US)

(73) Assignee: Scholar Rock, Inc., Cambridge, MA (US)

(*) Notice: Subject to any disclaimer, the term of this patent is extended or adjusted under 35 U.S.C. 154(b) by 1013 days.

(21) Appl. No.: 17/285,952

(22) PCT Filed: Oct. 23, 2019

(86) PCT No.: PCT/US2019/057687
§ 371 (c)(1),
(2) Date: Apr. 16, 2021

(87) PCT Pub. No.: WO2020/086736
PCT Pub. Date: Apr. 30, 2020

(65) Prior Publication Data
US 2021/0380669 A1  Dec. 9, 2021

Related U.S. Application Data

(60) Provisional application No. 62/749,469, filed on Oct. 23, 2018.

(51) Int. Cl.
*C07K 16/18* (2006.01)
*A61P 7/06* (2006.01)

(52) U.S. Cl.
CPC ............ *C07K 16/18* (2013.01); *A61P 7/06* (2018.01); *C07K 2317/33* (2013.01); *C07K 2317/34* (2013.01); *C07K 2317/76* (2013.01); *C07K 2317/92* (2013.01)

(58) Field of Classification Search
CPC .............. C07K 16/18; C07K 2317/33; C07K 2317/34; C07K 2317/76; C07K 2317/92; A61P 7/06
See application file for complete search history.

(56) References Cited

U.S. PATENT DOCUMENTS

| 7,935,344 B2* | 5/2011 | Benson | A61K 9/0019 |
| | | | 424/145.1 |
| 9,376,489 B2* | 6/2016 | Bardroff | G01N 33/6854 |
| 2007/0004618 A1 | 1/2007 | Ganz et al. | |
| 2013/0330359 A1* | 12/2013 | Beligere | C07K 16/22 |
| | | | 536/23.53 |

FOREIGN PATENT DOCUMENTS

WO  2013/090633 A2  6/2013

OTHER PUBLICATIONS

Winkler et al. (Journal of Immunology (2000) 165(8): 4505-4514) (Year: 2000).*
Edwards et al. (Journal of Molecular Biology (2003) 334(1):103-118) (Year: 2003).*
Lloyd et al. (Protein Engineering, Design and Selection (2009) 22(3): 159-168) (Year: 2009).*
Schroeder and Cavacini (Journal of Allergy and Clinical Immunology (2010) 125(2, Suppl.2): S41-S52) (Year: 2010).*
Sela-Culang et al. (Frontiers in Immunology (2013) 4: 302) (Year: 2013).*
Boser et al., Anti-repulsive Guidance Molecule C (RGMc) Antibodies Increases Serum Iron in Rats and Cynomolgus Monkeys by Hepcidin Downregulation. AAPS J. Jul. 2015;17(4):930-8.
Chen et al., A novel validated enzyme-linked immunosorbent assay to quantify soluble hemojuvelin in mouse serum. Haematologica. Feb. 2013;98(2):296-304.
Li et al., Repulsive guidance molecules, novel bone morphogenetic protein co-receptors, are key regulators of the growth and aggressiveness of prostate cancer cells. Int J Oncol. Feb. 2012;40(2):544-50.
Perez De La Lastra et al., Epitope mapping of 10 monoclonal antibodies against the pig analogue of human membrane cofactor protein (MCP). Immunology. Apr. 1999;96(4):663-70.
International Search Report and Written Opinion for Application No. PCT/US2019/057687, dated Feb. 11, 2020, 14 pages.
Bardelli et al., "Epitope mapping by solution NMR spectroscopy," Journal of Molecular Recognition, vol. 28, No. 6, Feb. 27, 2015, pp. 393-400.
Simonyan et al., "Conformational Epitope Mapping by Cross-link Mass Spectrometry: Analysis of Ipilimumab, Nivolumab and Pembrolizumab," Nov. 15, 2017, https://www.amr-inc.co.jp/dcms_media/other/CovalX-PEGSEU17Poster-XLMS_XRC_Comparison.pdf.
Tarantul "The explanatory biotechnological dictionary [in Russian]", Moscow, Languages of Slavic cultures, 2009, p. 821, right column.

* cited by examiner

*Primary Examiner* — Brad Duffy
*Assistant Examiner* — Elizabeth A Shupe
(74) *Attorney, Agent, or Firm* — Finnegan, Henderson Farabow, Garrett & Dunner, LLP

(57) ABSTRACT

Selective inhibitors of repulsive guidance molecule C (RGMc), are described. Related methods, including methods for making, as well as therapeutic use of these inhibitors in the treatment of disorders, such as anemia, are also provided.

35 Claims, 24 Drawing Sheets
Specification includes a Sequence Listing.

FIG. 8B

```
         Region A
RGMC  AEYVSSTLSLRGGGSSGALRGGGGGRGGGGV
RGMA  SEFWSATSGSHAPA----------------SD
RGMB  TDFVSLTSHLNSAV----------------DG
      ::   *                         .

Region B
RGMC  LAFHSAVHGIEDLMIQH
RGMA  LAYHSAVHGIEDLMSQH
RGMB  LVYHSAVLGISDLMSQR
      *.:***** **.***.*:
```

Mapping of SR-RC-AB9 Fab epitope onto the BMP2 binding site Indicates Potential Contact Residues

FIG. 8E

Mapping of SR-RC-AB9 Fab epitope onto the BMP2 binding site Indicates Potential Structural Determinants of RG The CDRs (H1-H3) of the Antibody Can Span the Surface of Regions A and B of the RGMc N-term Domain.

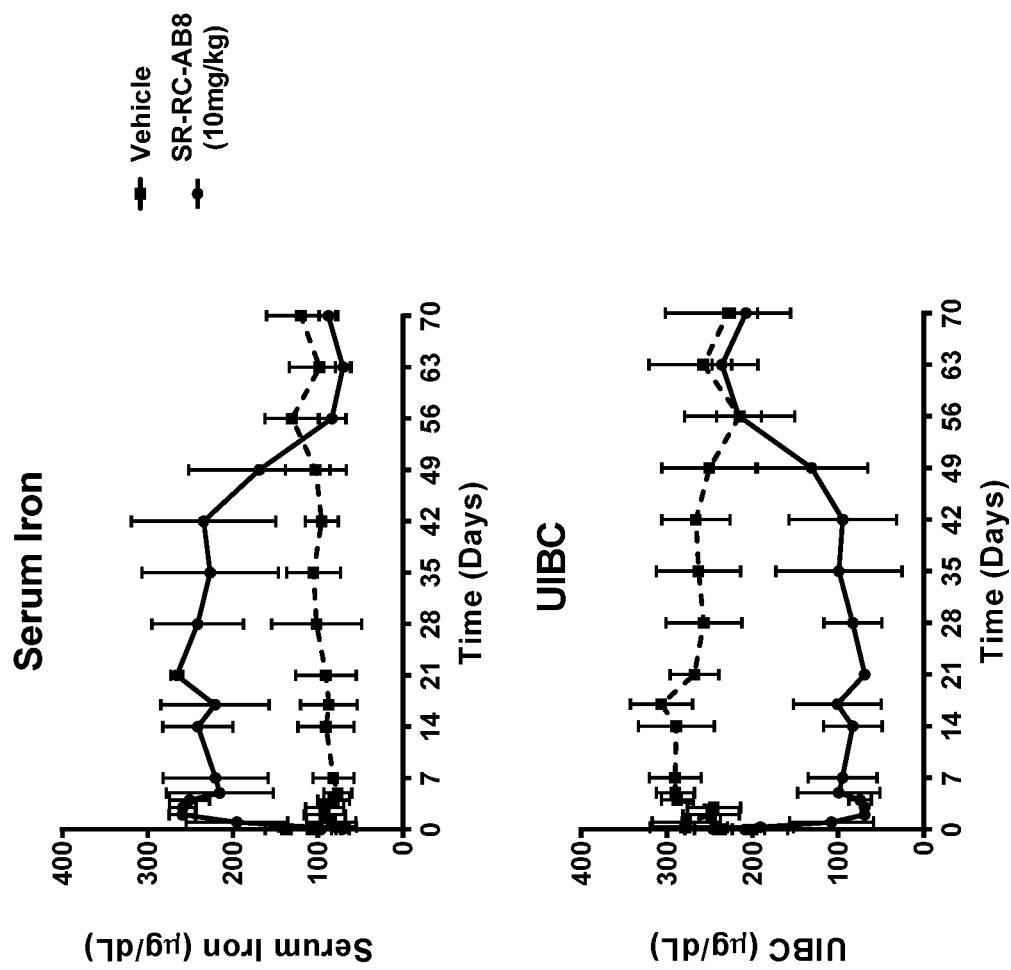

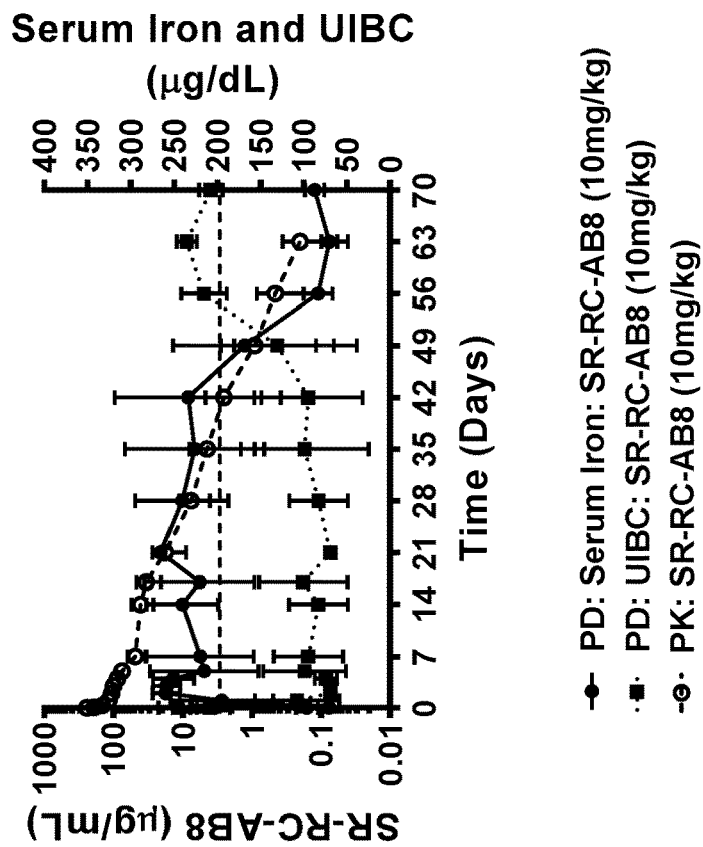
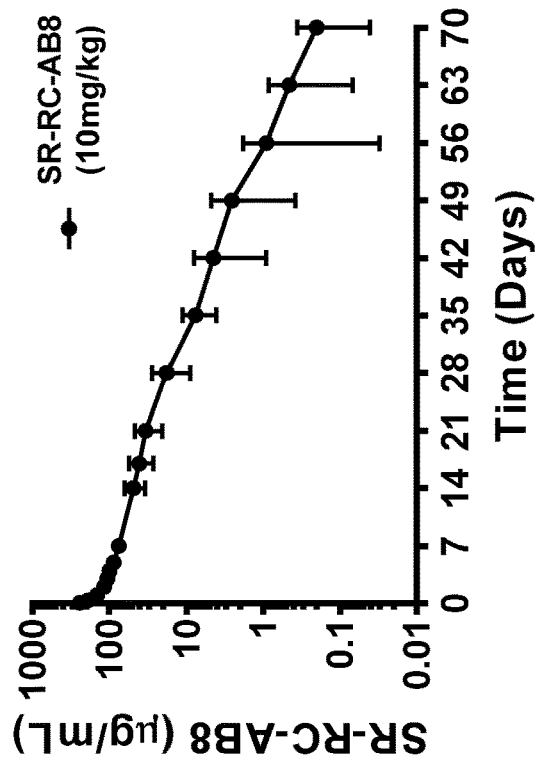

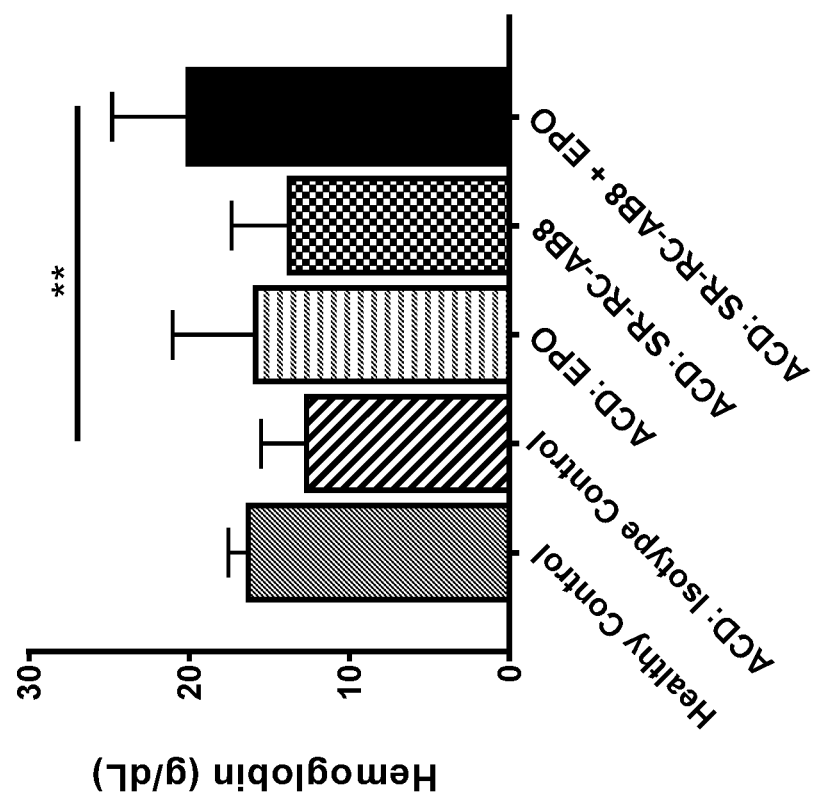

SEQUENCE LISTING

<160> NUMBER OF SEQ ID NOS: 57

<210> SEQ ID NO 1
<211> LENGTH: 426
<212> TYPE: PRT
<213> ORGANISM: Homo sapiens

<400> SEQUENCE: 1

Met Gly Glu Pro Gly Gln Ser Pro Ser Pro Arg Ser Ser His Gly Ser
1               5                   10                  15

Pro Pro Thr Leu Ser Thr Leu Thr Leu Leu Leu Leu Cys Gly His Ala
            20                  25                  30

His Ser Gln Cys Lys Ile Leu Arg Cys Asn Ala Glu Tyr Val Ser Ser
        35                  40                  45

Thr Leu Ser Leu Arg Gly Gly Gly Ser Ser Gly Ala Leu Arg Gly Gly
    50                  55                  60

Gly Gly Gly Gly Arg Gly Gly Gly Val Gly Ser Gly Gly Leu Cys Arg
65                  70                  75                  80

Ala Leu Arg Ser Tyr Ala Leu Cys Thr Arg Arg Thr Ala Arg Thr Cys
                85                  90                  95

Arg Gly Asp Leu Ala Phe His Ser Ala Val His Gly Ile Glu Asp Leu
            100                 105                 110

Met Ile Gln His Asn Cys Ser Arg Gln Gly Pro Thr Ala Pro Pro Pro
        115                 120                 125

Pro Arg Gly Pro Ala Leu Pro Gly Ala Gly Ser Gly Leu Pro Ala Pro
    130                 135                 140

Asp Pro Cys Asp Tyr Glu Gly Arg Phe Ser Arg Leu His Gly Arg Pro
145                 150                 155                 160

Pro Gly Phe Leu His Cys Ala Ser Phe Gly Asp Pro His Val Arg
                165                 170                 175

Ser Phe His His His Phe His Thr Cys Arg Val Gln Gly Ala Trp Pro
            180                 185                 190

Leu Leu Asp Asn Asp Phe Leu Phe Val Gln Ala Thr Ser Ser Pro Met
195                 200                 205

Ala Leu Gly Ala Asn Ala Thr Ala Thr Arg Lys Leu Thr Ile Ile Phe
            210                 215                 220

Lys Asn Met Gln Glu Cys Ile Asp Gln Lys Val Tyr Gln Ala Glu Val
225                 230                 235                 240

Asp Asn Leu Pro Val Ala Phe Glu Asp Gly Ser Ile Asn Gly Gly Asp
            245                 250                 255

Arg Pro Gly Gly Ser Ser Leu Ser Ile Gln Thr Ala Asn Pro Gly Asn
            260                 265                 270

His Val Glu Ile Gln Ala Ala Tyr Ile Gly Thr Thr Ile Ile Ile Arg
            275                 280                 285

Gln Thr Ala Gly Gln Leu Ser Phe Ser Ile Lys Val Ala Glu Asp Val
            290                 295                 300

Ala Met Ala Phe Ser Ala Glu Gln Asp Leu Gln Leu Cys Val Gly Gly
305                 310                 315                 320

Cys Pro Pro Ser Gln Arg Leu Ser Arg Ser Glu Arg Asn Arg Arg Gly
            325                 330                 335

Ala Ile Thr Ile Asp Thr Ala Arg Arg Leu Cys Lys Glu Gly Leu Pro
            340                 345                 350

Val Glu Asp Ala Tyr Phe His Ser Cys Val Phe Asp Val Leu Ile Ser
            355                 360                 365

Gly Asp Pro Asn Phe Thr Val Ala Ala Gln Ala Leu Glu Asp Ala
            370                 375                 380

Arg Ala Phe Leu Pro Asp Leu Glu Lys Leu His Leu Phe Pro Ser Asp
385                 390                 395                 400

Ala Gly Val Pro Leu Ser Ser Ala Thr Leu Leu Ala Pro Leu Leu Ser
            405                 410                 415

Gly Leu Phe Val Leu Trp Leu Cys Ile Gln
            420                 425

<210> SEQ ID NO 2
<211> LENGTH: 313
<212> TYPE: PRT
<213> ORGANISM: Homo sapiens

<400> SEQUENCE: 2

Met Ile Gln His Asn Cys Ser Arg Gln Gly Pro Thr Ala Pro Pro Pro
1                   5                   10                  15

Pro Arg Gly Pro Ala Leu Pro Gly Ala Gly Ser Gly Leu Pro Ala Pro
            20                  25                  30

Asp Pro Cys Asp Tyr Glu Gly Arg Phe Ser Arg Leu His Gly Arg Pro
            35                  40                  45

Pro Gly Phe Leu His Cys Ala Ser Phe Gly Asp Pro His Val Arg Ser
            50                  55                  60

Phe His His His Phe His Thr Cys Arg Val Gln Gly Ala Trp Pro Leu
65                  70                  75                  80

Leu Asp Asn Asp Phe Leu Phe Val Gln Ala Thr Ser Ser Pro Met Ala
                85                  90                  95

Leu Gly Ala Asn Ala Thr Ala Thr Arg Lys Leu Thr Ile Ile Phe Lys
            100                 105                 110

Asn Met Gln Glu Cys Ile Asp Gln Lys Val Tyr Gln Ala Glu Val Asp
            115                 120                 125

```
Asn Leu Pro Val Ala Phe Glu Asp Gly Ser Ile Asn Gly Gly Asp Arg
    130                 135                 140

Pro Gly Gly Ser Ser Leu Ser Ile Gln Thr Ala Asn Pro Gly Asn His
145                 150                 155                 160

Val Glu Ile Gln Ala Ala Tyr Ile Gly Thr Thr Ile Ile Ile Arg Gln
                165                 170                 175

Thr Ala Gly Gln Leu Ser Phe Ser Ile Lys Val Ala Glu Asp Val Ala
            180                 185                 190

Met Ala Phe Ser Ala Glu Gln Asp Leu Gln Leu Cys Val Gly Gly Cys
        195                 200                 205

Pro Pro Ser Gln Arg Leu Ser Arg Ser Glu Arg Asn Arg Arg Gly Ala
    210                 215                 220

Ile Thr Ile Asp Thr Ala Arg Arg Leu Cys Lys Glu Gly Leu Pro Val
225                 230                 235                 240

Glu Asp Ala Tyr Phe His Ser Cys Val Phe Asp Val Leu Ile Ser Gly
                245                 250                 255

Asp Pro Asn Phe Thr Val Ala Ala Gln Ala Ala Leu Glu Asp Ala Arg
            260                 265                 270

Ala Phe Leu Pro Asp Leu Glu Lys Leu His Leu Phe Pro Ser Asp Ala
        275                 280                 285

Gly Val Pro Leu Ser Ser Ala Thr Leu Leu Ala Pro Leu Leu Ser Gly
    290                 295                 300

Leu Phe Val Leu Trp Leu Cys Ile Gln
305                 310

<210> SEQ ID NO 3
<211> LENGTH: 200
<212> TYPE: PRT
<213> ORGANISM: Homo sapiens

<400> SEQUENCE: 3

Met Gln Glu Cys Ile Asp Gln Lys Val Tyr Gln Ala Glu Val Asp Asn
1               5                   10                  15

Leu Pro Val Ala Phe Glu Asp Gly Ser Ile Asn Gly Gly Asp Arg Pro
            20                  25                  30

Gly Gly Ser Ser Leu Ser Ile Gln Thr Ala Asn Pro Gly Asn His Val
        35                  40                  45

Glu Ile Gln Ala Ala Tyr Ile Gly Thr Thr Ile Ile Ile Arg Gln Thr
    50                  55                  60

Ala Gly Gln Leu Ser Phe Ser Ile Lys Val Ala Glu Asp Val Ala Met
65                  70                  75                  80

Ala Phe Ser Ala Glu Gln Asp Leu Gln Leu Cys Val Gly Gly Cys Pro
                85                  90                  95

Pro Ser Gln Arg Leu Ser Arg Ser Glu Arg Asn Arg Arg Gly Ala Ile
            100                 105                 110

Thr Ile Asp Thr Ala Arg Arg Leu Cys Lys Glu Gly Leu Pro Val Glu
        115                 120                 125

Asp Ala Tyr Phe His Ser Cys Val Phe Asp Val Leu Ile Ser Gly Asp
    130                 135                 140

Pro Asn Phe Thr Val Ala Ala Gln Ala Ala Leu Glu Asp Ala Arg Ala
145                 150                 155                 160

Phe Leu Pro Asp Leu Glu Lys Leu His Leu Phe Pro Ser Asp Ala Gly
                165                 170                 175

Val Pro Leu Ser Ser Ala Thr Leu Leu Ala Pro Leu Leu Ser Gly Leu
```

Phe Val Leu Trp Leu Cys Ile Gln
                195                 200

<210> SEQ ID NO 4
<211> LENGTH: 458
<212> TYPE: PRT
<213> ORGANISM: Homo sapiens

<400> SEQUENCE: 4

Met Gly Gly Leu Gly Pro Arg Arg Ala Gly Thr Ser Arg Glu Arg Leu
1               5                   10                  15

Val Val Thr Gly Arg Ala Gly Trp Met Gly Met Gly Arg Gly Ala Gly
            20                  25                  30

Arg Ser Ala Leu Gly Phe Trp Pro Thr Leu Ala Phe Leu Leu Cys Ser
        35                  40                  45

Phe Pro Ala Ala Thr Ser Pro Cys Lys Ile Leu Lys Cys Asn Ser Glu
    50                  55                  60

Phe Trp Ser Ala Thr Ser Gly Ser His Ala Pro Ala Ser Asp Asp Thr
65                  70                  75                  80

Pro Glu Phe Cys Ala Ala Leu Arg Ser Tyr Ala Leu Cys Thr Arg Arg
                85                  90                  95

Thr Ala Arg Thr Cys Arg Gly Asp Leu Ala Tyr His Ser Ala Val His
            100                 105                 110

Gly Ile Glu Asp Leu Met Ser Gln His Asn Cys Ser Lys Asp Gly Pro
        115                 120                 125

Thr Ser Gln Pro Arg Leu Arg Thr Leu Pro Pro Ala Gly Asp Ser Gln
    130                 135                 140

Glu Arg Ser Asp Ser Pro Glu Ile Cys His Tyr Glu Lys Ser Phe His
145                 150                 155                 160

Lys His Ser Ala Thr Pro Asn Tyr Thr His Cys Gly Leu Phe Gly Asp
                165                 170                 175

Pro His Leu Arg Thr Phe Thr Asp Arg Phe Gln Thr Cys Lys Val Gln
            180                 185                 190

Gly Ala Trp Pro Leu Ile Asp Asn Asn Tyr Leu Asn Val Gln Val Thr
        195                 200                 205

Asn Thr Pro Val Leu Pro Gly Ser Ala Ala Thr Ala Thr Ser Lys Leu
    210                 215                 220

Thr Ile Ile Phe Lys Asn Phe Gln Glu Cys Val Asp Gln Lys Val Tyr
225                 230                 235                 240

Gln Ala Glu Met Asp Glu Leu Pro Ala Ala Phe Val Asp Gly Ser Lys
                245                 250                 255

Asn Gly Gly Asp Lys His Gly Ala Asn Ser Leu Lys Ile Thr Glu Lys
            260                 265                 270

Val Ser Gly Gln His Val Glu Ile Gln Ala Lys Tyr Ile Gly Thr Thr
        275                 280                 285

Ile Val Val Arg Gln Val Gly Arg Tyr Leu Thr Phe Ala Val Arg Met
    290                 295                 300

Pro Glu Glu Val Val Asn Ala Val Glu Asp Trp Asp Ser Gln Gly Leu
305                 310                 315                 320

Tyr Leu Cys Leu Arg Gly Cys Pro Leu Asn Gln Gln Ile Asp Phe Gln
                325                 330                 335

Ala Phe His Thr Asn Ala Glu Gly Thr Gly Ala Arg Arg Leu Ala Ala
            340                 345                 350

```
Ala Ser Pro Ala Pro Thr Ala Pro Glu Thr Phe Pro Tyr Glu Thr Ala
            355                 360                 365

Val Ala Lys Cys Lys Glu Lys Leu Pro Val Glu Asp Leu Tyr Tyr Gln
    370                 375                 380

Ala Cys Val Phe Asp Leu Leu Thr Thr Gly Asp Val Asn Phe Thr Leu
385                 390                 395                 400

Ala Ala Tyr Tyr Ala Leu Glu Asp Val Lys Met Leu His Ser Asn Lys
                405                 410                 415

Asp Lys Leu His Leu Tyr Glu Arg Thr Arg Asp Leu Pro Gly Arg Ala
            420                 425                 430

Ala Ala Gly Leu Pro Leu Ala Pro Arg Pro Leu Leu Gly Ala Leu Val
            435                 440                 445

Pro Leu Leu Ala Leu Leu Pro Val Phe Cys
    450                 455

<210> SEQ ID NO 5
<211> LENGTH: 478
<212> TYPE: PRT
<213> ORGANISM: Homo sapiens

<400> SEQUENCE: 5

Met Ile Arg Lys Lys Arg Lys Arg Ser Ala Pro Pro Gly Pro Cys Arg
1               5                   10                  15

Ser His Gly Pro Arg Pro Ala Thr Ala Pro Ala Pro Pro Ser Pro
            20                  25                  30

Glu Pro Thr Arg Pro Ala Trp Thr Gly Met Gly Leu Arg Ala Ala Pro
            35                  40                  45

Ser Ser Ala Ala Ala Ala Ala Glu Val Glu Gln Arg Arg Ser Pro
    50                  55                  60

Gly Leu Cys Pro Pro Leu Glu Leu Leu Leu Leu Leu Phe Ser
65                  70                  75                  80

Leu Gly Leu Leu His Ala Gly Asp Cys Gln Gln Pro Ala Gln Cys Arg
                85                  90                  95

Ile Gln Lys Cys Thr Thr Asp Phe Val Ser Leu Thr Ser His Leu Asn
                100                 105                 110

Ser Ala Val Asp Gly Phe Asp Ser Glu Phe Cys Lys Ala Leu Arg Ala
            115                 120                 125

Tyr Ala Gly Cys Thr Gln Arg Thr Ser Lys Ala Cys Arg Gly Asn Leu
            130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Ser Thr Asn Pro Glu Val Thr
                165                 170                 175

His Asp Pro Cys Asn Tyr His Ser His Ala Gly Ala Arg Glu His Arg
            180                 185                 190

Arg Gly Asp Gln Asn Pro Pro Ser Tyr Leu Phe Cys Gly Leu Phe Gly
            195                 200                 205

Asp Pro His Leu Arg Thr Phe Lys Asp Asn Phe Gln Thr Cys Lys Val
    210                 215                 220

Glu Gly Ala Trp Pro Leu Ile Asp Asn Asn Tyr Leu Ser Val Gln Val
225                 230                 235                 240

Thr Asn Val Pro Val Val Pro Gly Ser Ser Ala Thr Ala Thr Asn Lys
                245                 250                 255

Ile Thr Ile Ile Phe Lys Ala His His Glu Cys Thr Asp Gln Lys Val
                260                 265                 270
```

Tyr Gln Ala Val Thr Asp Asp Leu Pro Ala Ala Phe Val Asp Gly Thr
            275                 280                 285

Thr Ser Gly Gly Asp Ser Asp Ala Lys Ser Leu Arg Ile Val Glu Arg
        290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
                340                 345                 350

Cys Val Asn Gly Cys Pro Leu Ser Glu Arg Ile Asp Asp Gly Gln Gly
            355                 360                 365

Gln Val Ser Ala Ile Leu Gly His Ser Leu Pro Arg Thr Ser Leu Val
        370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala His Ser Ala
                420                 425                 430

Leu Glu Asp Val Glu Ala Leu His Pro Arg Lys Glu Arg Trp His Ile
            435                 440                 445

Phe Pro Ser Ser Gly Asn Gly Thr Pro Arg Gly Gly Ser Asp Leu Ser
        450                 455                 460

Val Ser Leu Gly Leu Thr Cys Leu Ile Leu Ile Val Phe Leu
465                 470                 475

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Thr Phe Ser Ser Tyr Ser Ile Ser
1               5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gly Ile Ile Pro Ile Phe Gly Val Ala Ser Tyr Ala Gln Lys Phe Gln
1               5                   10                  15

Gly

<210> SEQ ID NO 8
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 8

Ala Arg Gly Ala Ile Ala Ala Thr Tyr Gly Leu Gly Met Asp Val
1               5                   10                  15

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 9

Gln Ala Ser Gln Asp Ile Ser Asn Tyr Leu Asn
1               5                   10

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 10

Asp Ala Ser Asn Leu Glu Thr
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic peptide"

<400> SEQUENCE: 11

Gln Gln Leu Val Asp Leu Pro Pro Thr
1               5

<210> SEQ ID NO 12
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 12

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ser Ile Ser Trp Val Arg Gln Ala Pro Gly Gln Gly Leu Glu Trp Met
        35                  40                  45

Gly Gly Ile Ile Pro Ile Phe Gly Val Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Ala Ala Thr Tyr Gly Leu Gly Met Asp Val Trp
            100                 105                 110

Gly Gln Gly Thr Thr Val Thr Val Ser Ser
        115                 120

<210> SEQ ID NO 13
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Val Asp Leu Pro Pro
                85                  90                  95

Thr Phe Gly Gly Gly Thr Lys Val Glu Ile Lys
            100                 105

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gly Thr Phe Ser Ser Tyr Ala Ile Ser
1               5

<210> SEQ ID NO 15
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ile Ile Pro Ile Phe Gly Thr Ala Asn Tyr Ala Gln Lys Phe Gln
1               5                   10                  15

Gly

<210> SEQ ID NO 16
<211> LENGTH: 15
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ala Arg Gly Ala Ile Ala Ala Thr Tyr Gly Leu Gly Met Asp Val
1               5                   10                  15

<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gln Ala Ser Gln Asp Ile Ser Asn Tyr Leu Asn
1               5                   10

<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Ala Ser Asn Leu Glu Thr
1               5

<210> SEQ ID NO 19
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Gln Gln Leu Val Asp Leu Pro Pro Thr
1               5

<210> SEQ ID NO 20
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Ala Ile Ala Ala Thr Tyr Gly Leu Gly Met Asp Val Trp
            100                 105                 110

Gly Gln Gly Thr Thr Val Thr Val Ser Ser
        115                 120

<210> SEQ ID NO 21
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Val Asp Leu Pro Pro
            85                  90                  95

Thr Phe Gly Gly Gly Thr Lys Val Glu Ile Lys
            100                 105

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Thr Phe Ser Ser Tyr Ala Ile Gln
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Ile Ile Pro Ile Phe Gly Val Ala Ser Tyr Ala Gln Lys Phe Gln
1               5                   10                  15

Gly

```
<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ala Arg Gly Ala Ile Val Ala Thr Tyr Gly Leu Gly Met Asp Val
1               5                   10                  15

<210> SEQ ID NO 25
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gln Ala Ser Gln Asp Ile Ser Asn Tyr Leu Asn
1               5                   10

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Ala Ser Asn Leu Glu Thr
1               5

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gln Gln Leu Val Asp Leu Pro Pro Thr
1               5

<210> SEQ ID NO 28
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Gln Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Ser Tyr
            20                  25                  30

Ala Ile Gln Trp Val Arg Gln Ala Pro Gly Gln Gly Leu Glu Trp Met
        35                  40                  45
```

```
Gly Ile Ile Pro Ile Phe Gly Val Ala Ser Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Val Ala Thr Tyr Gly Leu Gly Met Asp Val Trp
                100                 105                 110

Gly Gln Gly Thr Thr Val Thr Val Ser Ser
            115                 120
```

<210> SEQ ID NO 29
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Val Asp Leu Pro Pro
                85                  90                  95

Thr Phe Gly Gly Gly Thr Lys Val Glu Ile Lys
                100                 105
```

<210> SEQ ID NO 30
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 30

```
Gly Thr Phe Arg Ser Tyr Ser Ile Ser
1               5
```

<210> SEQ ID NO 31
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 31

```
Gly Ile Ile Pro Ile Phe Gly Val Ala Asn Tyr Ala Gln Lys Phe Gln
1               5                   10                  15
```

Gly

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ala Arg Gly Ala Tyr Glu Ala Thr Tyr Gly Leu Gly Met Asp Val
1               5                   10                  15

<210> SEQ ID NO 33
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gln Ala Ser Gln Asp Ile Ser Asn Tyr Leu Asn
1               5                   10

<210> SEQ ID NO 34
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Asp Ala Ser Asn Leu Glu Thr
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gln Gln Leu Val Asp Leu Pro Pro Thr
1               5

<210> SEQ ID NO 36
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Tyr
            20                  25                  30

```
Ser Ile Ser Trp Val Arg Gln Ala Pro Gly Gln Gly Leu Glu Trp Met
            35                  40                  45

Gly Gly Ile Ile Pro Ile Phe Gly Val Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Glu Ala Thr Tyr Gly Leu Gly Met Asp Val Trp
                100                 105                 110

Gly Gln Gly Thr Thr Val Thr Val Ser Ser
            115                 120
```

<210> SEQ ID NO 37
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Val Asp Leu Pro Pro
                85                  90                  95

Thr Phe Gly Gly Gly Thr Lys Val Glu Ile Lys
                100                 105
```

<210> SEQ ID NO 38
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

```
Gly Thr Phe Ser Ser Tyr Ser Ile Gln
1               5
```

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

```
Gly Ile Ile Pro Ile Phe Gly Val Ala Ser Tyr Ala Gln Lys Phe Gln
1               5                   10                  15

Gly

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ala Arg Gly Ala Ile Ala Ala Thr Tyr Gly Leu Gly Met Asp Val
1               5                   10                  15

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gln Ala Ser Gln Asp Ile Ser Asn Tyr Leu Asn
1               5                   10

<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asp Ala Ser Asn Leu Glu Thr
1               5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gln Gln Leu Val Asp Leu Pro Pro Thr
1               5

<210> SEQ ID NO 44
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
            20                  25                  30

Ser Ile Gln Trp Val Arg Gln Ala Pro Gly Gln Gly Leu Glu Trp Met
        35                  40                  45

Gly Gly Ile Ile Pro Ile Phe Gly Val Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ile Ala Ala Thr Tyr Gly Leu Gly Met Asp Val Trp
            100                 105                 110

Gly Gln Gly Thr Thr Val Thr Val Ser Ser
        115                 120

<210> SEQ ID NO 45
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Val Asp Leu Pro Pro
                85                  90                  95

Thr Phe Gly Gly Gly Thr Lys Val Glu Ile Lys
            100                 105

<210> SEQ ID NO 46
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Tyr Val Ser Ser Thr Leu Ser Leu
1               5

<210> SEQ ID NO 47
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 47

Phe His Ser Ala Val His Gly Ile Glu Asp Leu
1               5                   10

<210> SEQ ID NO 48
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Cys Pro Pro Cys Pro
1               5

<210> SEQ ID NO 49
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Asp Pro His
1

<210> SEQ ID NO 50
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Phe Gly Asp Pro His
1               5

<210> SEQ ID NO 51
<211> LENGTH: 31
<212> TYPE: PRT
<213> ORGANISM: Homo sapiens

<400> SEQUENCE: 51

Ala Glu Tyr Val Ser Ser Thr Leu Ser Leu Arg Gly Gly Ser Ser
1               5                   10                  15

Gly Ala Leu Arg Gly Gly Gly Gly Gly Arg Gly Gly Gly Val
            20                  25                  30

<210> SEQ ID NO 52
<211> LENGTH: 16
<212> TYPE: PRT
<213> ORGANISM: Homo sapiens

<400> SEQUENCE: 52

Ser Glu Phe Trp Ser Ala Thr Ser Gly Ser His Ala Pro Ala Ser Asp
1               5                   10                  15

<210> SEQ ID NO 53
<211> LENGTH: 16
```

```
<212> TYPE: PRT
<213> ORGANISM: Homo sapiens

<400> SEQUENCE: 53

Thr Asp Phe Val Ser Leu Thr Ser His Leu Asn Ser Ala Val Asp Gly
1               5                   10                  15

<210> SEQ ID NO 54
<211> LENGTH: 17
<212> TYPE: PRT
<213> ORGANISM: Homo sapiens

<400> SEQUENCE: 54

Leu Ala Phe His Ser Ala Val His Gly Ile Glu Asp Leu Met Ile Gln
1               5                   10                  15

His

<210> SEQ ID NO 55
<211> LENGTH: 17
<212> TYPE: PRT
<213> ORGANISM: Homo sapiens

<400> SEQUENCE: 55

Leu Ala Tyr His Ser Ala Val His Gly Ile Glu Asp Leu Met Ser Gln
1               5                   10                  15

His

<210> SEQ ID NO 56
<211> LENGTH: 17
<212> TYPE: PRT
<213> ORGANISM: Homo sapiens

<400> SEQUENCE: 56

Leu Val Tyr His Ser Ala Val Leu Gly Ile Ser Asp Leu Met Ser Gln
1               5                   10                  15

Arg

<210> SEQ ID NO 57
<211> LENGTH: 23
<212> TYPE: PRT
<213> ORGANISM: Homo sapiens

<400> SEQUENCE: 57

Arg Gly Asp Leu Ala Phe His Ser Ala Val His Gly Ile Glu Asp Leu
1               5                   10                  15

Met Ile Gln His Asn Cys Ser
            20
```

RGMC-SELECTIVE INHIBITORS AND USE THEREOF

RELATED APPLICATIONS

This patent application is a 35 U.S.C. § 371 national stage filing of International Application No. PCT/US2019/057687, filed on Oct. 23, 2019, which claims benefit of and priority to U.S. Provisional Application Ser. No. 62/749,469, filed on Oct. 23, 2018. The contents of each of the aforementioned applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 8, 2020, is named 127036-02220_SequenceListing.txt and is 38,869 bytes in size.

FIELD OF THE INVENTION

This invention generally relates to RGMc-binding agents (e.g., antibodies and molecules comprising an antigen-binding fragments), which specifically and selectively inhibit RGMc but not RGMa or RGMb.

BACKGROUND

Abnormalities in iron homeostasis are associated with a number of diseases that can be difficult to treat. Such disorders can be broadly classified into two categories, i) iron-overload diseases that include cirrhosis, cardiomyopathy, diabetes, etc.; and, ii) iron-deficient diseases, including iron-restricted anemia, anemia of chronic disease ("ACD"), etc.

Hepcidin is a key regulator of systemic iron homeostasis, whose expression is predominantly restricted to the liver. Hepcidin is produced as a propeptide and processed by furin or furin-like protease into the mature active peptide. Hepcidin negatively regulates iron availability by binding to its receptor ferroportin, the only cellular iron exporter, and causing the internalization and degradation of both. Thus, hepcidin blocks iron export from the key cells for dietary iron absorption (enterocytes), recycling of hemoglobin iron (the macrophages) and the release of storage iron from hepatocytes, resulting in the reduction of systemic iron availability. A central role of hepcidin in systemic iron homeostasis was soon unambiguously recognized by the finding that inactivation of its gene was associated with severe iron overload in the liver and pancreas.

It has been shown that BMP6 and BMP2 expression is required to maintain iron homeostasis in mice. Bone morphogenic proteins 6 and 2, (BMP6 and BMP2, respectively) are both members of the TGFβ superfamily of growth factors known to be involved in diverse biological processes, including iron metabolism/homeostasis. It has been shown that BMP6 and BMP2 expression is required to maintain iron homeostasis in mice. Consistent with the notion that it is involved in iron regulation, genetic impairment of BMP6 causes severe tissue iron overload. Similarly, BMP6 mutations have been found in patients having hereditary hemochromatosis, a heterogeneous group of genetic disorders characterized by parenchymal iron overload.

BMP6 binds to type I and type II serine threonine kinase receptors (e.g., Alk2, Alk3, BMPR2, and ActRIIA). Moreover, BMP6 has also been shown to directly bind to its co-receptor, repulsive guidance molecule C or RGMc, also known as hemojuvelin or HJV. BMP6 binding to its receptors, and in turn the larger multimeric complex that includes HJV, HFE, TFR2, and neogenin, activates intracellular SMAD phosphorylation, which induces nuclear translocation and increased hepcidin transcription. Thus, the BMP6/HJV/SMAD axis is the major regulator of hepcidin expression that responds to iron status.

Currently available therapies for treating clinical indications involving anemia, such as Chemotherapy-Induced Anemia and the anemia of Chronic Kidney Disease, include intravenous iron (e.g., iron supplement and transfusion) and erythropoiesis stimulating agents (ESAs). Examples of ESAs include Erythropoietin (Epo); Epoetin alfa (Procrit/Epogen); Epoetin beta (NeoRecormon); Darbepoetin alfa (Aranesp); and, Methoxy polyethylene glycol-epoetin beta (Mircera). These therapies are suboptimal and can also be associated with unwanted side effects or adverse events, such as iron overload, cardiovascular and oncogenic risks.

Iron overload in anemia patients who receive frequent iron supplements, such as IV iron, is a dangerous side effect. Excess body iron can be highly toxic, which may affect a number of organs, leading to a variety of serious diseases such as liver disease, heart disease, diabetes mellitus, hormonal abnormalities, and dysfunctional immune system. Similarly, patients who receive blood transfusion are at risk of toxicities associated with iron overload. For example, a unit of transfused blood contains approximately 250 mg of iron. In patients who receive numerous transfusions, notably those with thalassemia major, sickle cell disease, myelodysplastic syndrome, aplastic anemia, hemolytic anemia, and refractory sideroblastic anemias, who may become transfusion dependent, the excess iron from the transfused erythrocytes gradually accumulates in various tissues, causing morbidity and mortality. Thus, treatment-induced excess iron in the body can cause severe adverse reactions including toxicities to cardiovascular, gastrointestinal, immune, bone/cartilage, reproductive, and renal systems. As an added or alternative treatment option to IV iron, ESA (e.g., EPO, such as Epogen® by Amgen) therapy has been extensively administered to a wide range of patient populations, including those suffering from cancer-related and chemotherapy-induced anemia in patients. Paradoxically, however, preclinical and clinical studies indicate that ESAs (e.g., EPO) could potentially accelerate tumor growth and jeopardize survival in cancer patients.

In attempt to circumvent at least some of these unwanted side effects associated with exogenously administered ESAs and iron supplements (such as transfusion), hypoxia-inducible factor prolyl hydroxylase (HIF-PH) has garnered significant attention as a potential therapeutic target aimed to promote endogenous EPO production. To this end, more recently, a number of HIF stabilizers (e.g., HIF-PH inhibitors) are under development. These include, for example, roxadustat (Fibrogen), daprodustat (GSK), vadadustat (Akebia) and molidustat (Bayer). Despite early efficacy data showing superiority or non-inferiority to ESA therapies, however, long-term concerns remain over the risk of major adverse cardiovascular events and increased risk of cancer. In particular, because the HIF axis regulates a wide range of essential biological functions in vivo (such as angiogenesis), systemic intervention of this pathway may lead to undesirable effects beyond the intended effects on erythropoiesis.

As an alternative approach, BMP6 inhibitors, including neutralizing antibodies, are being explored by several companies in an effort to treat patients with anemia (such as anti-BMP6 antibodies (e.g., WO 2016/098079, Novartis; and, KY-1070, KyMab). However, these inhibitors run the risk of adversely modulating other aspects of BMP6 signaling, including bone and cartilage formation, ovarian function, and fat metabolism.

Separately, in a 2015 paper (The AAPS Journal 17(4): 930-938) Boser et al. (AbbVie) described therapeutic use of two antibodies that bind to both RGMa and RGMc (i.e., RGMa/c) in treating anemic conditions associated with hepcidin dysregulation using two preclinical models, demonstrating enhancement of iron mobilization in vivo by the non-selective RGMa/c antibody. However, whilst RGMa is speculated to function as a tumor suppressor, as well as an immunomodulator, potential long-term risk of inhibiting the RGMa pathway was not discussed in this paper.

Thus, there remains a significant unmet need to provide an improved treatment for iron-related diseases, in particular, iron-restricted disorders caused by excessive hepcidin, e.g., anemia of chronic disease (ACD), iron-refractory iron deficiency anemia (IRIDA) and anemia of chronic kidney disease (CKD).

SUMMARY OF THE INVENTION

The inventors of the present disclosure recognized the benefit of achieving a greater level of selectivity to more specifically inhibit the signaling pathway that regulates iron homeostasis, while minimizing potential unwanted systemic effects. To that end, the inventors sought to inhibit BMP6 signaling in a liver-selective fashion by specifically targeting Repulsive Guidance molecule c (RGMc), also known as Hemojuvelin (HJV) or hemochromatosis type 2 protein (HFE2). It was reasoned that, in this way, RGMc-selective inhibitors may provide efficacy for the treatment of iron-restricted disorders, while achieving an improved safety profile, as compared to existing approaches that affect additional pathways which are required for other biological functions. It is therefore contemplated that the RGMc-selective inhibitors according to the present disclosure may achieve an improved safety profile (e.g., reduced toxicities or adverse events/effects) such as reduced risk of major adverse cardiac events (e.g., stroke) and/or reduced risk of cancer progression. Advantageously, the RGMc-selective inhibitors may reduce the risk of iron overload associated with exogenously administered iron (e.g., IV iron or transfusion). The RGMc-selective inhibitors may allow iron-restricted anemia patients to require less dosage of ESAs and/or iron supplement therapy, e.g., less frequent IV iron or transfusion.

RGMc is a member of the RGM class of proteins, namely, RGMa, RGMb and RGMc. RGMs have been reported to interact with multiple members of the BMP class of growth factors, including BMP6. RGMc is expressed as a membrane-bound and soluble forms in mammals and plays a role in iron homeostasis/metabolism within the BMP6 axis.

Both RGMa and RGMb are found in the nervous and immune systems, whilst RGMc is found in skeletal muscle but predominantly in the liver. While each of these family members shares significant structural homology, particularly across their BMP binding domains, their physiological roles are quite different. RGMa and RGMb are reported to have roles in nervous system biology, immunity, inflammation, angiogenesis, and growth. Unlike RGMa and RGMb, RGMc's known function is primarily localized to hepatocytes. As such, identification of RGMc selective-antibodies that do not bind to RGMa or RGMb could provide the potential for liver-specific modulation of BMP6 biology.

Thus, RGMc is a liver-expressed obligate co-receptor for certain BMPs, such as BMP6, that enhance hepcidin expression and, consequently, inhibit iron transport. In other words, by targeting RGMc, whose expression is more restrictive than that of RGMa, RGMb, and BMP6, more tissue-specific effects may be achieved while reducing off-target effects. This approach presents the potential to address both iron-restricted anemias and iron overload conditions without broadly inhibiting RGM and BMP6 functions throughout the body.

Accordingly, the present invention includes the recognition that selective targeting of RGMc provides an advantageous approach for achieving both efficacy and safety (reduced toxicities) as compared to conventional approaches, such as direct BMP6 antagonists and non-selective inhibitors of RGMc/RGMa/RGMb. Advantageously, unlike prior art antibodies that bind RGMc non-selectively (see, for example, PCT/US2012/069586), antibodies of the present invention are selective for RGMc over RGMa and RGMb.

Accordingly, in one aspect, the invention provides RGMc-specific antibodies, or antigen-binding fragments thereof, characterized in that they bind selectively to RGMc. In one embodiment, the invention provides an isolated antibody, or antigen-binding fragment thereof, that selectively binds to human RGMc and does not bind, or has reduced binding, to human RGMa and human RGMb. In some embodiments, the antibody, or antigen-binding fragment thereof, inhibits or reduces RGMc integration with BMPs (e.g., BMP6). In some embodiments, the antibody, or antigen-binding fragment thereof, does not inhibit or reduce RGMc interaction with neogenin.

In other aspects, the invention provides RGMc-specific antibodies, or antigen-binding fragments thereof, that bind to specific portion(s) on RGMc which may provide particularly advantageous selectivity towards RGMc over RGMa/b. In some embodiments, the RGMc-specific antibody encompassed by the present invention binds a first and/or second binding region of human RGMc, wherein the first binding region is YVSSTLSL (SEQ ID NO: 46) within the alpha1 helix domain and the second binding region is FHSAVHGIEDL (SEQ ID NO: 47) within the alpha3 helix domain. In some embodiments, the antibody, or antigen-binding fragment thereof, binds at least one amino acid residue within the first binding region and/or binds at least one amino acid residue within the second binding region.

Thus, the present disclosure provides an RGMc-selective antibody that binds an epitope comprising one or more amino acid residues of YVSSTLSL (SEQ ID NO: 46), optionally further comprising one or more amino acid residues of FHSAVHGIEDL (SEQ ID NO: 47).

The present disclosure provides an RGMc-selective antibody that binds an epitope comprising one or more amino acid residues of FHSAVHGIEDL (SEQ ID NO: 47), optionally further comprising one or more amino acid residues of YVSSTLSL (SEQ ID NO: 46).

In some embodiments, the RGMc-selective antibody binds an epitope comprising one or more amino acid residues of YVSSTLSL (SEQ ID NO: 46) and one or more amino acid residues of FHSAVHGIEDL (SEQ ID NO: 47).

In other aspects, the invention provides RGMc-specific antibodies, or antigen-binding fragments thereof, wherein the antibody is defined by amino acid sequences of its complementarity determining regions (CDRs), and variants. For example, the antibodies may include one or more CDR sequences selected from SEQ ID NOs: 6-11, SEQ ID NOs: 14-19, SEQ ID NOs: 22-27, SEQ ID NOs: 30-35, and SEQ ID NOs: 38-43. In some embodiments, each CDR contains up to 1, 2, 3, 4, or, 5 amino acid residue variations as compared to the corresponding CDR sequence.

In other aspects, the invention provides RGMc-specific antibodies, or antigen-binding fragments thereof, wherein the antibody is defined by its heavy chain variable region and/or light chain variable region sequences. For example, in some embodiments, the antibody, or antigen-binding fragment thereof, comprises a heavy chain variable region having an amino acid as set for in SEQ ID NO: 12, SEQ ID NO: 20, SEQ ID NO: 28, SEQ ID NO: 36, or SEQ ID NO: 44. In some embodiments, the antibody, or antigen-binding fragment thereof, comprises a light chain variable region having an amino acid sequence as set forth in SEQ ID NO: 13, SEQ ID NO: 21, SEQ ID NO: 29, SEQ ID NO: 37, or SEQ ID NO: 45. In some embodiments, the antibody comprises a heavy chain variable region and a light chain variable region as disclosed herein. In some embodiments, the heavy chain variable and/or light chain variable regions have an amino acid sequences that is at least 90%, 91%, 92%, 93%, 94%, 95%, 96%, 97%, 98% or 99% identical to the heavy chain variable and light chain variable regions disclosed herein.

In other aspects, the invention provides RGMc-specific antibodies, or antigen-binding fragments thereof, that compete for binding to human RGMc, and/or bind to the same epitope as, an antibody disclosed herein.

In some embodiments, preferred antibodies according to the present disclosure have the following profile: i) the mechanism of action of such antibodies is such that the antibodies bind RGMc thereby directly competing BMP6 binding in the BMP6-hepcidin signaling axis; ii) such antibodies are selective binders of RGMc over RGMa or RGMb, preferably with no detectable cross-reactivity thereto; iii) such antibodies show species cross-reactivity to human RGMc, rodent (mouse and rat) and non-human primates (e.g., cyno); iv) such antibodies have affinity to human and preferably also rodent RGMc with $K_D$ of equal to or less than 1 nM (i.e., $K_D \leq 1$ nM), more preferably ≤0.1 nM; v) such antibodies show in vivo efficacy in one or more suitable preclinical models (e.g., rats) at 10 mg/kg dose or less (preferably 5 mg/kg or less, e.g., 1 mg/kg or less) after 24-48 hours (preferably after 24 hours); and/or, vi) such antibodies allow formulations with solubility of at least 50 mg/mL, more preferably ≥100 mg/mL (for potential subcutaneous dosing). In particularly preferred embodiments, all of the above criteria (i)-(vi) are met.

In other aspects, pharmaceutical compositions comprising an antibody disclosed herein, and therapeutic use of such antibodies/compositions are provided. Such antibodies and compositions may be used in a method of treating a disease associate with RGMc in a human subject. In some embodiments, the disease associated with RGMc is anemia, e.g., iron-restricted anemia (or functional iron deficiency). In some embodiments, the anemia may be iron-deficiency anemia (IRIDA), anemia of chronic disease (ACD), treatment-induced anemia (e.g., chemotherapy-induced anemia), cancer-related anemia, or anemia associated with chronic kidney disease (CKD). The CKD may be dialysis-dependent CKD. The CKD may be non-dialysis-dependent CKD.

In some embodiments, the pharmaceutical compositions/antibodies may be administered to patients who are receiving or have received another therapeutic agent (e.g., erythropoietin stimulating agent, HIF stabilizer, iron supplement, iron transfusion, anti-cancer agent, and/or an anti-inflammatory). In some embodiments, the method reduces toxicities associate with ESAs, iron supplements or iron transfusion.

Thus, when used in conjunction with another therapy for anemia (e.g., erythropoietin stimulating agent, HIF stabilizer, iron supplement, iron transfusion, anti-cancer agent, and/or an anti-inflammatory), RGMc-selective inhibitors disclosed herein may decrease the need for the therapy, such that the dosage and/or frequency of the therapy may be reduced.

In some embodiments, the pharmaceutical compositions/antibodies may be used to achieve faster relief of anemia when used in conjunction with another therapy for anemia (e.g., erythropoietin stimulating agent, HIF stabilizer, iron supplement, iron transfusion, anti-cancer agent, and/or an anti-inflammatory) in a subject.

In some embodiments, the pharmaceutical compositions/antibodies may be used to reduce iron overload associated with iron therapy, such as transfusions and IV iron in patients.

In some embodiments, pharmaceutical compositions/antibodies may be used to sensitize ESA-hyporesponsive anemia. For example, approximately 5-10% of patients with CKD who have received ESA therapy show hyporesponsiveness to ESA (ESA resistance). RGMc-selective inhibitors disclosed herein may be used to render this type of anemia more responsive to ESA therapy.

According to the invention, the RGMc-selective inhibitor encompassed herein can be used in the treatment of anemia in an amount effective to achieve one or more of the following: increasing serum iron in a subject, downregulating hepcidin expression in a subject, increasing transferrin saturation in a subject, increasing erythropoiesis in a subject, decreasing unsaturated iron binding capacity (UIBC) in a subject, decreasing total iron binding capacity (TIBC) in a subject, and/or increasing serum ferritin levels in a subject.

In other aspect, the invention provides methods for making a pharmaceutical composition comprising an RGMc-selective inhibitor, the method comprising the steps of: i) identifying antibodies or antigen-binding fragments thereof, for the ability to selectively bind RGMc over RGMa and RGMb; ii) identifying the antibodies or antigen-binding fragment based on step (i) for the ability to inhibit/neutralize RGMc activity in vivo; and iii) selecting an inhibitory/neutralizing antibody based on steps (i) and (ii) for formulation into a pharmaceutical composition. In some embodiments, the method for making further comprises a positive selection step and optionally a negative selection step. In some embodiments, the identification step (ii) further comprises measuring an iron parameter selected from the group consisting of serum iron, TIBC, UIBC, hepcidin expression, and transferrin saturation.

BRIEF DESCRIPTION OF THE FIGURES

FIG. 8B depicts the amino acid sequences of deuterium protected regions A and B aligned across RGM family proteins. The left panel shows an alignment of amino acids 44 to 74 of SEQ ID NO: 1 (RGMc) against amino acids 63 to 78 of SEQ ID NO: 4 (RGMa) and amino acids 102 to 117 of SEQ ID NO: 5 (RGMb). The right panel shows an alignment of amino acids 101 to 117 of SEQ ID NO: 1 (RGMc) against amino acid positions 105 to 121 of SEQ ID NO: 4 (RGMa) and amino acids 144 to 160 of SEQ ID NO: 5 (RGMb).

FIG. 8E is a diagram showing structural homology of the H/D exchange protected region A within alpha helices 1/2/3 of RGMa/b/c and highlighting potential structural determinants of SR-RC-AB9 specificity to RGMc over RGMa and RGMb.

FIG. 9A shows serum iron parameters (serum iron and UIBC, mean±SEM)) over time following a single IV. dose of SR-RC-AB8 at 10 mg/kg in female Cynomolgus macaques. FIG. 9B shows the average serum concentration (mean±SEM) of SR-RC-AB8 up to 10 weeks after dosing. FIG. 9C illustrates the relationship between antibody exposure (PK) and serum iron parameters (PD). All values are mean±SD.

DETAILED DESCRIPTION OF CERTAIN EMBODIMENTS

Definitions

Figure 1:
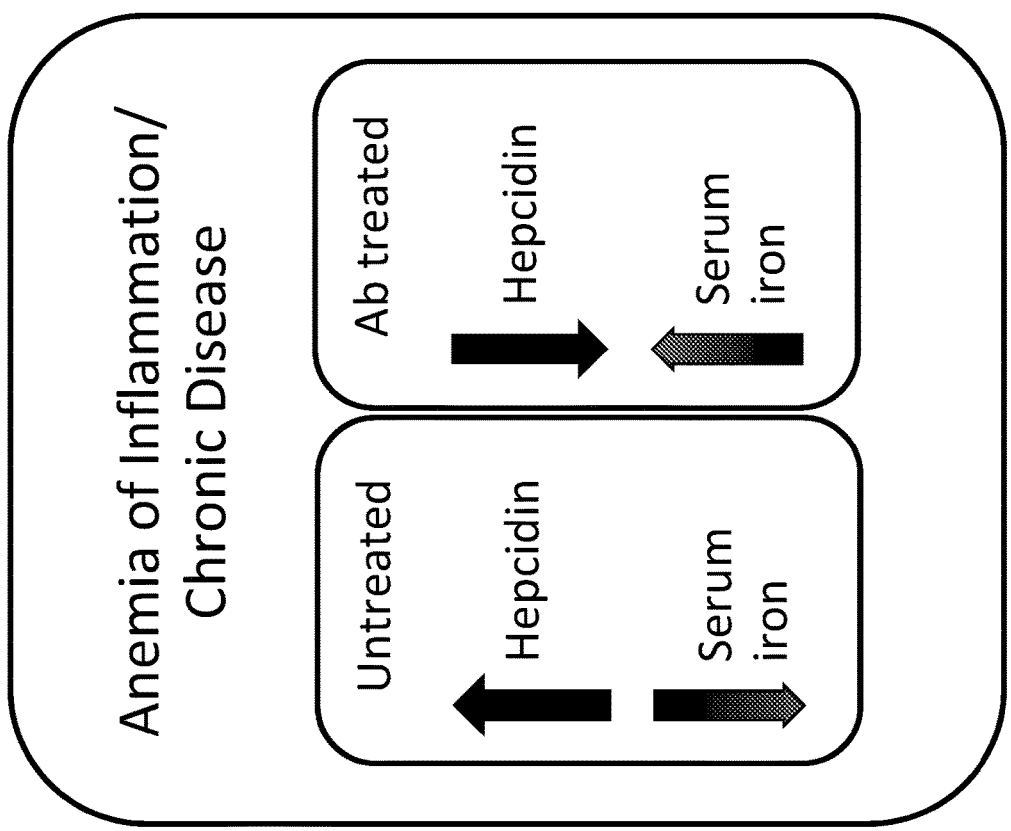
FIG. 1 is a depiction of the relationship between hepcidin and serum iron levels in anemia of inflammation/chronic disease. The depiction also shows how an RGMc antagonist (e.g., RGMc-specific antibody) is expected to reduce hepcidin levels and increase serum iron.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

Affinity: Affinity is the strength of binding of a molecule (such as an antibody) to its ligand (such as an antigen). It is typically measured and reported by the equilibrium dissociation constant ($K_D$). $K_D$ is the ratio of the antibody dissociation rate ("off rate" or $K_{off}$), how quickly it dissociates from its antigen, to the antibody association rate ("on rate" or $K_{on}$) of the antibody, how quickly it binds to its antigen. For example, an antibody with an affinity of ≤5 nM has a $K_D$ value that is 5 nM or lower (i.e., 5 nM or higher affinity) determined by a suitable in vitro binding assay such as Biolayer Interferometry (BLI)-based assays (e.g., Octet®), surface plasmon resonance (SPR)-based assays (e.g., Biacore) and solution equilibrium titration-based assays (e.g., Meso Scale Discovery or MDS).

Anemia: Anemia is a medical condition in which the red blood cell count or hemoglobin is less than normal. For men, anemia is typically defined as hemoglobin level of less than 13.5 gram/100 ml and in women as hemoglobin of less than 12.0 gram/100 ml. Anemia may be caused by either a decrease in production of red blood cells or hemoglobin, or an increase in loss (usually due to bleeding) or destruction of red blood cells. Anemia may be diagnosed by, for example, measuring serum iron parameters, which, when deviated from normal ranges can be indicative of anemia. Useful iron parameters include: serum iron, total iron binding capacity (TIBC), unsaturated iron binding capacity (UIBC), and transferrin saturation. Transferrin saturation can be calculated from the serum iron divided by the total iron binding capacity (TIBC), expressed as a percentage.

Anemia of chronic disease: The term "anemia of chronic disease" or "ACD" as used herein, refers a form of anemia that is the result of another condition. Such conditions may be associated with chronic infection, chronic immune activation, and/or malignancy (e.g., chronic kidney disease or cancer).

Antibody: The term "antibody" encompasses any naturally-occurring, recombinant, modified or engineered immunoglobulin or immunoglobulin-like structure or antigen-binding fragment or portion thereof, or derivative thereof, as further described elsewhere herein. Thus, the term refers to an immunoglobulin molecule that specifically binds to a target antigen, and includes, for instance, chimeric, humanized, fully human, and bispecific antibodies. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be "chimeric," that is, different portions of the antibody can be derived from two different antibodies. Antibodies, or antigen-binding portions thereof, can be produced in hybridomas, by recombinant DNA techniques, or by enzymatic or chemical cleavage of intact antibodies. The term antibodies, as used herein, includes monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), respectively. In some embodiments, the term also encompasses peptibodies.

Antigen: The term "antigen" The term "antigen" broadly includes any molecules comprising an antigenic determinant within a binding region(s) to which an antibody or a fragment specifically binds. An antigen can be a single-unit molecule (such as a protein monomer or a fragment) or a complex comprised of multiple components. An antigen provides an epitope, e.g., a molecule or a portion of a molecule, or a complex of molecules or portions of molecules, capable of being bound by a selective binding agent, such as an antigen-binding protein (including, e.g., an antibody). Thus, a selective binding agent may specifically bind to an antigen that is formed by two or more components in a complex. In some embodiments, the antigen is capable of being used in an animal to produce antibodies capable of binding to that antigen. An antigen can possess one or more epitopes that are capable of interacting with different antigen-binding proteins, e.g., antibodies.

Antigen-binding portion/fragment: The terms "antigen-binding portion" or "antigen-binding fragment" of an antibody, as used herein, refers to one or more fragments of an antibody that retain the ability to specifically bind to an antigen (e.g., RGMc/HJV). Antigen-binding portions include, but are not limited to, any naturally occurring, enzymatically obtainable, synthetic, or genetically engineered polypeptide or glycoprotein that specifically binds an antigen to form a complex. In some embodiments, an antigen-binding portion of an antibody may be derived, e.g., from full antibody molecules using any suitable standard techniques such as proteolytic digestion or recombinant genetic engineering techniques involving the manipulation and expression of DNA encoding antibody variable and optionally constant domains. Non-limiting examples of antigen-binding portions include: (i) Fab fragments, a monovalent fragment consisting of the VL, VH, CL and CH1 domains; (ii) F(ab')2 fragments, a bivalent fragment comprising two Fab fragments linked by a disulfide bridge at the hinge region; (iii) Fd fragments consisting of the VH and CH1 domains; (iv) Fv fragments consisting of the VL and VH domains of a single arm of an antibody; (v) single-chain Fv (scFv) molecules (see, e.g., Bird et al. (1988) SCIENCE 242:423-426; and Huston et al. (1988) PROC. NAT'L. ACAD. SCI. USA 85:5879-5883); (vi) dAb fragments (see, e.g., Ward et al. (1989) NATURE 341: 544-546); and (vii) minimal recognition units consisting of the amino acid residues that mimic the hypervariable region of an antibody (e.g., an isolated complementarity determining region (CDR)). Other forms of single chain antibodies, such as diabodies are also encompassed. The term antigen-binding portion of an antibody includes a "single chain Fab fragment" otherwise known as an "scFab," comprising an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids.

Binding region: As used herein, a "binding region" is a portion of an antigen that, when bound to an antibody or a fragment thereof, can form an interface of the antibody-antigen interaction. Upon antibody binding, a binding region becomes protected from surface exposure, which can be detected by suitable techniques, such as hydrogen deuterium exchange mass spectrometry (HDX-MS). Antibody-antigen interaction may be mediated via multiple (e.g., two or more) binding regions. A binding region can comprise an antigenic determinant, or epitope.

Biolayer Interferometry (BLI): BLI is a label-free technology for optically measuring biomolecular interactions, e.g., between a ligand immobilized on the biosensor tip surface and an analyte in solution, which enables real-time measurements of affinities of antibodies. BLI provides the ability to monitor binding specificity, rates of association (e.g., "on" rate) and dissociation (e.g., "off" rate), or concentration, with precision and accuracy. BLI platform instruments are commercially available, for example, from ForteBio and are commonly referred to as the Octet® System.

BMP61BMP-6: As used herein, the terms "bone morphogenetic protein 6", "BMP6 (or BMP-6)", "VGR", and "VGR1" all refer to a protein that is a member of the bone morphogenetic family of proteins, which interacts with RGMc molecules as a co-receptor, e.g., human BMP6 Accession No. NP_001709.

Cancer-related anemia: The term "cancer-related anemia" or CRA, may also be referred to as "cancer-associated anemia", means anemia which is associated with, cause by and/or exacerbated by, the presence of a cancer.

Chemotherapy-induced anemia: The term "chemotherapy-induced anemia", or CIA, also referred to as "chemotherapy-associated anemia", is one type of treatment-induced anemia and refers to anemia that is caused by and/or exacerbated by chemotherapy. In the context of the present disclosure, the term "chemotherapy" shall encompass any anti-cancer agents, drugs and therapies intended to treat cancer (e.g., kill malignant cells) in patients, which impair hematopoiesis.

Chronic kidney disease: The term "chronic kidney disease" (CKD) refers to kidney disease in which there is a gradual loss of kidney function over a period of months to years. For example, such kidney disease may be cause by diabetes, high blood pressure, glomerulonephritis, and polycystic kidney disease. CKD is associated with insufficient production of erythropoietin (EPO) by kidney cells, which results in fewer red cells produced in the bone marrow, eventually leading to anemia.

Clinical benefit: As used herein, the term "clinical benefits" is intended to include both efficacy and safety of a therapy. Thus, therapeutic treatment that achieves a desirable clinical benefit is both efficacious and safe (e.g., with tolerable or acceptable toxicities or adverse events).

Combination therapy: "Combination therapy" refers to treatment regimens for a clinical indication that comprise two or more therapeutic agents. Thus, the term refers to a therapeutic regimen in which a first therapy comprising a first composition (e.g., active ingredient) is administered in conjunction with a second therapy comprising a second composition (active ingredient) to a subject, intended to treat the same or overlapping disease or clinical condition. The first and second compositions may both act on the same cellular target, or discrete cellular targets. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

Combinatory or combinatorial epitope: A combinatorial epitope is an epitope that is recognized and bound by a combinatorial antibody at a site (i.e., antigenic determinant) formed by non-contiguous portions of a component or components of an antigen, which, in a three-dimensional structure, come together in close proximity to form the epitope. A combinatorial epitope is also referred to as a discontinuous epitope. Thus, antibodies of the invention may bind an epitope formed by two or more components (e.g., portions or segments) of RGMc. A combinatory epitope may comprise amino acid residue(s) from a first portion/component of RGMc, and amino acid residue(s) from a second portion/component of RGMc, and so on. Each portion/component may be of a single protein or of two or more proteins of an antigenic complex. A combinatory epitope is formed with structural contributions from two or more components (e.g., portions or segments, such as amino acid residues) of an antigen or antigen complex.

Compete or cross-compete: The term "compete" when used in the context of antigen-binding proteins (e.g., an antibody or antigen-binding fragment thereof) that compete for the same epitope means competition between antigen-binding proteins as determined by an assay in which the antigen-binding protein being tested prevents or inhibits (e.g., reduces) specific binding of a reference antigen-binding protein to a common antigen (e.g., RGMc or a fragment thereof). Numerous types of competitive binding assays can be used to determine if one antigen-binding protein competes with another, for example: solid phase direct or indirect radioimmunoassay (RIA), solid phase direct or indirect enzyme immunoassay (EIA), sandwich competition assay; solid phase direct biotin-avidin EIA; solid phase direct labeled assay, and solid phase direct labeled sandwich assay. Usually, when a competing antigen-binding protein is present in excess, it will inhibit (e.g., reduce) specific binding of a reference antigen-binding protein to a common antigen by at least 40-45%, 45-50%, 50-55%, 55-60%, 60-65%, 65-70%, 70-75% or 75% or more. In some instances, binding is inhibited by at least 80-85%, 85-90%, 90-95%, 95-97%, or 97% or more. In some embodiments, a first antibody or antigen-binding fragment thereof and a second antibody or antigen-binding fragment thereof cross-block with each other with respect to the same antigen, for example, as assayed by Biacor or Octet, using standard test conditions, e.g., according to the manufacturer's instructions (e.g., binding assayed at room temperature, ~20-25° C.). In some embodiments, the first antibody or fragment thereof and the second antibody or fragment thereof may have the same epitope. In other embodiments, the first antibody or fragment thereof and the second antibody or fragment thereof may have non-identical but overlapping epitopes. In yet further embodiments, the first antibody or fragment thereof and the second antibody or fragment thereof may have separate (different) epitopes which are in close proximity in a three-dimensional space, such that antibody binding is cross-blocked via steric hindrance. "Cross-block" means that binding of the first antibody to an antigen prevents binding of the second antibody to the same antigen, and similarly, binding of the second antibody to an antigen prevents binding of the first antibody to the same antigen.

Complementary determining region: As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region that can bind the antigen. The exact boundaries of these CDRs have been defined differently according to different systems. The system described by Kabat (Kabat et al. (1987; 1991) Sequences of Proteins of Immunological Interest (National Institutes of Health, Bethesda, Md.) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk (1987) J. Mol. Biol. 196: 901-917; and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2 and L3 or H1, H2 and H3, where the "L" and the "H" designate the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5): 732-45. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen-binding. The methods used herein may utilize CDRs defined according to any of these systems, although certain embodiments use Kabat or Chothia defined CDRs.

Conformational epitope: A conformational epitope is an epitope that is recognized and bound by a conformational antibody in a three-dimensional conformation, but not in an unfolded peptide of the same amino acid sequence. A conformational epitope may be referred to as a conformation-specific epitope, conformation-dependent epitope, or conformation-sensitive epitope. A corresponding antibody or fragment thereof that specifically binds such an epitope may be referred to as conformation-specific antibody, conformation-selective antibody, or conformation-dependent antibody. Binding of an antigen to a conformational epitope depends on the three-dimensional structure (conformation) of the antigen or antigen complex.

Constant region: An immunoglobulin constant domain refers to a heavy or light chain constant domain. Human IgG heavy chain and light chain constant domain amino acid sequences are known in the art.

Effective amount: An "effective amount" (or therapeutically effective amount) is a dosage or dosing regimen that achieves statistically significant clinical benefits in a patient population.

Epitope: The term "epitope" may be also referred to as an antigenic determinant, is a molecular determinant (e.g., polypeptide determinant) that can be specifically bound by a binding agent, immunoglobulin or T-cell receptor. Epitope determinants include chemically active surface groupings of molecules, such as amino acids, sugar side chains, phosphoryl, or sulfonyl, and, in certain embodiments, may have specific three-dimensional structural characteristics, and/or specific charge characteristics. An epitope recognized by an antibody or an antigen-binding fragment of an antibody is a structural element of an antigen that interacts with CDRs (e.g., the complementary site) of the antibody or the fragment. An epitope may be formed by contributions from several amino acid residues, which interact with the CDRs of the antibody to produce specificity. An antigenic fragment can contain more than one epitope. In certain embodiments, an antibody is the to specifically bind an antigen when it recognizes its target antigen in a complex mixture of proteins and/or macromolecules. For example, antibodies are said to "bind to the same epitope" if the antibodies cross-compete (one prevents the binding or modulating effect of the other).

Erythropoiesis-stimulating agent: The term "erythropoiesis-stimulating agent" or "ESA" as used herein refers to medications that stimulate the bone marrow to produce red blood cells. Erythropoietin or EPO is one example of an ESA and may include erythropoietin alfa, delta, omega, and zeta, including engineered forms of erythropoietin, e.g., darbepoetin alfa. The term "EPO therapy" may be used to broadly encompass therapies that employ one or more ESA agents.

Human antibody: The term "human antibody" (or "fully human antibody") as used herein, is intended to include antibodies having variable and constant regions derived from human germline immunoglobulin sequences. The human antibodies of the present disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

Humanized antibody: The term "humanized antibody" refers to antibodies, which comprise heavy and light chain variable region sequences from a non-human species (e.g., a mouse) but in which at least a portion of the VH and/or VL sequence has been altered to be more "human-like," i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody, or a variant, derivative, analog or fragment thereof, which immunospecifically binds to an antigen of interest and which comprises an FR region having substantially the amino acid sequence of a human antibody and a CDR region having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the FR regions are those of a human immunoglobulin consensus sequence. In an embodiment a humanized antibody also comprises at least a portion of an immunoglobulin Fc region, typically that of a human immunoglobulin. In some embodiments a humanized antibody contains the light chain as well as at least the variable domain of a heavy chain. The antibody also may include the CH1, hinge, CH2, CH3, and CH4 regions of the heavy chain. In some embodiments a humanized antibody only contains a humanized light chain. In some embodiments a humanized antibody only contains a humanized heavy chain. In specific embodiments a humanized antibody only contains a humanized variable domain of a light chain and/or humanized heavy chain.

Hydrogen deuterium exchange mass spectrometry (HDX-MS): HDX-MS is a well-known technique employed to interrogate protein confirmation and protein-protein interactions in solution by measuring the degree of solvent accessibility. See, for example, Wei et al., (2014) Drug Discov Today 19(1): 95-102. "Hydrogen/deuterium exchange mass spectrometry for probing higher order structure of protein therapeutics: methodology and applications."

Hypoxia-inducible factor (HIF) stabilizer: HIF prolyl-hydroxilase (HIF-PH) inhibitors can stabilize HIF (e.g., HIF-2a) thereby may result in increased endogenous production of erythropoietin (EPO) in vivo. These agents may be also referred to as "HIF activators." Examples of HIF stabilizers include, but are not limited to: Roxadustat (FG-4592); Vadadustat (AKB-6548); Daprodustat (GSK1278863), Dsidustat (ZYAN-1), Molidustat (Bay 85-3934); MK-8617, YC-1, IOX-2, 2-methoxyestradiol, GN-44028, AKB-4924, Bay 87-2243, FG-2216 and FG-4497.

Iron therapy: An "iron therapy" as used herein, refers to a therapeutic treatment comprising an iron supplement (e.g., oral or intravenous (i.v.) iron).

Isolated: An "isolated" antibody as used herein, refers to an antibody that is substantially free of other antibodies having different antigenic specificities. In some embodiments, an isolated antibody is substantially free of other unintended cellular material and/or chemicals.

Potency: The term "potency" as used herein refers to activity of a drug, such as an inhibitory antibody (or fragment) having inhibitory activity, with respect to concentration or amount of the drug to produce a defined effect. For example, an antibody capable of producing certain effects at a given dosage is more potent than another antibody that requires twice the amount (dosage) to produce equivalent effects. Potency may be measured, for example, by in vitro assays, such as BMP6 activation/inhibition assays as described herein. Potency may also be measured by in vivo assays, such as those that measure hepcidin expression, serum iron, ferritin expression, and iron binding capacity as described herein. Typically, antibodies with higher affinities tend to show higher potency than antibodies with lower affinities.

Protection (from solvent exposure): In the context of HDX-MS-based assessment of protein-protein interactions, such as antibody-antigen-binding, the degree by which a protein (e.g., a region of a protein containing an epitope) is exposed to a solvent, thereby allowing proton exchange to occur, inversely correlates with the degree of binding/interaction. Therefore, when an antibody described herein binds to a region of an antigen, the binding region is "protected" from being exposed to the solvent because the protein-protein interaction precludes the binding region from being accessible by the surrounding solvent. Thus, the protected region is indicative of a site of interaction. Typically, suitable solvents are physiological buffers.

RGM: As used herein, "RGM" refers to a class of proteins belonging to the repulsive guidance molecule family.

RGMc: As used herein, the terms "repulsive guidance molecule C", "RGMc", "hemojuvelin", "HJV", "hemochromatosis type 2 protein", and "HFE2A" all refer to a protein that is a member of the repulsive guidance molecule family of proteins, which interacts with BMP molecules as a co-receptor, e.g., human RGMc Accession No. NP_998818; SEQ ID NO: 1.

RGMc-associated disorder: A "RGMc-associated disorder" means i) any disease or disorder, in which at least part of the pathogenesis and/or progression is attributable to RGMc signaling or dysregulation thereof, and/or, ii) conditions in which inhibition of RGMc may provide clinical benefit. RGMc disorders may include, for example: anemia associated with inflammation/chronic disease (e.g., Castleman's Syndrome, Chronic Kidney Disease, Diabetes, Heart Failure/Heart Disease, Idiopathic Autoimmune Hemolytic Anemia, Idiopathic Pulmonary Arterial Hypertension, Inflammatory Bowel Disease, Rheumatoid Arthritis, Systemic Lupus Erythematosus, Systemic Juvenile Idiopathic Arthritis), anemia associated with cancer/proliferative disorders (e.g., Acute Leukemia, Diffuse Large B-cell Lymphoma, Hodgkin's Lymphoma, Multiple Myeloma, Myelodysplastic Syndrome, Non-Hodgkin's Lymphoma, Waldenstrom macroglobulinemia, Bladder cancer, Breast cancer, Colorectal cancer, Gastric cancer, Head and Neck cancer, Hepatocellular cancer, lung cancer, ovarian cancer, prostate cancer, and renal cancer), anemia associated with infections (e.g., endocarditis, *Helicobacter pylori* infection, hepatitis, human immunodeficiency virus, malaria), anemia associated with neurological disorders (e.g., acute ischemic stroke, Amyotrophic Lateral Sclerosis (ALS), Focal Brain Ischemia/reperfusion, Intracranial Cerebral Hemorrhage, and Subarachnoid Hemorrhage), treatment-induced or treatment-associated anemia (e.g., antibiotic-induced, bariatric surgery-associated, chemotherapy-induced, secondary iron overload), anemia associated with genetic disorders or other conditions (e.g., age-associated (anemia in elderly), anemia of critical illness, anemia of surgery, blood loss/hemorrhage, calciphylaxis, celiac disease, copper deficiency, Fanconi Anemia, hereditary hemochromatosis (Type 4), hereditary spherocytosis, IRIDA, obesity, organ transplant, paroxysmal nocturnal hemoglobinuria, sickle cell anemia, sports/exercise-induced anemia, thalassemia, thrombotic thrombocytopenic purpura).

RGM inhibitor: The term "RGM inhibitor" or "RGM antagonist" refers to any agent capable of antagonizing biological activities or function of RGM (e.g., RGMa, RGMb, and/or RGMc). The term is not intended to limit its mechanism of action and includes, for example, neutralizing antibodies, competitive inhibitors, receptor antagonists, furin and/or TMPRSS6 cleavage enhancers, and soluble RGM peptides.

RGMc-selective inhibitor: The term "RGMc-selective" (or "RGMc-specific") inhibitor refers to an agent (including small molecules and biologics, e.g., antibodies) capable of selectively antagonizing biological activities or function of RGMc over RGMa and RGMb. For clarity, a monoclonal antibody that binds and inhibits/neutralizes both RGMa and RGMc is not an RGMc-selective inhibitor.

Specific binding: As used herein, the term "specific binding" or "specifically binds" means that the interaction of the antibody, or antigen-binding fragment thereof, with an antigen is dependent upon the presence of a particular structure (e.g., an antigenic determinant or epitope). For example, the antibody, or antigen-binding fragment thereof, binds to a specific protein rather than to proteins generally.

In some embodiments, an antibody, or antigen-binding fragment thereof, specifically binds to a target, e.g., RGMc, if the antibody has a $K_D$ for the target of at least about $10^{-8}$ M, $10^{-9}$ M, $10^{-10}$ M, $10^{-11}$ M, $10^{-12}$ M, $10^{-13}$ M, or less. In some embodiments, the term "specific binding to an epitope of RGMc", "specifically binds to an epitope of RGMc", "specific binding to RGMc", or "specifically binds to RGMc" as used herein, refers to an antibody, or antigen-binding fragment thereof, that binds to RGMc and has a dissociation constant ($K_D$) of $1.0 \times 10^{-7}$ M or less, as determined by suitable in vitro binding assays, such as surface plasmon resonance and Biolayer Interferometry (BLI). In one embodiment, an antibody, or antigen-binding fragment thereof, can specifically bind to both human and a non-human (e.g., mouse) orthologues of RGMc. For example, in some embodiments, the antibody, or antigen-binding fragment thereof, has less than a 5-fold difference in cross-reactivity to human, mouse, rate and/or cynomolgus RGMc.

The antibody, or antigen-binding fragment thereof, may also have low cross reactivity with other RGM family members (e.g., human RGMa and human RGMb). Accordingly, in some embodiments the antibody, or antigen-binding fragment thereof, binds to human RGMc with a higher affinity than human RGMa and/or human RGMb (i.e., has low cross-reactivity). For example, in some embodiments, the antibody, or antigen-binding fragment thereof, binds to human RGMc with at least a 1000-fold higher affinity (i.e., 1000-fold lower $K_D$) than to human RGMa and/or human RGMb.

Subject: The term "subject" in the context of therapeutic applications refers to an individual who receives clinical care or intervention, such as treatment, diagnosis, etc. Suitable subjects include vertebrates, including but not limited to mammals (e.g., human and non-human mammals). Where the subject is a human subject, the term "patient" may be used interchangeably. In a clinical context, the term "a patient population" or "patient subpopulation" is used to refer to a group of individuals that falls within a set of criteria, such as clinical criteria (e.g., disease presentations, disease stages, susceptibility to certain conditions, responsiveness to therapy, etc.), medical history, health status, gender, age group, genetic criteria (e.g., carrier of certain mutation, polymorphism, gene duplications, DNA sequence repeats, etc.) and lifestyle factors (e.g., smoking, alcohol consumption, exercise, etc.).

Surface plasmon resonance (SPR): Surface plasmon resonance is an optical phenomenon that enables detection of unlabeled interactants in real time. The SPR-based biosensors, such as those commercially available from Biacore, can be employed to measure biomolecular interactions, including protein-protein interactions, such as antigen-antibody binding. The technology is widely known in the art and is useful for the determination of parameters such as binding affinities, kinetic rate constants and thermodynamics.

Total iron-binding capacity: The term "total iron binding capacity", "TIBC", or "transferrin iron binding capacity" as used herein, refers to laboratory test that measures the blood's capacity to bind iron with transferrin. TIBC is determined by measuring the maximum amount of iron that the blood can carry, which is an indirect measurement of transferrin. Typically, TIBC is calculated by measuring serum iron and serum unsaturated iron-binding capacity (UIBC) and added the two values together. Alternatively, TIBC can be measured directly by adding an excess amount of iron to a sample, removing the unbound iron, and measuring the iron that is dissociated from transferrin. Generally, a "normal" range for TIBC is, e.g., 255-450 ug/dL, although measurements may vary among populations.

Toxicity: As used herein, the term "toxicity" or "toxicities" refers to unwanted in vivo effects in patients associated with a therapy administered to the patients, such as undesirable side effects and adverse events. "Tolerability" refers to a level of toxicities associated with a therapy or therapeutic regimen, which can be reasonably tolerated by patients, without discontinuing the therapy due to the toxicities. In the context of the present disclosure, toxicities may include, but are not limited to: greater risk for death, adverse cardiovascular reactions and/or stroke, which may be associated with chronic disease such as chronic kidney disease (CKD), and, shortened overall survival, increased risk of tumor progression or recurrence in cancer patients.

Treat treatment: The term "treat" or "treatment" includes therapeutic treatments, prophylactic treatments, and applications in which one reduces the risk that a subject will develop a disorder or other risk factor. Thus the term is intended to broadly mean: causing therapeutic benefits in a patient by, for example, enhancing or boosting the body's immunity; reducing or reversing immune suppression; reducing, removing or eradicating harmful cells or substances from the body; reducing disease burden (e.g., tumor burden); preventing recurrence or relapse; prolonging a refractory period, and/or otherwise improving survival. The term includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In the context of combination therapy, the term may also refer to: i) the ability of a second therapeutic to reduce the effective dosage of a first therapeutic so as to reduce side effects and increase tolerability; ii) the ability of a second therapy to render the patient more responsive (e.g., sensitize) to a first therapy; iii) the ability to effectuate additive or synergistic clinical benefits; and/or, iv) the ability to achieve faster onset of relief (e.g., therapeutic benefits).

Unbound iron-binding capacity: The term "unbound iron binding capacity" or "UIBC", as used herein, refers to the amount of available iron binding capacity of transferrin. UIBC is often calculated by assessing the difference between the TIBC and the amount of serum iron. Alternatively, UIBC can be calculated directly by adding a known amount of excess iron to a sample and subtracting the remaining unbound iron. Generally, although measurements may vary among populations or individuals, a "normal" range for UIBC is, e.g., 120-470 ug/dL (21-84 umol/L).

Variable region: The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. In certain embodiments, variable regions of different antibodies differ extensively in amino acid sequence even among antibodies of the same species. The variable region of an antibody typically determines specificity of a particular antibody for its target.

Other than in the operating examples, or where otherwise indicated, all numbers expressing quantities of ingredients or reaction conditions used herein should be understood as modified in all instances by the term "about."

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, e.g., 10-20, 1-10, 30-40, etc.

Regulation of Iron Homeostasis Via BMP6/Hepcidin Axis

Hepcidin is a small, liver-secreted peptide and the central regulator of iron homeostasis in the body. Its main function is to inhibit transport of iron from cells to the plasma compartment of blood from three main sources: the absorption of dietary iron across the duodenal enterocytes, the release of hemoglobin iron from recycled red blood cells, and the release of stored iron from hepatocytes. Regulation of iron is achieved by hepcidin-mediated degradation of the iron exporter ferroportin, located on the surface of duodenal enterocytes, liver- and spleen-resident reticuloendothelial macrophages, and hepatocytes. Because ferroportin is degraded, macrophages and duodenal enterocytes are no longer able to release iron into the blood and, as a consequence, iron transfer to transferrin is reduced. Accordingly, as shown in FIG. 1, as hepcidin expression increases, iron export decreases. Conversely, as hepcidin expression decreases, iron export increases. Accordingly, inherited and acquired disorders that upset normal hepcidin production can cause iron deficiency (high hepcidin levels) or iron overload (hepcidin deficiency).

As the principal player in the maintenance of iron homeostasis, hepcidin synthesis is regulated transcriptionally by several stimuli, including intra- and extracellular iron concentrations, erythropoietic demand, and inflammation. In healthy individuals, hepcidin is maintained at homeostatic levels due to the activity of a group of coordinating proteins in the iron regulatory complex. Genetic analyses of patients suffering from hereditary hemochromatosis (HH), in whom genetic mutations cause excess dietary iron absorption and storage in the periphery with tissue/organ toxicity, led to the identification of key proteins regulating iron homeostasis. The most common type of HH is caused by mutations in the HFE gene, which encodes an atypical MHC-class protein that interferes with transferrin-transferrin receptor binding. Rarer forms of HH occur in patients with mutations in TFR2, Hepcidin, and HJV (hereafter referred to as "RGMc"). Each of these rare forms are characterized by inappropriately low hepcidin levels, supporting roles for RGMc, HFE, and TFR2 in the upstream regulation of hepcidin expression. Intriguingly, mutations in RGMc are the most common cause of a severe form of juvenile HH, which, if left untreated, can be fatal.

Hepcidin expression is stimulated by extracellular stimuli, including the inflammatory signal IL-6, and the developmental signaling Bone Morphogenetic Proteins (BMPs). Mice with targeted deletion of BMP signaling components (specific ligands, receptors, and co-receptors) are characterized by iron overload phenotypes, highlighting the critical role of BMP signaling in hepcidin expression. Regulation of BMP signaling occurs at multiple levels in order to generate specificity and fine-tuning of the signal; co-receptor enhancement or interference with ligand-receptor interaction is a predominant mechanism for BMP signaling regulation. RGMc is the key co-receptor for BMP-mediated enhancement of hepcidin expression in the liver and is thought to sensitize hepatocytes to low BMP levels under normal physiological conditions, thereby enhancing hepcidin expression and regulating iron homeostasis. Due to its potency and confined role in iron regulation, RGMc is an attractive therapeutic target for disorders in which hepcidin-associated iron restriction plays a key role, such as the anemia of chronic disease.

BMPs are a broad subfamily of growth factors in the TGFβ superfamily originally discovered by their ability to induce the formation of bone and cartilage. Beyond their association with bone, like many other growth factors, the BMPs are involved in a diverse set of biological processes. For example, while BMP6 plays roles in many different biologies, including fat metabolism and ovarian physiology, in the liver it functions as a critical control point in iron modulation in humans via regulation of hepcidin, a central regulator of iron homeostasis.

As such, BMP6 has been an alternative therapeutic target for treating diseases and disorders involving iron dysregulation. Multiple groups, including Eli Lilly and Novartis, have developed antibodies that specifically bind to and neutralize BMP6 and proposed therapeutic use of such antibodies for treating conditions, such as anemia. However, these approaches aimed to directly inhibit the BMP6 signaling systemically would likely perturb the numerous different physiological processes in which BMP6 is involved, elevating the risk of causing inadvertent and unwanted effects (e.g., toxicities).

More recently, the Repulsive Guidance Molecules (RGMs) have been identified as BMP-interacting proteins. The RGM family of proteins includes at least three known members, namely, RGMa, RGMb, and RGMc, and are so called due to the role of the founding member, RGMa, in guiding axon growth during embryogenesis.

Structurally, RGMs are glycosylphosphatidyl-inositol (GPI) anchored proteins consisting of an N-terminal signal sequence, a RGD motif (RGMa and RGMc), a partial von Willebrand type D (vWFD) domain, and an autocatalytic Gly-Asp-Pro-His (GDPH) cleavage site. RGMs have been reported to interact with multiple members of the BMP class of growth factors, including BMP6 as a co-receptor. Each of the RGM family members shares significant structural homology (see Table 1), particularly across their BMP binding domains. RGMa and RGMc in particular share high sequence homology.

Despite considerable homology among the family members, their expressions and biological functions appear distinct. RGMa and RGMb are reported to have roles in nervous system biology, immunity, inflammation, angiogenesis, and growth, while RGMc is primarily expressed in the liver (e.g., hepatocytes), which is the major site of hepcidin synthesis, and is involved in regulating iron metabolism.

Evidence supports the notion that inhibition of the BMP6/RGMc axis may be an attractive therapeutic approach to treat iron dysregulation. For example, US2013/0330343A1 disclosed that a monoclonal antibody that binds and neutralizes RGMa/c is capable of 1) decreasing hepcidin levels, 2) increasing serum iron levels and transferrin saturation, and 3) decreasing unsaturated iron binding capacity (UIBC), in treated animals.

The inventors of the present disclosure recognized that RGMc-selective inhibition may provide improved safety profiles. It was reasoned that such inhibitors should only target the liver-expressed RGMc, while maintaining the normal biological functions of RGMa and RGMb intact. As such, the inventors sought to identify RGMc selective-antibodies that do not bind to RGMa or RGMb in order to achieve liver-specific modulation of BMP6 activity.

TABLE 1

| RGM | % Identity to hRGMc | % Homology to hRGMc | % homology in helicies |
|---|---|---|---|
| RGMa | 46 | 59 | 80 |
| RGMb | 41 | 58 | 50 |

RGMc/Hemojuvelin (HJV)

There are at least three isoforms of human RGMc, including a precursor protein (isoform a; SEQ ID NO: 1) and two splice variants (isoform b and isoform c; SEQ ID NOs: 2 and 3, respectively). Human RGMc isoform "a", the predominant isoform, consists of 426 amino acids and represents the longest transcript. Unless otherwise indicated herein, the term "RGMc" refers to a full-length protein, heterodimer, or cleavage product of RGMc isoform a. Below are the amino acid sequences of the RGMc isoforms, RGMa, and RGMb.

```
Human RGMc isoform a
(Accession No. NP_998818; SEQ ID NO: 1):
   1 mgepgqspsp rsshgsppt1 stltllll1c ghahsqckil
     rcnaeyvsst lslrgggssg
  61 alrggggggr gggvgsgglc ralrsyalct rrtartcrgd
     lafhsavhgi edlmiqhncs
 121 rqgptapppp rgpalpgags glpapdpcdy egrfsrlhgr
     ppgflhcasf gdphvrsfhh
 181 hfhtcrvqga wplldndflf vqatsspmal ganatatrkl
     tiifknmqec idqkvyqaev
 241 dnlpvafedg singgdrpgg sslsiqtanp gnhveiqaay
     igttiiirqt agqlsfsikv
 301 aedvamafsa eqdlqlcvgg cppsqrlsrs ernrrgaiti
     dtarrlckeg lpvedayfhs
 361 cvfdvlisgd pnftvaaqaa ledaraflpd leklhlfpsd
     agvplssatl lapllsglfv
 421 lwlciq
Human RGMc isoform b
(Accession No. NP_660320; SEQ ID NO: 2):
   1 miqhncsrqg ptappppgp alpgagsglp apdpcdyegr
     fsrlhgrppg flhcasfgdp
  61 hvrsfhhhfh tcrvqgawpl ldndflfvqa tsspmalgan
     atatrkltii fknmqecidq
 121 kvyqaevdnl pvafedgsin ggdrpggssl siqtanpgnh
     veiqaayigt tiiirqtagq
 181 lsfsikvaed vamafsaeqd lqlcvggcpp sqrlsrsern
     rrgaitidta rrlckeglpv
 241 edayfhscvf dvlisgdpnf tvaaqaaled araflpdlek
     lhlfpsdagv plssatllap
 301 llsglfvlwl ciq
```

```
Human RGMc isoform c
(Accession No. NP_998817; SEQ ID NO: 3):
   1 mqecidqkvy qaevdnlpva fedgsinggd rpggsslsiq
     tanpgnhvei qaayigttii
  61 irqtagqlsf sikvaedvam afsaeqdlql cvggcppsqr
     lsrsernrrg aitidtarrl
 121 ckeglpveda yfhscvfdvl lsgdpnftva aqaaledara
     flpdleklhl fpsdagvpls
 181 satllaplls glfvlwlciq
Human RGMa (Accession No.
NP_001159755; SEQ ID NO: 4):
   1 mgglgprrag tsrerlvvtg ragwmgmgrg agrsalgfwp
     tlafllcsfp aatspckilk
  61 cnsefwsats gshapasddt pefcaalrsy alctrrtart
     crgdlayhsa vhgiedlmsq
 121 hncskdgpts qprlrtlppa gdsgersdsp eichyeksfh
     khsatpnyth cglfgdphlr
 181 tftdrfqtck vqgawplidn nylnvqvtnt pvlpgsaata
     tskltiIfkn fqecvdqkvy
 241 qaemdelpaa fvdgsknggd khganslkit ekvsgqhvei
     qakyigttiv vrqvgryltf
 301 avrmpeevvn avedwdsqgl ylclrgcpin qqidfqafht
     naegtgarrl aaaspaptap
 361 etfpyetava kckeklpved lyyqacvfdl lttgdvnftl
     aayyaledvk mlhsnkdklh
 421 lyertrdlpg raaaglplap rpllgalvpl lallpvfc
Human RGMb (Accession No.
NP_001012779; SEQ ID NO: 5):
   1 mirkkrkrsa ppgpershgp rpatapappp speptrpawt
     gmglraapss aaaaaaeveq
  61 rrspglcppp lellllllfs lgllhagdcq qpaqcriqkc
     ttdfvsltsh lnsavdgfds
 121 efckalraya gctqrtskac rgnlvyhsav lgisdlmsqr
     ncskdgptss tnpevthdpc
 181 nyhshagare hrrgdqnpps ylfcglfgdp hlrtfkdnfq
     tckvegawpl idnnylsvqv
 241 tnvpvvpgss atatnkitii fkahhectdq kvyqavtddl
     paafvdgtts ggdsdakslr
 301 Iveresghyv emharyigtt vfvrqvgryl tlairmpedl
     amsyeesqdl qlcvngcpls
 361 eriddgqgqv sailghslpr tslvqawpgy tletantqch
     ekmpvkdiyf qscvfdlltt
```

```
421 gdanftaaah saledvealh prkerwhifp ssgngtprgg sdlsyslglt clilivfl
```

RGMc is a co-receptor for BMP6, which is part of a larger multimeric protein complex comprising BMP6, BMP6 binding type I and type II serine threonine kinase receptors (e.g., Alk2, Alk3, BMPR2, and ActRIIA), neogenin, RGMc (HJV), HFE, and TFR2. Binding of BMP6 to its receptors, and in turn the larger multimeric complex, induces downstream SMAD phosphorylation, which induces nuclear translocation of the transcription factors that mediate increased hepcidin transcription. Thus, BMP6 signaling has been shown to directly modulate iron homeostatis through the regulation of hepcidin expression.

RGMc is expressed in membrane-bound and soluble forms in mammals. The membrane-bound RGMc is found on the cell surface in two different forms, a single-chain full-length form, and a disulfide-linked two-chain (heterodimeric) form. The heterodimeric form of RGMc is the result of autoproteolysis occurring at a FGDPH motif producing a C-terminal fragment of about 35 kD and an N-terminal fragment of about 20 kD, which remains linked by disulfide bonds. Although it has been shown that the single-chain, full-length RGMc interacts with BMP2, previous studies suggest that autoproteolysis is important for the correct folding of the protein and that autocatalytic processing is a general and important feature of RGMs. For example, it has been shown that only the heterodimeric form of RGMc activates hepcidin expression in vitro, and RGMa autocatalytic processing is required for its growth inhibitory effect on axons. Moreover, several JHH-associated mutations are located near the RGMc autocatalytic cleavage site and these mutants have low signaling activities and are often retained in the ER.

Additionally, at least two proteases, furin and TMPRSS6, have been shown to cleave RGMc to produce several soluble forms of RGMc (s-RGMc or s-HJV). Specifically, furin cleavage produces a ~40 kD s-RGMc fragment. This fragment has been shown to act as a decoy receptor that competes with membrane-bound RGMc for binding to BMP ligands, thereby reducing hepcidin expression and increasing serum iron levels. Interestingly, furin activity has been shown to be enhanced in iron deficiency and hypoxia. However, since furin also participates in the processing of pro-hepcidin, the effect of furin on hepcidin expression may be complex, and most likely depends on the particular cellular conditions.

On the other hand, TMPRSS6 can cleave RGMc at multiple sites leading to cleavage fragments with varying functionality. The role of TMPRSS6 in regulating hepcidin expression was shown by studies demonstrating that its inactivation in mice leads to an increase in hepcidin levels, a block of iron absorption, and anemia. Moreover, iron-refractory iron deficiency anemia (IRIDA) can be caused by mutations in the gene encoding TMPRSS6/matriptase-2. However, it has also been shown that RGMc fragments shed by TMPRSS6 have reduced ability to bind BMPs.

As discussed above, hepcidin is a key regulator of the systemic iron mobilization and is in turn regulated by the bone morphogenetic protein (BMP)-mediated signaling, particularly BMP6. RGMc binds BMP6 and regulates the Smad-mediated pathway, leading to the regulation of Hepcidin expression, which in turn degradation of ferroportin, an iron transporter protein, thereby blocking iron release from macrophages and enterocytes into the circulation. Thus, increased RGMc activity likely increases hepcidin expression leading to reduced iron release from cells. In this setting, RGMc activity may cause an imbalance in iron homeostasis due to systemic iron depletion resulting in iron-related disease. In other words, an RGMc-mediated increase in hepcidin levels may result in anemia, while its decreased expression may be the causative feature in many haemochromatosis (iron-overload) diseases.

Accordingly, the present application provides RGMc-selective monoclonal antibodies and fragments thereof that specifically bind and inhibit RGMc activity in vivo, without cross-reacting with RGMa or RGMb. To the applicant's best knowledge, these antibodies and fragments represent a novel class of such inhibitors. The rationale for this approach includes the following. First, based on the recognition that the hepcidin is a key regulator of iron homeostasis, and that BMP6 is required in the process, inhibitors that block this signaling axis are desirable. Second, since BMP6 is broadly expressed and plays a diverse range of biological roles, it is advantageous to avoid direct targeting of BMP6. Because the RGM family of proteins are known to interact with and co-receptors of BMPs, such as BMP6, BMP2 and BMP4, targeting the co-receptor may provide an alternative and attractive approach to block the signaling to regulate hepcidin. Third, with the recognition, however, that RGMa and RGMb play distinct biological functions, such inhibitors should selectively inhibit RGMc, without affecting RGMa/b. In this way, selective inhibition of liver RGMc may be achieved while minimizing potential unwanted side effects that may arise from inadvertently and systemically blocking normal function of BMP6, RGMa and RGMb.

The present disclosure provides antibodies, and antigen-binding fragments thereof, that specifically bind to RGMc or RGMc-containing complex and inhibit its function but do not bind or inhibit the function of RGMa and RGMb. In some embodiments, the antibodies, and antigen-binding fragments thereof, described herein inhibit interaction of RGMc with a BMP, e.g., BMP6. In some embodiments, the antibodies or fragments described herein do not inhibit interaction of RGMc with neogenin. In any of the embodiments, the antibodies and fragments encompassed by the present invention provide exquisite specificity and targeting of the RGMc pathway. Advantageously, such antibodies or fragments may achieve decreased toxicity. Importantly, because RGMc expression is restricted to a subset of tissues, RGMc-mediated inhibition of the BMP6 pathway, as opposed to directly antagonizing BMP6 itself, or broad inhibition of the RGM family, should achieve tissue-selective effects, hence reduce toxicities stemming from systemic effects.

Thus, the present invention encompasses the recognition that the use of selective inhibitors of RGMc provides an advantageous approach for the treatment of conditions involving iron dysregulation, as compared to non-selective inhibitors. To this end, the inventors of the present disclosure sought to design and generate antibodies or fragments thereof that specifically and selectively target RGMc, without targeting RGMa or RGMb in vivo. This is based at least in part on the notion that the selectivity provides improved safety profiles (e.g., reduced toxicities or adverse effects) for in vivo administration of such inhibitors.

For example, targeting RGMc along with RGMa and/or RGMb may increase potential toxicities associated with the extensive non-liver tissue expression of RGMa/b and their known role various physiological possesses. Specifically, RGMa has been shown to be critical for embryonic development and is expressed in multiple tissues including the brain, skin, heart, liver, lung, kidney, testis, and gut of the adult mouse. Consistent with these data, approximately half of mice deficient in the RGMa gene die in utero, with an exancephalic phenotype and major morphological and developmental defects. RGMa has also been shown to play a critical role in neuronal regeneration, recovery and survival post-injury. Pathologically, elevated RGMa levels are observed in the brain lesions from injury and ischemic stroke; Alzheimer's Disease amyloid plaques; and the substantia nigra of Parkinson's Disease patients. However, reduced RGMa expression and increased promoter methylation status have been shown to be closely associated with colorectal cancer genesis and progression (Zhao et al., Oncol Rep 2012; 27(5):1653-9). These lines of evidence suggest that RGMa/c cross-reactive antibodies, for example, may cause or exacerbate cancer progression.

In addition to embryonic development and neuronal regeneration, RGMa also has been shown to regulate immune responses to injury; it is expressed by dendritic cells in brain and spinal cord lesions and modulates T cell responses. Specifically, inhibition of RGMa has been shown to suppress T cell response in a mouse model of multiple sclerosis (experimental autoimmune encephalomyelitis; EAE). In humans, RGMa inhibition reduces T cell proliferation and pro-inflammatory cytokine production in peripheral blood mononuclear cells (PBMCs). Moreover, among T cell subsets, RGMa has been shown to be highly expressed on Th17 cells. Since Th17 cells play an important role in, inter alia, host defense against infection by recruiting neutrophils and macrophages to infected tissues, pharmacological perturbation of the normal immune function is undesirable. Advantageously, by selectively targeting and inhibiting RGMc and not RGMa, such side effects can be effectively avoided.

Although many of these functions relate to injury, RGMa may also modulate neuronal regeneration in healthy individuals. Considering its important roles in regulation of CNS response to injury, immune responses and unknown roles in various organs, inhibition of RGMa activity is undesirable due to the risk of potential off-target side effects.

RGMb has also been shown to be expressed in multiple tissues including brain, bone, heart, lung, liver, kidney, testis, ovary, uterus, epididymis and pituitary in adult mouse. RGMb knockout mice die by postnatal Day 12 and are stunted in growth. RGMb, like RGMa, also has a role in the immune response. Specifically, RGMb is expressed at high levels in lung macrophages and dendritic cells. In its absence, IL-6 levels are elevated in these cell types, suggesting a role in regulating inflammation. RGMb has also been shown to promote neurite outgrowth. Recently, RGMb was described as a binding partner for PD-L2 in the lung, and blocking this interaction prevented the development of respiratory tolerance, highlighting a role for RGMb in lung immunity. It raises the possibility that inhibitors that interfere with the RGMb function may cause dysregulation of immune responses.

Moreover, it has been suggested that RGMb may act as a tumor suppressor, possibly by inhibiting SMAD activation. Indeed, reduced expression of RGMb is associated with poor prognosis in non-small cell lung carcinoma. The RGMb gene is inactivated in a subtype of colorectal cancer, and RGMb has been shown to be a negative regulator of breast cancer proliferation in vitro. Thus, not only could inhibiting RGMb have an effect on the immune and nervous systems, but such inhibition may also augment cancer progression and/or development.

In summary, the widespread expression patterns and pleiotropic functions in diverse biological processes of the related family members RGMa and RGMb are in contrast to the restricted expression pattern and focused role of RGMc in maintaining iron homeostasis. This underscores the importance of taking an RGMc-specific approach to the discovery of novel therapeutics for iron-restricted anemias without complicating off-target effects.

Thus, in one aspect, the invention is aimed to inhibit RGMc function without invoking potential side effects or toxicities associated with interfering with RGMa and RGMb activities in vivo. It is contemplated that liver-selective inhibition of BMP6 signaling through the intervention of RGMc function could provide a way to target a variety of iron-restricted anemias, including anemia of chronic kidney disease, anemia of cancer and anemia of chronic inflammation.

According to the invention, selective inhibitors of RGMc do not inhibit other closely related factors such as RGMa and RGMb. Such an inhibitor can be used to normalize iron homeostasis including for the treatment of various forms of anemia or diseases involving iron-restricted anemia. Indeed, as demonstrated herein, RGMc-specific antibodies are shown to selectively repress the Bone Morphogenetic Protein 6 (BMP6)-hepcidin axis and increase the availability of iron for erythropoiesis.

RGMc Inhibitors

To carry out the methods of the present invention, any suitable inhibitory agents of RGM/HJV may be employed, provided that the such agents inhibit or antagonize RGM with sufficient selectivity for the RGMc isoform. Preferably, such inhibitory agents of RGMc have no measurable inhibitory activities towards RGMa and RGMb at dosage that provides clinical benefits (e.g., therapeutic efficacy and acceptable toxicity profiles) when administered to human subjects.

As used herein, the term "inhibitor" refers to any agent capable of blocking or antagonizing RGMc signaling. Suitable inhibitory agents include small molecules, nucleic acid-based agents, biologics (e.g., polypeptide-based agents such as antibodies and other finding-agents), and any combinations thereof.

In some embodiments, such agents can prevent or reduce RGMc activity by inhibiting RGMc association with the BMP receptor complex. In some embodiments, such agents can prevent or reduce RGMc activity by inhibiting RGMc binding to BMP. In some embodiments, such agents can prevent or reduce RGMc activity by inhibiting RGMc binding to BMP6. In some embodiments, such agents can prevent or reduce RGMc activity by inhibiting RGMc binding to neogenin. In some embodiments, such agents are competitive inhibitors of RGMc/BMP6 binding. In some embodiments, such agents are competitive inhibitors of RGMc/neogenin binding.

In some embodiments, the inhibitor may be an antibody (including fragments thereof, such as Domain Antibodies (dAbs) as described in, for example, U.S. Pat. Nos. 6,291,158; 6,582,915; 6,593,081; 6,172,197; and 6,696,245), a small molecule inhibitor, an Adnectin®, an Affibody®, a DARPin®, an Anticalin®, an Avimer®, a Versabody® or a gene therapy. Use of inhibitors encompassed by the present invention also includes antibody mimetics, such as monobodies and single-domain antibodies. Monobodies are synthetic binding proteins that typically employ a fibronectin type III domain (FN3) as a molecular scaffold. Monobodies include Adnectins™ which are based on the 10th fibronectin type III domain.

RGMc-Specific Antibodies

Recently, monoclonal antibodies that specifically bind RGMa/RGMc were shown to increase serum iron in rats and cynomolgus monkeys by downregulating hepcidin (Boser et al. (2015) AAPS J. 2015 July; 17(4): 930-938). In this case, the investigators reported no obvious toxicities in healthy animals that received the RGMa/RGMc antibodies, and normalization of blood parameters were seen after a recovery period (~12 week) following a dosing period. However, potential risks associated with concurrent inhibition of RGMa, for example, on the nervous system, are not discernable from the published work. Moreover, numerous other toxicities are possible humans as outlined above, such as those associated with the non-hepatic cell expression of RGMa (e.g., toxicities associated with the brain, skin, heart, lung, kidney, testis, and gut). Reduced RGMa expression has also been shown to be related to colorectal cancer genesis and progression. Moreover, RGMa expression has been shown to regulate immune responses to injury. Thus, the present invention provides novel, RGMc-selective inhibitors that do not bind and inhibit RGMa and/or RGMb activity/function.

In some embodiments of the invention, the RGMc-selective inhibitors (e.g., antibodies) inhibit or reduce interaction of RGMc with BMPs. In another embodiment, the RGMc-selective inhibitors (e.g., antibodies) inhibit or reduce RGMc interaction with BMP6. In another embodiment, the RGMc-selective inhibitors do not inhibit or reduce interaction with neogenin.

In some embodiment, the RGMc-selective inhibitors (e.g., antibodies) modulate interaction of RGMc with one or more of the following interacting proteins; HFE, TFR2, ALK2, ALK3, BMPR2, ACVR2A and TMPRSS6. In another embodiment, the RGMc-selective inhibitors (e.g., antibodies) inhibit interaction of RGMc with one or more of the following interacting proteins; HFE, TFR2, ALK2, ALK3, BMPR2, ACVR2A and TMPRSS6. In another embodiment, the RGMc-selective inhibitors (e.g., antibodies) inhibit interaction of RGMc with HFE. In another embodiment, the RGMc-selective inhibitors (e.g., antibodies) inhibit interaction of RGMc with TFR2. In another embodiment, the RGMc-selective inhibitors (e.g., antibodies) inhibit interaction of RGMc with ALK2. In another embodiment, the RGMc-selective inhibitors (e.g., antibodies) inhibit interaction of RGMc with ALK3. In another embodiment, the RGMc-selective inhibitors (e.g., antibodies) inhibit interaction of RGMc with BMPR2. In another embodiment, the RGMc-selective inhibitors (e.g., antibodies) inhibit interaction of RGMc with ACVR2A. In another embodiment, the RGMc-selective inhibitors (e.g., antibodies) inhibit interaction of RGMc with TMPRSS6.

In some embodiments, the RGMc comprises a naturally occurring mammalian amino acid sequence. In some embodiment, the RGMc comprises a naturally occurring human amino acid sequence. In some embodiments, the RGMc comprises a human, a monkey, a rat or a mouse amino acid sequence. In some embodiments, the RGMc is a human RGMc sequence, or a fragment thereof, as set forth in SEQ ID NO: 1. In some embodiments, the RGMa is a soluble form of RGMc.

In some embodiment, the RGMc-selective inhibitors bind to RGMc with a $K_D$ of ≤5 nM (e.g., ≤0.1 nM) in a suitable in vitro binding assay, such as Octet® or MSD. On the other hand, unlike RGMc antibodies previously described, these RGMc-specific antibodies do not show any detectable binding to RGMa, or RGMb under the same assay conditions. For example, the RGMc-selective inhibitors may bind to RGMc with a $K_D$ of ≤0.1 nM, but do not show any detectable binding to RGMa or RGMb by MSD under the same assay conditions.

In some embodiments, the RGMa comprises a naturally occurring mammalian amino acid sequence. In some embodiment, the RGMa comprises a naturally occurring human amino acid sequence. In some embodiments, the RGMa comprises a human, a monkey, a rat or a mouse amino acid sequence. In some embodiments, the RGMa is a human RGMa sequence, or a fragment thereof, as set forth in SEQ ID NO: 4. In some embodiments, the RGMa is a soluble form of RGMa.

In some embodiments, the RGMb comprises a naturally occurring mammalian amino acid sequence. In some embodiment, the RGMb comprises a naturally occurring human amino acid sequence. In some embodiments, the RGMb comprises a human, a monkey, a rat or a mouse amino acid sequence. In some embodiments, the RGMb is a human RGMb sequence, or a fragment thereof, as set forth in SEQ ID NO: 5. In some embodiments, the RGMb is a soluble form of RGMb.

Aspects of the invention relate to an isolated monoclonal antibody, or antigen-binding fragment thereof, that binds selectively to a RGMc and comprises six complementarity-determining regions (CDRs): CDRH1, CDRH2, CDRH3, CDRL1, CDRL2, and CDRL3.

In one aspect, the antibodies, or antigen-binding fragments thereof, that bind selectively to RGMc and have one or more CDR sequences substantially similar to CDRH1, CDRH2, CDRH3, CDRL1, CDRL2, and/or CDRL3 as compared to a corresponding CDR region. For example, the antibodies may include one or more CDR sequences (e.g., SEQ ID NOs: 6-11, SEQ ID NOs: 14-19, SEQ ID NOs: 22-27, SEQ ID NOs: 30-35, or SEQ ID NOs: 38-43) each containing up to 1, 2, 3, 4, or, 5 amino acid residue variations as compared to the corresponding CDR region in any one of SEQ ID NOs: 6-11, SEQ ID NOs: 14-19, SEQ ID NOs: 22-27, SEQ ID NOs: 30-35, or SEQ ID NOs: 38-43.

As used herein, the phrase "amino acid variations" or "amino acid changes" or "changes in amino acid residues" includes amino acid substitutions and/or deletions.

In one embodiment, the antibody, or antigen-binding fragment thereof, comprises at least three CDRs selected from the following, optionally comprising up to 3 amino acid changes, for example 1, 2, or 3 amino acid changes for each of the CDRs: CDR-H1: SEQ ID NO: 6; CDR-H2: SEQ ID NO: 7; CDR-H3: SEQ ID NO: 8; CDR-LL: SEQ ID NO: 9; CDR-L2: SEQ ID NO: 10; and, CDR-L3: SEQ ID NO: 11.

In one embodiment, the antibody, or antigen-binding fragment thereof, comprises at least three CDRs selected from the following, optionally comprising up to 3 amino acid changes, for example 1, 2, or 3 amino acid changes for each of the CDRs: CDR-H1: SEQ ID NO: 14; CDR-H2: SEQ ID NO: 15; CDR-H3: SEQ ID NO: 16; CDR-L1: SEQ ID NO: 17; CDR-L2: SEQ ID NO: 18; and, CDR-L3: SEQ ID NO: 19.

In one embodiment, the antibody, or antigen-binding fragment thereof, comprises at least three CDRs selected from the following, optionally comprising up to 3 amino acid changes, for example 1, 2, or 3 amino acid changes for each of the CDRs: CDR-H1: SEQ ID NO: 22; CDR-H2: SEQ ID NO: 23; CDR-H3: SEQ ID NO: 24; CDR-L1: SEQ ID NO: 25; CDR-L2: SEQ ID NO: 26; and, CDR-L3: SEQ ID NO: 27.

In one embodiment, the antibody, or antigen-binding fragment thereof, comprises at least three (e.g., 3, 4, 5 or preferably all 6) CDRs selected from the following, optionally comprising up to 3 amino acid changes, for example 1, 2, or 3 amino acid changes for each of the CDRs: CDR-H1: SEQ ID NO: 30; CDR-H2: SEQ ID NO: 31; CDR-H3: SEQ ID NO: 32; CDR-L1: SEQ ID NO: 33; CDR-L2: SEQ ID NO: 34; and, CDR-L3: SEQ ID NO: 35.

In one embodiment, the antibody, or antigen-binding fragment thereof, comprises at least three CDRs selected from the following, optionally comprising up to 3 amino acid changes, for example 1, 2, or 3 amino acid changes for each of the CDRs: CDR-H1: SEQ ID NO: 38; CDR-H2: SEQ ID NO: 39; CDR-H3: SEQ ID NO: 40; CDR-L1: SEQ ID NO: 41; CDR-L2: SEQ ID NO: 42; and, CDR-L3: SEQ ID NO: 43.

In another aspect, the invention provides an antibody, or antigen-binding fragment thereof comprising a heavy chain variable region comprising a CDR-H1, CDR-H2, and/or CDR-H3 having particular amino acid changes.

In some embodiments, the antibody or antigen-binding fragment thereof, comprises a CDR-H1 as set forth in SEQ ID NO: 14, with the proviso that the serine residue at position 4 of SEQ ID NO: 14 may be substituted with an arginine. In another embodiment, the antibody or antigen-binding fragment thereof, comprises a CDR-H1 as set forth in SEQ ID NO: 14, with the proviso that the alanine residue at position 7 of SEQ ID NO: 14 may be substituted with a serine. In another embodiment, the antibody or antigen-binding fragment thereof, comprises a CDR-H1 as set forth in SEQ ID NO: 14, with the proviso that the serine residue at position 9 of SEQ ID NO: 14 may be substituted with a glutamine. In some embodiments, the antibody or antigen-binding fragment thereof, comprises a CDR-H1 as set forth in SEQ ID NO: 14, with the proviso that (i) the serine residue at position 4 of SEQ ID NO: 14 may be substituted with an arginine; (ii) the alanine residue at position 7 of SEQ ID NO: 14 may be substituted with a serine; and/or (ii) the serine residue at position 9 of SEQ ID NO: 14 may be substituted with a glutamine.

In some embodiment, the antibody or antigen-binding fragment thereof, comprises a CDR-H2 as set forth in SEQ ID NO: 15, with the proviso that the threonine residue at position 8 of SEQ ID NO: 15 may be substituted with a valine. In another embodiment, the antibody or antigen-binding fragment thereof, comprises and CDR-H2 as set forth in SEQ ID NO: 15, with the proviso that the asparagine residue at position 10 of SEQ ID NO: 15 may be substituted with a serine. In some embodiments, the antibody or antigen-binding fragment thereof, comprises a CDR-H2 as set forth in SEQ ID NO: 15, with the proviso that (i) the threonine residue at position 8 of SEQ ID NO: 15 may be substituted with a valine; and/or (ii) the asparagine residue at position 10 of SEQ ID NO: 15 may be substituted with a serine.

In some embodiments, the antibody or antigen-binding fragment thereof, comprises a CDR-H3 as set forth in SEQ ID NO: 16, with the proviso that the isoleucine residue at position 5 of SEQ ID NO: 16 may be substituted with a tyrosine. In another embodiment, the antibody or antigen-binding fragment thereof, comprises and CDR-H3 as set forth in SEQ ID NO: 16, with the proviso that the alanine residue at position 6 of SEQ ID NO: 16 may be substituted with a valine. In some embodiments, the antibody or antigen-binding fragment thereof, comprises a CDR-H3 as set forth in SEQ ID NO: 16, with the proviso that (i) the isoleucine residue at position 5 of SEQ ID NO: 16 may be substituted with a tyrosine; and/or (ii) the alanine residue at position 6 of SEQ ID NO: 16 may be substituted with a valine.

In some embodiments, the antibody or antigen-binding fragment thereof, comprises a CDR-L1 as set forth in SEQ ID NO 17, optionally comprising up to 3 amino acid changes. In some embodiments, the antibody or antigen-binding fragment thereof, comprises a CDR-L2 as set forth in SEQ ID NO 18, optionally comprising up to 3 amino acid changes. In some embodiments, the antibody or antigen-binding fragment thereof, comprises a CDR-L3 as set forth in SEQ ID NO 19, optionally comprising up to 3 amino acid changes.

In a particular embodiment, the invention provides an isolated antibody that specifically binds human RGMc, wherein the antibody is a full-length antibody or antigen-binding fragment thereof, and wherein the antibody comprises at least three of the following six CDRs:
 a) CDR-H1: SEQ ID NO: 14, with the proviso that:
  i) the serine residue at position 4 of SEQ ID NO: 14 may be substituted with an arginine;
  ii) the alanine residue at position 7 of SEQ ID NO: 14 may be substituted with a serine; and/or
  iii) the serine residue at position 9 of SEQ ID NO: 14 may be substituted with a glutamine;
 b) CDR-H2: SEQ ID NO: 15, with the proviso that:
  i) the threonine residue at position 8 of SEQ ID NO: 15 may be substituted with a valine; and/or
  ii) the asparagine residue at position 10 of SEQ ID NO: 15 may be substituted with a serine;
 c) CDR-H3: SEQ ID NO: 16, with the proviso that:
  i) the isoleucine residue at position 5 of SEQ ID NO: 16 may be substituted with a tyrosine; and/or
  ii) the alanine residue at position 6 of SEQ ID NO: 16 may be substituted with a valine;
 d) CDR-L1: SEQ ID NO: 17;
 e) CDR-L2: SEQ ID NO: 18; and
 f) CDR-L3: SEQ ID NO: 19.

In some embodiments, such antibody binds human RGMc with a $K_D$ of <1 nM (preferably <0.1 nM) as measured in a suitable in vitro binding assay such as Octet® or MSD. In preferred embodiments, such antibody is also isoform-specific in that it selectively binds and inhibits the activity of RGMc and does not bind and inhibit the activity of RGMa and RGMb.

In some embodiments, the heavy chain CDR and/or the light chain CDR sequences do not comprise any amino acid changes. In some embodiments, the antibody or antigen-binding fragment thereof, comprises a CDR-H1 comprising a sequence as set forth in SEQ ID NO: 6. In some embodiments, the antibody or antigen-binding fragment thereof, comprises a CDR-H2 comprising a sequence as set forth in SEQ ID NO: 7. In some embodiments, the antibody or antigen-binding fragment thereof, comprises a CDR-H3 comprising a sequence as set forth in SEQ ID NO: 8. In some embodiments, the antibody or antigen-binding fragment thereof, comprises a CDR-L1 comprising a sequence as set forth in SEQ ID NO: 9. In some embodiments, the antibody or antigen-binding fragment thereof, comprises a CDR-L2 comprising a sequence as set forth in SEQ ID NO: 10. In some embodiments, the antibody or antigen-binding fragment thereof, comprises a CDR-L3 comprising a sequence as set forth in SEQ ID NO: 11.

In some embodiments, the antibody or antigen-binding fragment thereof, comprises a heavy chain variable region comprising a CDR-H3 having the amino acid sequence of SEQ ID NO: 8 and a light chain variable region comprising a CDR-L3 having the amino acid sequence of SEQ ID NO: 11. In some embodiments, the antibody, or antigen-binding fragment thereof, comprises a heavy chain variable region comprising a CDR-H2 having the amino acid sequence of SEQ ID NO: 7 and a light chain variable region comprising a CDR-L2 having the amino acid sequence of SEQ ID NO: 10. In some embodiments, the antibody, or antigen-binding fragment thereof, comprises a heavy chain variable region comprising a CDR-H1 having the amino acid sequence of SEQ ID NO: 6 and a light chain variable region comprising a CDR-L1 having the amino acid sequence of SEQ ID NO: 9.

In a particular embodiment, the antibody or antigen-binding fragment thereof, comprises the heavy chain CDR-H1, CDR-H2, and CDR-H3 sequences as set forth in SEQ ID NOs: 6, 7, and 8, respectively, and light chain CDR-L1, CDR-L2, and CDR-L3 sequences as set forth in SEQ ID NOs: 9, 10, and 11, respectively.

In some embodiments, the antibody or antigen-binding fragment thereof, comprises a CDR-H1 comprising a sequence as set forth in SEQ ID NO: 14. In some embodiments, the antibody or antigen-binding fragment thereof, comprises a CDR-H2 comprising a sequence as set forth in SEQ ID NO: 15. In some embodiments, the antibody or antigen-binding fragment thereof, comprises a CDR-H3 comprising a sequence as set forth in SEQ ID NO: 16. In some embodiments, the antibody or antigen-binding fragment thereof, comprises a CDR-L1 comprising a sequence as set forth in SEQ ID NO: 17. In some embodiments, the antibody or antigen-binding fragment thereof, comprises a CDR-L2 comprising a sequence as set forth in SEQ ID NO: 18. In some embodiments, the antibody or antigen-binding fragment thereof, comprises a CDR-L3 comprising a sequence as set forth in SEQ ID NO: 19.

In some embodiments, the antibody or antigen-binding fragment thereof, comprises a heavy chain variable region comprising a CDR-H3 having the amino acid sequence of SEQ ID NO: 16 and a light chain variable region comprising a CDR-L3 having the amino acid sequence of SEQ ID NO: 19. In some embodiments, the antibody, or antigen-binding fragment thereof, comprises a heavy chain variable region comprising a CDR-H2 having the amino acid sequence of SEQ ID NO: 15 and a light chain variable region comprising a CDR-L2 having the amino acid sequence of SEQ ID NO: 18. In some embodiments, the antibody, or antigen-binding fragment thereof, comprises a heavy chain variable region comprising a CDR-H1 having the amino acid sequence of SEQ ID NO: 14 and a light chain variable region comprising a CDR-L1 having the amino acid sequence of SEQ ID NO: 17.

In a particular embodiment, the antibody or antigen-binding fragment thereof, comprises the heavy chain CDR-H1, CDR-H2, and CDR-H3 sequences as set forth in SEQ ID NOs: 14, 15, and 16, respectively, and light chain CDR-L1, CDR-L2, and CDR-L3 sequences as set forth in SEQ ID NOs: 17, 18, and 19, respectively.

In some embodiments, the antibody or antigen-binding fragment thereof, comprises a CDR-H1 comprising a sequence as set forth in SEQ ID NO: 22. In some embodiments, the antibody or antigen-binding fragment thereof, comprises a CDR-H2 comprising a sequence as set forth in SEQ ID NO: 23. In some embodiments, the antibody or antigen-binding fragment thereof, comprises a CDR-H3 comprising a sequence as set forth in SEQ ID NO: 24. In some embodiments, the antibody or antigen-binding fragment thereof, comprises a CDR-L1 comprising a sequence as set forth in SEQ ID NO: 25. In some embodiments, the antibody or antigen-binding fragment thereof, comprises a CDR-L2 comprising a sequence as set forth in SEQ ID NO: 26. In some embodiments, the antibody or antigen-binding fragment thereof, comprises a CDR-L3 comprising a sequence as set forth in SEQ ID NO: 27.

In some embodiments, the antibody or antigen-binding fragment thereof, comprises a heavy chain variable region comprising a CDR-H3 having the amino acid sequence of SEQ ID NO: 24 and a light chain variable region comprising a CDR-L3 having the amino acid sequence of SEQ ID NO: 27. In some embodiments, the antibody, or antigen-binding fragment thereof, comprises a heavy chain variable region comprising a CDR-H2 having the amino acid sequence of SEQ ID NO: 23 and a light chain variable region comprising a CDR-L2 having the amino acid sequence of SEQ ID NO: 26. In some embodiments, the antibody, or antigen-binding fragment thereof, comprises a heavy chain variable region comprising a CDR-H1 having the amino acid sequence of SEQ ID NO: 22 and a light chain variable region comprising a CDR-L1 having the amino acid sequence of SEQ ID NO: 25.

In a particular embodiment, the antibody or antigen-binding fragment thereof, comprises the heavy chain CDR-H1, CDR-H2, and CDR-H3 sequences as set forth in SEQ ID NOs: 22, 23, and 24, respectively, and light chain CDR-L1, CDR-L2, and CDR-L3 sequences as set forth in SEQ ID NOs: 25, 26, and 27, respectively.

In some embodiments, the antibody or antigen-binding fragment thereof, comprises a CDR-H1 comprising a sequence as set forth in SEQ ID NO: 30. In some embodiments, the antibody or antigen-binding fragment thereof, comprises a CDR-H2 comprising a sequence as set forth in SEQ ID NO: 31. In some embodiments, the antibody or antigen-binding fragment thereof, comprises a CDR-H3 comprising a sequence as set forth in SEQ ID NO: 32. In some embodiments, the antibody or antigen-binding fragment thereof, comprises a CDR-L1 comprising a sequence as set forth in SEQ ID NO: 33. In some embodiments, the antibody or antigen-binding fragment thereof, comprises a CDR-L2 comprising a sequence as set forth in SEQ ID NO: 34. In some embodiments, the antibody or antigen-binding fragment thereof, comprises a CDR-L3 comprising a sequence as set forth in SEQ ID NO: 35.

In some embodiments, the antibody or antigen-binding fragment thereof, comprises a heavy chain variable region comprising a CDR-H3 having the amino acid sequence of SEQ ID NO: 32 and a light chain variable region comprising a CDR-L3 having the amino acid sequence of SEQ ID NO: 35. In some embodiments, the antibody, or antigen-binding fragment thereof, comprises a heavy chain variable region comprising a CDR-H2 having the amino acid sequence of SEQ ID NO: 31 and a light chain variable region comprising a CDR-L2 having the amino acid sequence of SEQ ID NO: 34. In some embodiments, the antibody, or antigen-binding fragment thereof, comprises a heavy chain variable region comprising a CDR-H1 having the amino acid sequence of SEQ ID NO: 30 and a light chain variable region comprising a CDR-L1 having the amino acid sequence of SEQ ID NO: 33.

In a particular embodiment, the antibody or antigen-binding fragment thereof, comprises the heavy chain CDR-H1, CDR-H2, and CDR-H3 sequences as set forth in SEQ ID NOs: 30, 31, and 32, respectively, and light chain CDR-L1, CDR-L2, and CDR-L3 sequences as set forth in SEQ ID NOs: 33, 34, and 35, respectively.

In some embodiments, the antibody or antigen-binding fragment thereof, comprises a CDR-H1 comprising a sequence as set forth in SEQ ID NO: 38. In some embodiments, the antibody or antigen-binding fragment thereof, comprises a CDR-H2 comprising a sequence as set forth in SEQ ID NO: 39. In some embodiments, the antibody or antigen-binding fragment thereof, comprises a CDR-H3 comprising a sequence as set forth in SEQ ID NO: 40. In some embodiments, the antibody or antigen-binding fragment thereof, comprises a CDR-L1 comprising a sequence as set forth in SEQ ID NO: 41. In some embodiments, the antibody or antigen-binding fragment thereof, comprises a CDR-L2 comprising a sequence as set forth in SEQ ID NO: 42. In some embodiments, the antibody or antigen-binding fragment thereof, comprises a CDR-L3 comprising a sequence as set forth in SEQ ID NO: 43.

In some embodiments, the antibody or antigen-binding fragment thereof, comprises a heavy chain variable region comprising a CDR-H3 having the amino acid sequence of SEQ ID NO: 40 and a light chain variable region comprising a CDR-L3 having the amino acid sequence of SEQ ID NO: 43. In some embodiments, the antibody, or antigen-binding fragment thereof, comprises a heavy chain variable region comprising a CDR-H2 having the amino acid sequence of SEQ ID NO: 39 and a light chain variable region comprising a CDR-L2 having the amino acid sequence of SEQ ID NO: 42. In some embodiments, the antibody, or antigen-binding fragment thereof, comprises a heavy chain variable region comprising a CDR-H1 having the amino acid sequence of SEQ ID NO: 38 and a light chain variable region comprising a CDR-L1 having the amino acid sequence of SEQ ID NO: 41.

In a particular embodiment, the antibody or antigen-binding fragment thereof, comprises the heavy chain CDR-H1, CDR-H2, and CDR-H3 sequences as set forth in SEQ ID NOs: 38, 39, and 40, respectively, and light chain CDR-L1, CDR-L2, and CDR-L3 sequences as set forth in SEQ ID NOs: 41, 42, and 43, respectively.

Aspects of the invention relate to a monoclonal antibody, or antigen-binding fragment thereof, that binds selectively to RGMc, and that comprises a heavy chain variable region sequence and a light chain variable region sequence.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 12, SEQ ID NO: 20, SEQ ID NO: 28, SEQ ID NO: 36, or SEQ ID NO: 44. In one embodiment, the antibody, or antigen-binding fragment thereof, comprises a light chain variable region having an amino acid sequence that is at least 90%, 91%, 92%, 93%, 94%, 95%, 96%, 97%, 98% or 99% identical to SEQ ID NO: 13, SEQ ID NO: 21, SEQ ID NO: 29, SEQ ID NO: 37, or SEQ ID NO: 45.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 12 and/or a light chain variable region having an amino acid sequence that is at least 90%, 91%, 92%, 93%, 94%, 95%, 96%, 97%, 98% or 99% identical to SEQ ID NO: 13. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 12 or a light chain variable region having an amino acid sequence that is at least 90%, 91%, 92%, 93%, 94%, 95%, 96%, 97%, 98% or 99% identical to SEQ ID NO: 13. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 12 and a light chain variable region having an amino acid sequence that is at least 90%, 91%, 92%, 93%, 94%, 95%, 96%, 97%, 98% or 99% identical to SEQ ID NO: 13.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 20 and/or a light chain variable region having an amino acid sequence that is at least 90%, 91%, 92%, 93%, 94%, 95%, 96%, 97%, 98% or 99% identical to SEQ ID NO: 21. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 20 or a light chain variable region having an amino acid sequence that is at least 90%, 91%, 92%, 93%, 94%, 95%, 96%, 97%, 98% or 99% identical to SEQ ID NO: 21. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 20 and a light chain variable region having an amino acid sequence that is at least 90%, 91%, 92%, 93%, 94%, 95%, 96%, 97%, 98% or 99% identical to SEQ ID NO: 21.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 28 and/or a light chain variable region having an amino acid sequence that is at least 90%, 91%, 92%, 93%, 94%, 95%, 96%, 97%, 98% or 99% identical to SEQ ID NO: 29. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 28 or a light chain variable region having an amino acid sequence that is at least 90%, 91%, 92%, 93%, 94%, 95%, 96%, 97%, 98% or 99% identical to SEQ ID NO: 29. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 28 and a light chain variable region having an amino acid sequence that is at least 90%, 91%, 92%, 93%, 94%, 95%, 96%, 97%, 98% or 99% identical to SEQ ID NO: 29.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 36 and/or a light chain variable region having an amino acid sequence that is at least 90%, 91%, 92%, 93%, 94%, 95%, 96%, 97%, 98% or 99% identical to SEQ ID NO: 37. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 36 or a light chain variable region having an amino acid sequence that is at least 90%, 91%, 92%, 93%, 94%, 95%, 96%, 97%, 98% or 99% identical to SEQ ID NO: 37. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 36 and a light chain variable region having an amino acid sequence that is at least 90%, 91%, 92%, 93%, 94%, 95%, 96%, 97%, 98% or 99% identical to SEQ ID NO: 37.

In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 44 and/or a light chain variable region having an amino acid sequence that is at least 90%, 91%, 92%, 93%, 94%, 95%, 96%, 97%, 98% or 99% identical to SEQ ID NO: 45. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 44 or a light chain variable region having an amino acid sequence that is at least 90%, 91%, 92%, 93%, 94%, 95%, 96%, 97%, 98% or 99% identical to SEQ ID NO: 45. In one embodiment, the antibody, or antigen-binding fragment thereof, comprises a heavy chain variable region having an amino acid sequence that is at least 90%, 91%, 92%, 93%, 94%, 95%, 96%, 97%, 98% or 99% identical to SEQ ID NO: 44 and a light chain variable region having an amino acid sequence that is at least 90%, 91%, 92%, 93%, 94%, 95%, 96%, 97%, 98% or 99% identical to SEQ ID NO: 45.

In some embodiments, the heavy chain variable region and/or the light chain variable region sequences do not vary within any of the CDR sequences provided herein. For example, in some embodiments, the degree of sequence variation (e.g., 80%, 81%, 82%, 83%, 84%, 85%, 86%, 87%, 88%, 89%, 90%, 91%, 92%, 93%, 94%, 95%, 96%, 97%, 98%, or 99%) may occur within a heavy chain variable and/or a light chain variable amino acid sequence excluding any of the CDR sequences provided herein.

In some embodiments, the antibody or antigen-binding fragment thereof, comprises a heavy chain variable domain comprising an amino acid sequence set forth in SEQ ID NO: 12 and/or a light chain variable domain comprising an amino acid sequence set forth in SEQ ID NO: 13. In some embodiments, the antibody, or antigen-binding fragment thereof, comprises a heavy chain variable domain comprising an amino acid sequence set forth in SEQ ID NO: 12 or a light chain variable domain comprising an amino acid sequence set forth in SEQ ID NO: 13. In some embodiments, the antibody, or antigen-binding fragment thereof, comprises a heavy chain variable domain comprising an amino acid sequence set forth in SEQ ID NO: 12 and a light chain variable domain comprising an amino acid sequence set forth in SEQ ID NO: 13.

In some embodiments, the antibody or antigen-binding fragment thereof, comprises a heavy chain variable domain comprising an amino acid sequence set forth in SEQ ID NO: 20 and/or a light chain variable domain comprising an amino acid sequence set forth in SEQ ID NO: 21. In some embodiments, the antibody, or antigen-binding fragment thereof, comprises a heavy chain variable domain comprising an amino acid sequence set forth in SEQ ID NO: 20 or a light chain variable domain comprising an amino acid sequence set forth in SEQ ID NO: 21. In some embodiments, the antibody, or antigen-binding fragment thereof, comprises a heavy chain variable domain comprising an amino acid sequence set forth in SEQ ID NO: 20 and a light chain variable domain comprising an amino acid sequence set forth in SEQ ID NO: 21.

In some embodiments, the antibody or antigen-binding fragment thereof, comprises a heavy chain variable domain comprising an amino acid sequence set forth in SEQ ID NO: 28 and/or a light chain variable domain comprising an amino acid sequence set forth in SEQ ID NO: 29. In some embodiments, the antibody, or antigen-binding fragment thereof, comprises a heavy chain variable domain comprising an amino acid sequence set forth in SEQ ID NO: 28 or a light chain variable domain comprising an amino acid sequence set forth in SEQ ID NO: 29. In some embodiments, the antibody, or antigen-binding fragment thereof, comprises a heavy chain variable domain comprising an amino acid sequence set forth in SEQ ID NO: 28 and a light chain variable domain comprising an amino acid sequence set forth in SEQ ID NO: 29.

In some embodiments, the antibody or antigen-binding fragment thereof, comprises a heavy chain variable domain comprising an amino acid sequence set forth in SEQ ID NO: 36 and/or a light chain variable domain comprising an amino acid sequence set forth in SEQ ID NO: 37. In some embodiments, the antibody, or antigen-binding fragment thereof, comprises a heavy chain variable domain comprising an amino acid sequence set forth in SEQ ID NO: 36 or a light chain variable domain comprising an amino acid sequence set forth in SEQ ID NO: 37. In some embodiments, the antibody, or antigen-binding fragment thereof, comprises a heavy chain variable domain comprising an amino acid sequence set forth in SEQ ID NO: 36 and a light chain variable domain comprising an amino acid sequence set forth in SEQ ID NO: 37.

In some embodiments, the antibody or antigen-binding fragment thereof, comprises a heavy chain variable domain comprising an amino acid sequence set forth in SEQ ID NO: 44 and/or a light chain variable domain comprising an amino acid sequence set forth in SEQ ID NO: 45. In some embodiments, the antibody, or antigen-binding fragment thereof, comprises a heavy chain variable domain comprising an amino acid sequence set forth in SEQ ID NO: 44 or a light chain variable domain comprising an amino acid sequence set forth in SEQ ID NO: 45. In some embodiments, the antibody, or antigen-binding fragment thereof, comprises a heavy chain variable domain comprising an amino acid sequence set forth in SEQ ID NO: 44 and a light chain variable domain comprising an amino acid sequence set forth in SEQ ID NO: 45.

In some embodiments, the "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In any of the antibodies or antigen-binding fragments described herein, one or more conservative mutations can be introduced into the CDRs or framework sequences at positions where the residues are not likely to be involved in an antibody-antigen interaction. In some embodiments, such conservative mutation(s) can be introduced into the CDRs or framework sequences at position(s) where the residues are not likely to be involved in interacting with a RGMc, as determined based on the crystal structure. In some embodiments, the likely interface (e.g., residues involved in an antigen-antibody interaction) may be deduced from known structural information on other antigens sharing structural similarities.

As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the antibodies provided herein comprise mutations that confer desirable properties to the antibodies. For example, to avoid potential complications due to Fab-arm exchange, which is known to occur with native IgG4 mAbs, the antibodies provided herein may comprise a stabilizing 'Adair' mutation (Angal et al., "A single amino acid substitution abolishes the heterogeneity of chimeric mouse/human (IgG4) antibody," *Mol Immunol* 30, 105-108; 1993), where serine 228 (EU numbering; residue 241 Kabat numbering) is converted to proline resulting in an IgG1-like (CPPCP (SEQ ID NO: 48)) hinge sequence. Accordingly, any of the antibodies may include a stabilizing 'Adair' mutation or the amino acid sequence CPPCP (SEQ ID NO: 48). In one embodiment, an antibody described herein comprises a heavy chain immunoglobulin constant domain of a human IgG4 having a backbone substitution of Ser to Pro, that produces an $IgG_1$-like hinge and permits formation of inter-chain disulfide bonds.

Antibodies of this disclosure that selectively bind to RGMc may optionally comprise antibody constant regions or parts thereof. For example, a $V_L$ domain may be attached at its C-terminal end to a light chain constant domain such as Cκ or Cλ. Similarly, a $V_H$ domain or fragment thereof may be attached to all or part of a heavy chain such as IgA, IgD, IgE, IgG, and IgM, and any isotype subclass. Antibodies may include suitable constant regions (see, for example, Kabat et al., Sequences of Proteins of Immunological Interest, No. 91-3242, National Institutes of Health Publications, Bethesda, Md. (1991)). Therefore, antibodies within the scope of this may disclosure include $V_H$ and $V_L$ domains, or antigen-binding fragments thereof, combined with any suitable constant region. In exemplary embodiments, the antibodies, or antigen-binding fragments thereof, comprise a heavy chain immunoglobulin constant domain containing all or a fragment of a human $IgG_1$ or a human $IgG_4$ constant domain. In some embodiments, the antibody, or antigen-binding fragment thereof, comprises a light chain immunoglobulin constant domain containing all or a fragment of a human Ig lambda constant domain or a human Ig kappa constant domain.

In some embodiments, antibodies that selectively bind to RGMc may or may not include the framework region of the antibodies disclosed herein. In some embodiments, antibodies that selectively bind to RGMc are murine antibodies and include murine framework region sequences. In other embodiments, the antibodies are chimeric antibodies, or antigen-binding fragments thereof. In another embodiment, the antibodies are humanized antibodies, or antigen-binding fragments thereof. In another embodiment, the antibodies are fully human antibodies, or antigen-binding fragments thereof. In one embodiment, the antibody comprises a framework region comprising a human germline amino acid sequence.

The antibodies, and antigen-binding fragments thereof, described herein can have any configuration suitable for binding antigen. For example, in one embodiment, the antibody, or antigen-binding fragment thereof, comprises four polypeptide chains, including two heavy chain variable regions and two light chain variable regions. In another embodiment, the antibody, or antigen-binding fragment thereof, comprises one heavy chain variable region and one light chain variable region. In exemplary embodiments, the antibody, or antigen-binding fragment thereof, is a Fab fragment, a F(ab')$_2$ fragment, a scFab fragment, an scFv, or a diabody.

In one embodiment, the antibody, or antigen-binding fragment thereof, comprises a heavy chain immunoglobulin constant domain of a human $IgG_1$ constant domain or a human $IgG_4$ constant domain. In an exemplary embodiment, the heavy chain immunoglobulin constant domain is a human $IgG_4$ constant domain. In one embodiment, the antibody, or antigen-binding fragment thereof, binds a conformational epitope. In one embodiment, the antibody, or antigen-binding fragment thereof, binds a combinatorial or discontinuous epitope.

In one embodiment, the antibody, or antigen-binding fragment thereof, comprises a heavy chain immunoglobulin constant domain of a human $IgG_4$ constant domain having a backbone substitution of Ser to Pro that produces an $IgG_1$-like hinge and permits formation of inter-chain disulfide bonds. In one embodiment, the antibody, or antigen-binding fragment thereof, further comprises a light chain immunoglobulin constant domain comprising a human Ig lambda constant domain, or a human Ig kappa constant domain.

In one embodiment, the antibody is an IgG having four polypeptide chains which are two heavy chains and two light chains. In exemplary embodiments, the antibody can be a humanized antibody, a human antibody, or a chimeric antibody. In one embodiment, the antibody comprises a framework having a human germline amino acid sequence.

In one embodiment, the invention provides an antibody, or antigen-binding fragment thereof, that competes for binding with an antibody, or antigen-binding fragment thereof, described herein. In one embodiment, the invention provides an antibody, or antigen-binding fragment thereof, that binds to the same epitope as an antibody, or antigen-binding fragment thereof, described herein.

In another aspect of the invention, a class of RGMc-specific antibodies is provided, each of which do not bind to RGMa and/or RGMb. Such antibodies which specifically bind RGMc (such as the antibodies described herein) bind with a $K_D$ of ≤5 nM (e.g., ≤5 nM, ≤4 nM, ≤3 nM, ≤2 nM, ≤1 nM, ≤0.5 nM, ≤0.1 nM, and ≤0.05 nM). In one embodiment, the antibody binds to human RGMc with a $K_D$ of ≤5 nM. In another embodiment, the antibody binds to human RGMc with a $K_D$ of ≤4 nM. In another embodiment, the antibody binds to human RGMc with a $K_D$ of ≤3 nM. In another embodiment, the antibody binds to human RGMc with a $K_D$ of ≤2 nM. In another embodiment, the antibody binds to human RGMc with a $K_D$ of ≤1 nM. In another embodiment, the antibody binds to human RGMc with a $K_D$ of ≤0.5 nM. In another embodiment, the antibody binds to human RGMc with a $K_D$ of ≤0.1 nM. In another embodiment, the antibody binds to human RGMc with a $K_D$ of ≤0.05 nM. The art is familiar with suitable techniques and assays that may be employed to determine in vitro binding activities.

In preferred embodiments, suitable means of measuring affinities of an antibody to its antigen(s) include but are not limited to the so called biolayer Interferometry (BLI) technique and surface plasmon resonance (SPR)-based assays. The former includes Octet® systems and the latter includes Biacore systems. In another embodiment, suitable means of measuring affinities of an antibody to its antigen(s) include Meso Scale Discovery (MSD).

Aspects of the disclosure relate to antibodies that compete or cross-compete with any of the specific antibodies, or antigen-binding fragments thereof, as provided herein, e.g., an antibody having one or more CDR sequences (1, 2, 3, 4, 5, or 6 CDR sequences) as described above. In one embodiment, the invention provides antibodies, and antigen-binding fragments thereof, that compete or cross-compete with an antibody having heavy chain CDR sequences as set forth in SEQ ID NO:6, SEQ ID NO:7, and SEQ ID NO:8, and/or light chain CDR sequences as set forth in SEQ ID NO:9, SEQ ID NO:10, and SEQ ID NO:11. In one embodiment, the invention provides antibodies that compete or cross-compete with an antibody, or antigen-binding fragment thereof, having a heavy chain variable region sequence comprising SEQ ID NO:12, and/or a light chain variable region sequence comprising SEQ ID NO:13.

In one embodiment, the invention provides antibodies, and antigen-binding fragments thereof, that compete or cross-compete with an antibody having heavy chain CDR sequences as set forth in SEQ ID NO:14, SEQ ID NO:15, and SEQ ID NO:16, and/or light chain CDR sequences as set forth in SEQ ID NO:17, SEQ ID NO:18, and SEQ ID NO:19. In one embodiment, the invention provides antibodies that compete or cross-compete with an antibody, or antigen-binding fragment thereof, having a heavy chain variable region sequence comprising SEQ ID NO:20, and/or a light chain variable region sequence comprising SEQ ID NO:21.

In one embodiment, the invention provides antibodies, and antigen-binding fragments thereof, that compete or cross-compete with an antibody having heavy chain CDR sequences as set forth in SEQ ID NO:22, SEQ ID NO:23, and SEQ ID NO:24 and/or light chain CDR sequences as set forth in SEQ ID NO:25, SEQ ID NO:26, and SEQ ID NO:27. In one embodiment, the invention provides antibodies that compete or cross-compete with an antibody, or antigen-binding fragment thereof, having a heavy chain variable region sequence comprising SEQ ID NO:28, and/or a light chain variable region sequence comprising SEQ ID NO:29.

In one embodiment, the invention provides antibodies, and antigen-binding fragments thereof, that compete or cross-compete with an antibody having heavy chain CDR sequences as set forth in SEQ ID NO:30, SEQ ID NO:31, and SEQ ID NO:32, and/or light chain CDR sequences as set forth in SEQ ID NO:33, SEQ ID NO:34, and SEQ ID NO:35. In one embodiment, the invention provides antibodies that compete or cross-compete with an antibody, or antigen-binding fragment thereof, having a heavy chain variable region sequence comprising SEQ ID NO:36, and/or a light chain variable region sequence comprising SEQ ID NO:37.

In one embodiment, the invention provides antibodies, and antigen-binding fragments thereof, that compete or cross-compete with an antibody having heavy chain CDR sequences as set forth in SEQ ID NO:38, SEQ ID NO:39, and SEQ ID NO:40, and/or light chain CDR sequences as set forth in SEQ ID NO:41, SEQ ID NO:42, and SEQ ID NO:43. In one embodiment, the invention provides antibodies that compete or cross-compete with an antibody, or antigen-binding fragment thereof, having a heavy chain variable region sequence comprising SEQ ID NO:44, and/or a light chain variable region sequence comprising SEQ ID NO:45.

In some embodiments, an antibody, or antigen-binding fragment thereof, binds at or near the same epitope as any of the antibodies provided herein. In some embodiments, an antibody, or antigen-binding fragment thereof, binds near an epitope if it binds within 15 or fewer amino acid residues of the epitope. In some embodiments, any of the antibody, or antigen-binding fragment thereof, as provided herein, binds within 1, 2, 3, 4, 5, 6, 7, 8, 9, 10, 11, 12, 13, 14 or 15 amino acid residues of an epitope that is bound by any of the antibodies provided herein.

In another embodiment, provided herein is an antibody, or antigen-binding fragment thereof, competes or cross-competes for binding to any of the antigens provided herein (e.g., a human RGMc) with an equilibrium dissociation constant, $K_D$, between the antibody and the protein of less than $10^{-8}$ M. In other embodiments, an antibody competes or cross-competes for binding to RGMc with a $K_D$ in a range from $10^{-11}$ M to $10^{-8}$ M. In some embodiments, provided herein is an RGMc-specific antibody, or antigen-binding fragment thereof, that competes for binding with an antibody, or antigen-binding fragment thereof, described herein. In some embodiments, provided herein is an RGMc-specific antibody, or antigen-binding fragment thereof, that binds to the same epitope as an antibody, or antigen-binding fragment thereof, described herein.

The antibodies provided herein can be characterized using any suitable methods. For example, one method is to identify the epitope to which the antigen binds, or "epitope mapping." There are many suitable methods for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence).

Peptides of varying lengths (e.g., at least 4-6 amino acids long) can be isolated or synthesized (e.g., recombinantly) and used for binding assays with an antibody. In another example, the epitope to which the antibody binds can be determined in a systematic screen by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids.

The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen-binding domain, domain swapping experiments and alanine scanning mutagenesis can be performed to identify residues required, sufficient, and/or necessary for epitope binding. For example, domain swapping experiments can be performed using a mutant of a target antigen in which various fragments of RGMc have been replaced (swapped) with sequences from a closely related, but antigenically distinct protein, such as another member of the RGMc protein family (e.g., RGMa or RGMb). By assessing binding of the antibody to the mutant RGMc, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Further, the interaction of the any of the antibodies provided herein with one or more residues in RGMc can be determined by routine technology. For example, a crystal structure can be determined, and the distances between the residues in RGMc, and one or more residues in the antibody (or antigen-binding fragment), can be determined accordingly. Based on such distance, whether a specific residue in RGMc interacts with one or more residues in the antibody can be determined. Further, suitable methods, such as competition assays and target mutagenesis assays, can be applied to determine the preferential binding of a candidate antibody.

In some embodiments, the antibodies, or antigen-binding fragments thereof, of the present invention that selectively bind to RGMc include one or more of complementary determining regions (CDRs) as described herein. In some embodiments, the invention provides a nucleic acid molecule that encodes an antibody, or antigen-binding fragment thereof, that selectively binds to a RGMc, as described herein. In one embodiment, the nucleic acid molecules encode one or more of the CDR sequences as described herein.

RGMc-Specific Antibody Binding Regions by H/DX-MS

In the context of the present disclosure, "binding region(s)" of an antigen provides a structural basis for the antibody-antigen interaction. As used herein, a "binding region" refers to the areas of interface between the antibody and the antigen, such that, when bound to RGMc in a physiological solution, the antibody or the fragment protects the binding region from solvent exposure, as determined by suitable techniques, such as hydrogen/deuterium exchange mass spectrometry (H/DX-MS).

The art is familiar with H/DX-MS, which is a widely used technique for exploring protein conformation or protein-protein interactions in solution. This method relies on the exchange of hydrogens in the protein backbone amide with deuterium present in the solution. By measuring hydrogen-deuterium exchange rates, one can obtain information on protein dynamics and conformation (reviewed in: Wei et al. (2014) "Hydrogen/deuterium exchange mass spectrometry for probing higher order structure of protein therapeutics: methodology and applications." Drug Disco Today. 19(1): 95-102; incorporated by reference). The application of this technique is based on the premise that when an antibody-antigen complex forms, the interface between the binding partners may occlude solvent, thereby reducing or preventing the H/D exchange rate due to steric exclusion of solvent.

Using this technique, binding regions of RGMc by an antibody (or fragment such as Fab) can be determined. In some embodiments, a portion on human RGMc identified to be important in binding an antibody or fragment that satisfies the selection criteria set forth herein includes at least a portion of the amino acid stretch YVSSTLSL (SEQ ID NO: 46), which is present within the Alpha-1 Helix domain of RGMc. The same region can be identified on full-length RGMc (SEQ ID NO: 1) as amino acid residues 46-53. As shown in FIG. 8B, this binding region shows sequence diversity among RGM family members. Accordingly, without being bound by a particular theory, it is contemplated that this first binding region (region A) may contribute to RGMc specificity over RGMa and RGMb. In some embodiments, an epitope for the antibody (or the antigen-binding fragment) comprises at least one amino acid residue of the binding region, YVSSTLSL. In some embodiments, an epitope for the antibody (or the antigen-binding fragment) comprises two or more amino acid residue of the binding region.

In some embodiments, a portion on human RGMc identified to be important in binding an antibody or fragment that satisfies the selection criteria set forth herein includes at least a portion of the amino acid stretch FHSAVHGIEDL (SEQ ID NO: 47), which is present within the Alpha-3 Helix domain of RGMc. As shown in the RGMc/BMP2 structural model (FIG. 8C), the Alpha-3 helix is in close proximity to BMP2. Accordingly, without being bound by a particular theory, it is contemplated that this second binding region (region B) may contribute to the functional (e.g., inhibitory) effect of the BMP competitive antibodies described herein. In some embodiments, an epitope for the antibody (or the antigen-binding fragment) comprises at least one amino acid residue of the binding region, FHSAVHGIEDL. In some embodiments, an epitope for the antibody (or the antigen-binding fragment) comprises two or more amino acid residue of the binding region.

Several observations support the notion that SR-RC-AB3-derived antibodies (e.g., SR-RC-AB9) bind at least one amino acid in region A and/or region B of RGMc.

Firstly, based on the HDX-MS data of RGMc with SR-RC-AB9 Fab, regions A and B are relatively flexible and solvent accessible. Therefore, they can be available for binding to the antibody. The relative deuterium uptake of these regions in the unbound form of RGMc showed ~50-60% relative deuterium uptake. Regions that are less accessible are usually less than 30% relative deuterium uptake. Given the high conformational dynamics of the RGMc N-term domain, it is likely that the domain can attain several conformations which increases the probability of antibody binding (see, e.g., FIG. 8C, PDB ID 4UI1, RGMc bound to BMP2).

Secondly, regions A and B also have several points of contact for BMP2 (see FIGS. 8D and 8E) suggesting that these regions are "hot spots" for binding interaction. Moreover, upon closer review of regions A and B, some residues may serve as structural determinants of RGMc specificity over RGMa and RGMb (see FIG. 8E).

Figure 8A:
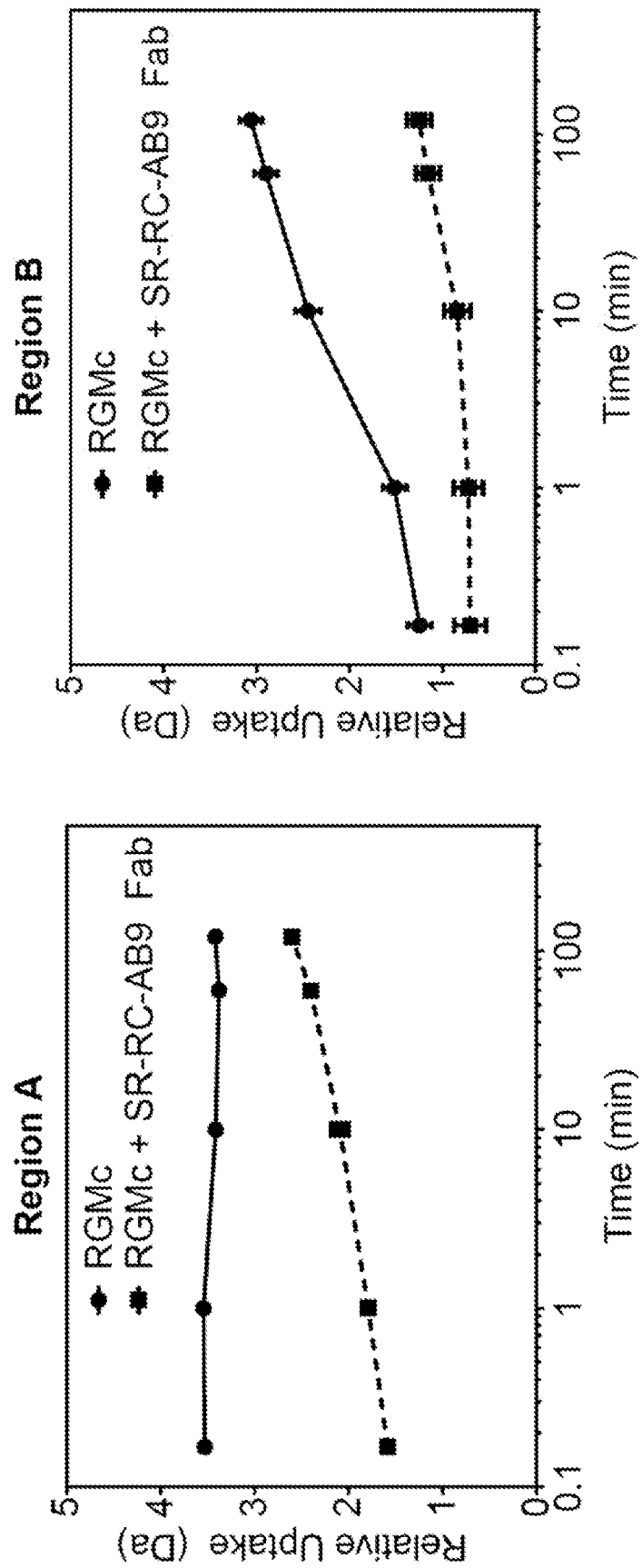
FIG. 8A is a graph that shows reduced deuterium uptake in peptides representing RGMc regions A and B in the presence of SR-RC-AB9 Fab.
Figure 8C:
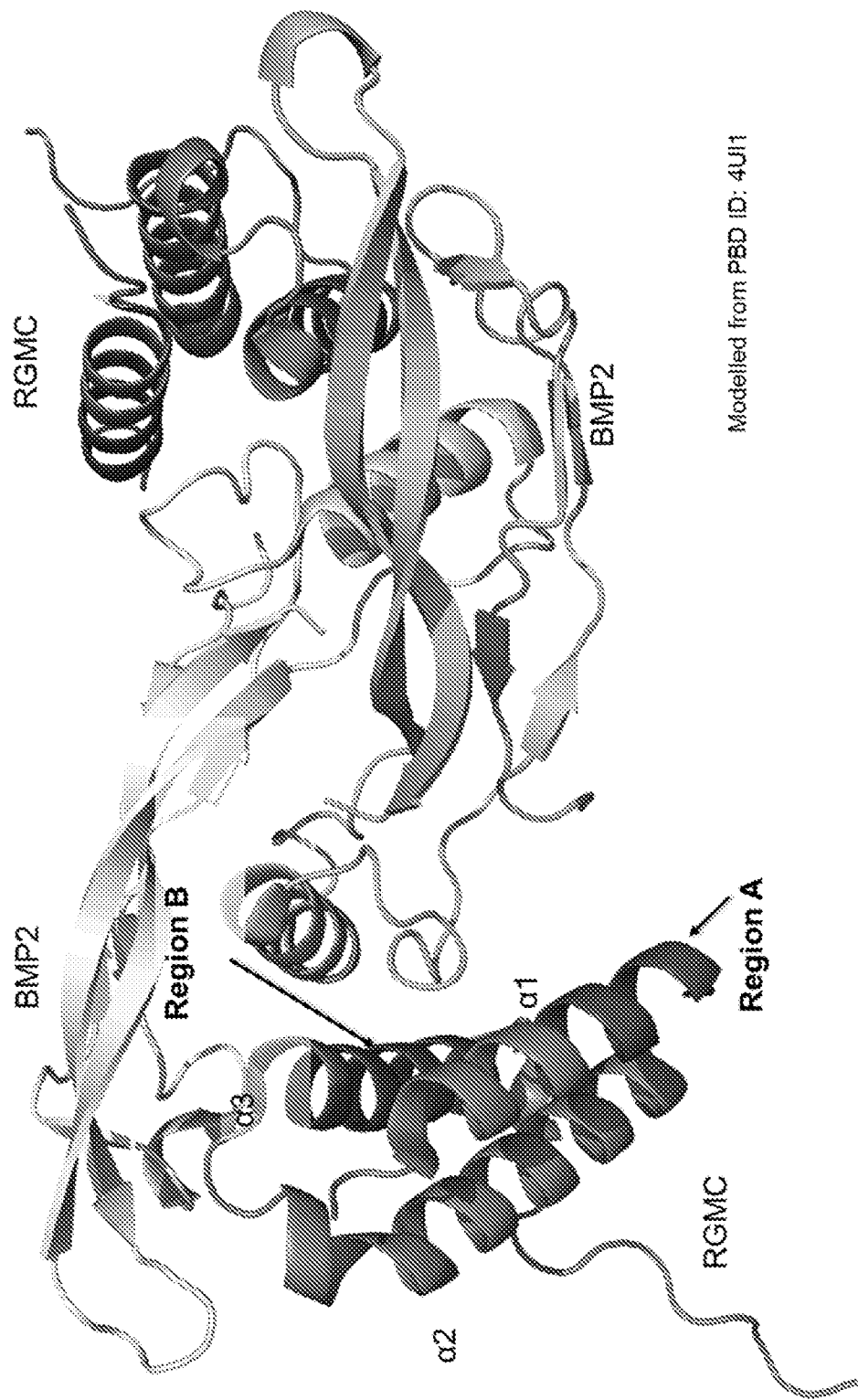
FIG. 8C is a diagram modeling the structure of RGMc in the presence of BMP2. Highlighted are the H/D exchange protected regions A and B.
Figure 8D:
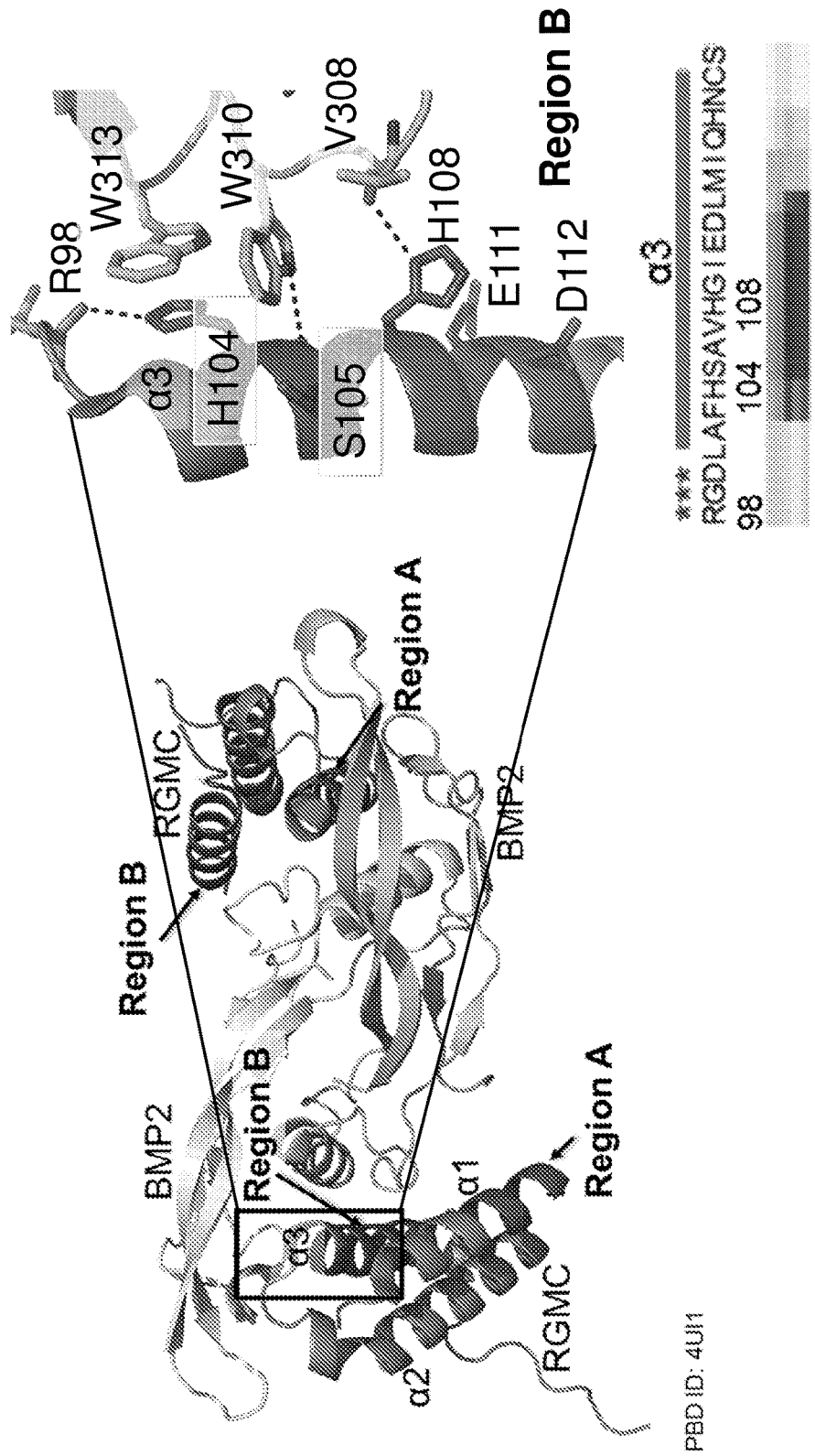
FIG. 8D is a diagram mapping the SR-RC-AB9 fab epitope on to the BMP2 binding site and highlighting potential contact residues within the H/D exchange protected region B. Amino acids 98 to 120 of SEQ ID NO: 1 are shown at the bottom right of the figure.
Figure 8F:
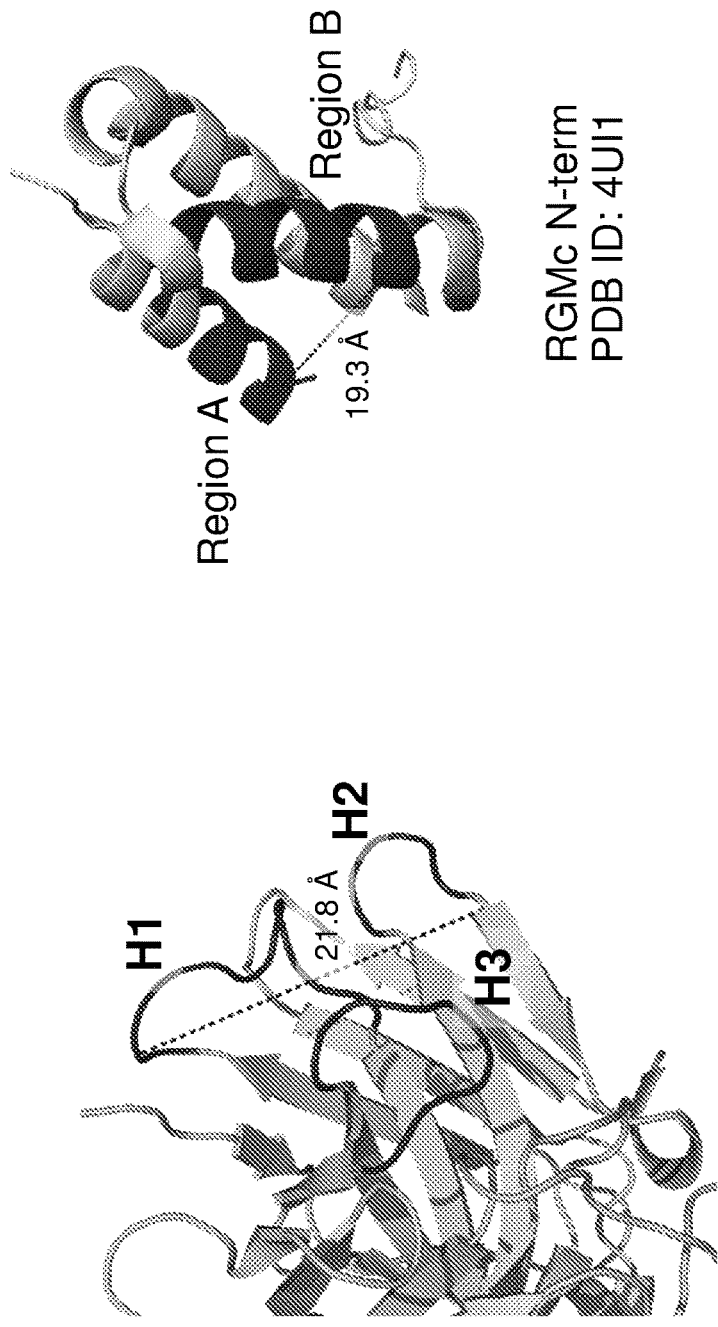
FIG. 8F is a diagram depicting a typical structure of Fab fragment of an antibody highlighting the CDRs H1-H3, which can span the surface of binding regions A and B of RGMc.

Thirdly, the CDRs (H1-H3) of the antibody can span the surface of regions A and B of the RGMc N-term domain (see FIG. 8F). This may suggest that at least one (e.g., one or more) residues of each region participates as epitope for antibody binding. In addition, the shape of the deuterium uptake curve (FIG. 8A) showed significant H/D exchange across time points suggesting that the antibody-antigen interaction is quite stable within regions A and B.

And finally, the binding data for the RGMc N-term with RGMc SR-RC-AB9 fab can also shed light to the idea that both helices (1&3) may be required for antibody binding. In particular, the high binding affinity of SR-RC-AB9 to RGMc suggests that a significant interfacial buried surface of the antigen/antibody interaction must be present. These highly buried surface areas may be possible when both regions A (helix 1) and B (helix 3) participate in binding to the antibody Accordingly, in one embodiment, the RGMc-specific antibody of the invention binds at least at least one amino acid reside of YVSSTLSL (SEQ ID NO: 46). In another embodiment, the RGMc-specific antibody of the invention binds at least at least one amino acid reside of FHSAVHGIEDL (SEQ ID NO: 47). In another embodiment, the RGMc-specific antibody of the invention binds at least at least one amino acid reside of YVSSTLSL (SEQ ID NO: 46) and/or at least one amino acid residue of FHSAVHGIEDL (SEQ ID NO: 47). In another embodiment, the RGMc-specific antibody of the invention binds at least at least one amino acid reside of YVSSTLSL (SEQ ID NO: 46) and at least one amino acid residue of FHSAVHGIEDL (SEQ ID NO: 47). In another embodiment, the RGMc-specific antibody binds to a discontinuous epitope comprising at least one amino acid of each of a first and second binding region within human RGMc, wherein the first binding region comprises the amino acid sequence as set forth in SEQ ID NO: 46; and/or wherein the second binding region comprises the amino acid sequence as set forth in SEQ ID NO: 47. In a particular embodiment, the RGMc-specific antibody binds to a discontinuous epitope comprising at least one amino acid of each of a first and second binding region within human RGMc, wherein the first binding region comprises the amino acid sequence as set forth in SEQ ID NO: 46; and wherein the second binding region comprises the amino acid sequence as set forth in SEQ ID NO: 47.

In some embodiment, the human RGMc-specific antibodies provided herein bind at least a portion of a binding region (region A) having an amino acid sequence YVSSTLSL (SEQ ID NO: 46). In another embodiment, the RGMc-specific antibodies provided herein bind at least a portion of a binding region (region B) having an amino acid sequence FHSAVHGIEDL (SEQ ID NO: 47). In another embodiment, the RGMc-specific antibodies provided herein bind at least a portion of a binding region having an amino acid sequence YVSSTLSL (SEQ ID NO: 46), and/or a portion of a binding region having an amino acid sequence FHSAVHGIEDL (SEQ ID NO: 47). In another embodiment, the RGMc-specific antibodies provided herein bind at least a portion of a binding region having an amino acid sequence YVSSTLSL (SEQ ID NO: 46), and a portion of a binding region having an amino acid sequence FHSAVHGIEDL (SEQ ID NO: 47), or a portion thereof. In a another embodiment, the RGMc-specific antibody binds to a discontinuous epitope comprising at least a portion of a first and second binding region within human RGMc, wherein the first binding region comprises the amino acid sequence as set forth in SEQ ID NO: 46; and/or wherein the second binding region comprises the amino acid sequence as set forth in SEQ ID NO: 47. In a particular embodiment, the RGMc-specific antibody binds to a discontinuous epitope comprising at least a portion of a first and second binding region within human RGMc, wherein the first binding region comprises the amino acid sequence as set forth in SEQ ID NO: 46; and wherein the second binding region comprises the amino acid sequence as set forth in SEQ ID NO: 47.

In some embodiments, the RGMc-specific antibody of the invention binds to a discontinuous epitope within human RGMc, wherein a) the antibody is a full-length antibody or antigen-binding fragment thereof; and b) the antibody binds to a first binding region comprising at least one amino acid residue of YVSSTLSL (SEQ ID NO: 46). In another embodiment, the RGMc-specific antibody of the invention binds to a discontinuous epitope within human RGMc, wherein a) the antibody is a full-length antibody or antigen-binding fragment thereof; and b) the antibody binds to a second binding region comprising at least one amino acid residue of FHSAVHGIEDL (SEQ ID NO: 47). In another embodiment, the RGMc-specific antibody of the invention binds to a discontinuous epitope within human RGMc, wherein a) the antibody is a full-length antibody or antigen-binding fragment thereof; b) the antibody binds to a first binding region comprising at least one amino acid residue of YVSSTLSL (SEQ ID NO: 46); and c) the antibody binds to a second binding region comprising at least one amino acid residue of FHSAVHGIEDL (SEQ ID NO: 47).

Nucleic Acids

In some embodiments, antibodies, antigen-binding fragments thereof, and/or compositions of the present disclosure may be encoded by nucleic acid molecules. Such nucleic acid molecules include, without limitation, DNA molecules, RNA molecules, polynucleotides, oligonucleotides, mRNA molecules, vectors, plasmids and the like. In some embodiments, the present disclosure may comprise cells programmed or generated to express nucleic acid molecules encoding compounds and/or compositions of the present disclosure.

In some embodiments, the invention provides a nucleic acid molecule that encodes the foregoing antibodies, or an antigen-binding fragment thereof. For example, in one embodiment, the invention provides a nucleic acid molecule that encodes a polypeptide comprising CDRH1, CDRH2, CDRH3, CDRL1, CDRL2, or CDRL3, or combinations thereof as described herein. The nucleic acid molecule can, in some embodiments, encode a polypeptide comprising CDRH1, CDRH2, and CDRH3 as described herein. In some embodiments, the nucleic acid molecule can encode a polypeptide comprising CDRL1, CDRL2, and CDRL3 as described herein. In some embodiments, the nucleic acid molecule encodes a polypeptide that can contain up to 5, 4, 3, 2, or 1 amino acid residue variations as compared to the corresponding CDR region in any one of CDRH1, CDRH2, CDRH3, CDRL1, CDRL2, or CDRL3, or combinations thereof, described herein.

In an one embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 12, and/or a light chain variable domain having at least 70%, 75%, 80%, 85%, 90%, 95%, 96%, 97%, 98%, or 99% identity to the amino acid sequence set forth in SEQ ID NO: 13. In an one embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 20, and/or a light chain variable domain having at least 70%, 75%, 80%, 85%, 90%, 95%, 96%, 97%, 98%, or 99% identity to the amino acid sequence set forth in SEQ ID NO: 21. In an one embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 28, and/or a light chain variable domain having at least 70%, 75%, 80%, 85%, 90%, 95%, 96%, 97%, 98%, or 99% identity to the amino acid sequence set forth in SEQ ID NO: 29. In an one embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 36, and/or a light chain variable domain having at least 70%, 75%, 80%, 85%, 90%, 95%, 96%, 97%, 98%, or 99% identity to the amino acid sequence set forth in SEQ ID NO: 37. In an one embodiment, the nucleic acid molecule encodes a polypeptide comprising a heavy chain variable domain having at least 70%, 75%, 80%, 85%, 90%, 95%, 96%, 97%, 98%, or 99% identity to the amino acid sequence set forth in SEQ ID NO: 44, and/or a light chain variable domain having at least 70%, 75%, 80%, 85%, 90%, 95%, 96%, 97%, 98%, or 99% identity to the amino acid sequence set forth in SEQ ID NO: 45.

In some embodiments, the nucleic acid molecule encodes an antibody, or antigen-binding fragment thereof, comprising a heavy chain variable domain amino acid sequence set forth in SEQ ID NO: 12, SEQ ID NO:20, SEQ ID NO:28, SEQ ID NO:36, SEQ ID NO: 44, and a light chain variable domain amino acid sequence set forth in SEQ ID NO: 13, SEQ ID NO:21, SEQ ID NO:29, SEQ ID NO:37, or SEQ ID NO:45. In some embodiments, the nucleic acid molecule encodes an antibody, or antigen-binding fragment thereof, comprising a heavy chain variable domain amino acid sequence set forth in SEQ ID NO: 12, and a light chain variable domain amino acid sequence set forth in SEQ ID NO: 13. In some embodiments, the nucleic acid molecule encodes an antibody, or antigen-binding fragment thereof, comprising a heavy chain variable domain amino acid sequence set forth in SEQ ID NO: 20, and a light chain variable domain amino acid sequence set forth in SEQ ID NO: 21. In some embodiments, the nucleic acid molecule encodes an antibody, or antigen-binding fragment thereof, comprising a heavy chain variable domain amino acid sequence set forth in SEQ ID NO: 28, and a light chain variable domain amino acid sequence set forth in SEQ ID NO: 29. In some embodiments, the nucleic acid molecule encodes an antibody, or antigen-binding fragment thereof, comprising a heavy chain variable domain amino acid sequence set forth in SEQ ID NO: 36, and a light chain variable domain amino acid sequence set forth in SEQ ID NO: 37. In some embodiments, the nucleic acid molecule encodes an antibody, or antigen-binding fragment thereof, comprising a heavy chain variable domain amino acid sequence set forth in SEQ ID NO: 44, and a light chain variable domain amino acid sequence set forth in SEQ ID NO: 45.

In some cases, nucleic acids of the disclosure include codon-optimized nucleic acids. Methods of generating codon-optimized nucleic acids are known in the art and may include, but are not limited to those described in U.S. Pat. Nos. 5,786,464 and 6,114,148, the contents of each of which are herein incorporated by reference in their entirety.

Production of Antibodies that Bind RGMc

The invention encompasses screening methods, production methods and manufacture processes of antibodies or fragments thereof which bind RGMc with high affinity and do not bind RGMa and/or RGMb, and pharmaceutical compositions and related kits comprising the same. The art is familiar with various techniques and methods that may be used for obtaining antibodies, or antigen-binding fragments thereof, of the disclosure. For example, antibodies can be produced using recombinant DNA methods, hybridoma techniques, phage or yeast display technologies, transgenic animals (e.g., a XenoMouse®) or some combination thereof.

i. Immunization and Hybridomas

In some methods described herein, the specified antigen (e.g., an RGMc peptide or protein, e.g., a soluble RGMc peptide or protein) can be used to immunize a non-human animal ("host"), e.g., a rodent, e.g., a mouse, hamster, or rat. In one embodiment, the non-human animal is a mouse. In another embodiment, the host may be a camelid. In a further embodiment, the host may be a shark.

After immunization, which may include single or multiple steps of antigen exposures (e.g., injections), splenocytes are harvested from the animal and the associated B cells are fused with immortalized myeloma cells to form hybridomas for antibody production. Hybridomas may be generated in accordance with known methods (see e.g., Kohler and Milstein (1975) Nature, 256: 495-499). Hybridomas formed in this manner are then screened using standard methods, such as enzyme-linked immunosorbent assay (ELISA), Bio-Layer Interferometry (BLI) technology (e.g., OCTET) and surface plasmon resonance (e.g., BIACORE) analysis, to identify one or more hybridomas that produce an antibody that specifically binds to a specified antigen. Any form of the specified antigen may be used as the immunogen, e.g., recombinant antigen, naturally occurring forms, any variants or fragments thereof, as well as antigenic peptide thereof (e.g., any of the epitopes described herein as a linear epitope or within a scaffold as a conformational epitope).

ii. Screening Library Libraries

In some embodiments, the method or process of making or identifying antibodies includes a step of screening protein expression libraries that express antibodies or fragments thereof (e.g., scFv), e.g., phage, yeast, or ribosome display libraries. For example, a library of human combinatorial antibodies or scFv fragments can synthesized on phages or yeast, the library is then screened with the antigen of interest or an antibody-binding fragment thereof, and the phage or yeast that binds the antigen is isolated, from which one may obtain the antibodies or immunoreactive fragments (Vaughan et al., 1996, PMID: 9630891; Sheets et al., 1998, PMID: 9600934; Boder et al., 1997, PMID: 9181578; Pepper et al., 2008, PMID: 18336206).

Phage display is further described, for example, in Ladner et al., U.S. Pat. No. 5,223,409; Smith (1985) Science 228: 1315-1317; Clackson et al. (1991) Nature, 352: 624-628; Marks et al. (1991) J. Mol. Biol., 222: 581-597; WO 92/18619; WO 91/17271; WO 92/20791; WO 92/15679; WO 93/01288; WO 92/01047; WO 92/09690; and WO 90/02809. Yeast display is further described, for example, in U.S. Pat. Nos. 7,700,302 and 8,877,688. In particular methods, the yeast display library expresses full-length antibodies.

Kits for generating phage or yeast display libraries are commercially available. There also are other methods and reagents that can be used in generating and screening antibody display libraries (see U.S. Pat. No. 5,223,409; WO 92/18619, WO 91/17271, WO 92/20791, WO 92/15679, WO 93/01288, WO 92/01047, WO 92/09690; and Barbas et al., 1991, PMID: 1896445). Such techniques advantageously allow for the screening of large numbers of candidate antibodies.

No matter how obtained, antibody producing cells (e.g., yeast colonies, hybridomas, etc.) may be selected, cloned and further screened for desirable characteristics including, for example, robust growth, high antibody production and desirable antibody characteristics/properties such as high affinity and specific binding to the antigen of interest. Preferably, such antibodies show in vitro binding activities having a $K_D$ value of ≤5 nM, preferably ≤1 nM, more preferably ≤0.1 nM. Thus, an RGMc antibody encompassed by the invention herein has a $K_D$ value of ≤5 nM, preferably ≤1 nM, more preferably ≤0.1 nM, towards recombinant RGMc.

Other selection criteria may include poly-specific reagent (PSR) scores and/or Hydrophobic interaction chromatography (HIC) retention time. A PSR score is one method of determining degree/extent of general binding to proteins (i.e., non-specific binding). For example, in some cases, a poly-specific reagent (PSR) is a preparation of soluble membrane from 293 and/or CHO cells. A low (0.1-0.33) or zero (0-0.10) PSR score is the most desirable profile, while a medium (0.33-0.66) or high (0.66-1.00) score is less desirable. Method of determining PSR scores are well known to those of ordinary skill in the art. In some embodiments, the antibodies or anti-binding fragments thereof, described herein, have a PSR score of <0.1. In other embodiments, the antibodies or anti-binding fragments thereof, described herein, have a PSR score of 0.

On the other hand, an HIC retention time is one method of determining the prosperity of antibodies to self-interact, which predicts whether they will remain soluble/monodispersed in solution (also referred to as aggregation propensity). High HIC retention time indicate greater aggregation propensity. This property could be due to patches of hydrophobic residues/amino acids in the antibody. Alternatively, the presence of post-translational modifications, particularly sugars, can cause antibodies to have low HIC retention times. Accordingly, in some embodiments, the antibodies or antigen-binding fragment thereof, described herein, have a low HIC retention time (e.g., <10.5 minutes). In some embodiments, the antibodies or antigen-binding fragments thereof, described herein, have a medium HIC retention time (e.g., ≥10.5 min and <11.5 min). In some embodiments, the antibodies or antigen-binding fragments thereof, described herein, have a high HIC retention time (e.g., ≥11.5 min).

Methods of selecting, cloning and expanding colonies and/or hybridomas are well known to those of ordinary skill in the art. Once the desired antibodies are identified, the relevant genetic material may be isolated, manipulated, and expressed using common, art-recognized molecular biology and biochemical techniques.

iii. Humanization

The antibodies or fragments of the present invention are preferably fully human antibodies or humanized antibodies. Thus, whatever the source, it will be appreciated that the method may comprise humanizing one or more antibodies or fragments thereof, wherein the human antibody sequences may be fabricated using art-known molecular engineering techniques and introduced into expression systems and host cells as described herein. Such non-natural recombinantly produced human antibodies (and subject compositions) are entirely compatible with the teachings of this disclosure and are expressly held to be within the scope of the instant invention. In certain select aspects, the RGMc antibodies of the invention will comprise a recombinantly produced human antibody.

iv. Affinity Maturation and Optimization

In some embodiments, antibodies produced by the methods described-above may be of moderate affinity (e.g., Ka of about $10^6$ to $10^7$ M$^{-1}$ or a $K_D$ of about $10^{-6}$ to $10^{-7}$ M). Accordingly, antibodies or fragments thereof may be subjected to a process of affinity maturation as part of optimization, if desired. The term "affinity maturation" shall have the meaning readily understood by the skilled artisan. Briefly, it refers to further modifying the amino acid sequence of candidate antibodies or fragments (often referred to as "parent" or "parental") to achieve improved binding profiles to the specific antigen. Typically, a parental antibody and an affinity-matured counterpart (sometimes referred to as "progeny" or "offspring") retain the same epitope. Suitable in vitro binding assays may be carried out to screen for improved binders at appropriate step(s) during the affinity maturation process. Optionally, in some embodiments, functional assays (e.g., cell-based potency assays, in vitro functional assays, etc.) may also be performed to confirm desired functionality.

Affinity maturation typically involves sequence diversification and/or mutagenesis, whilst the exact means of introducing or generating mutations or sequence alterations is not limiting. In some embodiments, mutagenesis comprises introducing one or more changes (e.g., substitutions or deletions) in amino acid residues of one or more CDRs. Accordingly, in some embodiments the VR or CDR sequences described herein may comprise up to one, two, three, or four amino acid changes relative to a reference sequence (e.g., that of a parent sequence). In some embodiments, the VR or CDR sequences described herein may comprise up to one, two, three, or four amino acid substitutions. In some embodiments, the VR or CDR sequences described herein may comprise up to one, two, three, or four deletions. Additionally or alternatively, the process of mutagenesis may comprise so-called oligo-walking of variable regions or CDRs.

For example, affinity maturation of antibodies can be accomplished by a number of methods including random mutagenesis (Gram H., et al. Proc. Natl. Acad. Sci. U.S.A. (1992) 89, 3576-3580, and Hawkins R. E., et al. J. Mol. Biol. (1992) 226, 889-896), random mutagenesis of CDR sequences, e.g., CDR walking (Yang W. P., et al., J. Mol. Biol. (1995) 254, 392-403), directed mutagenesis of residues (Ho M., et al., J. Biol. Chem. (2005) 280, 607-617 and Ho M., et al., Proc. Natl. Acad. Sci. U.S.A. (2006) 103, 9637-9642), and approaches that reproduce somatic hypermutation (SHM) in vitro (Bowers P. M., et al., Proc. Natl. Acad. Sci. U.S.A. (2011) 108, 20455-20460).

In one embodiment, antibodies may be affinity-matured by conducting mutagenesis on the variable heavy or variable light chain regions. In another embodiment, antibodies may be affinity matured by conducting mutagenesis on any one of the variable heavy chain CDRs or variable light chain CDRs. In another embodiment, antibodies may be affinity matured by conducting mutagenesis on the variable heavy chain CDR3. In another embodiment, antibodies may be affinity matured by conducting mutagenesis on the variable heavy chain CDR2. In another embodiment, antibodies may be affinity matured by conducting mutagenesis on the variable heavy chain CDR1. In another embodiment, antibodies may be affinity matured by conducting mutagenesis on the variable light chain CDR3. In another embodiment, antibodies may be affinity matured by conducting mutagenesis on the variable light chain CDR2. In another embodiment, antibodies may be affinity matured by conducting mutagenesis on the variable light chain CDR1.

In some embodiments, affinity maturation involves screening an antibody library comprising variants of one or more CDRs ("repertoire"), which may be combined with at least one CDR of a parent antibody. This process is sometimes called CDR shuffling or CDR diversification. In some embodiments, a variable heavy chain CDR3 (e.g., CDR-H3) may be used to screen a library that contains variable heavy chain CDR1 and CDR2 (e.g., CDR-H1 and CDR-H2) repertoires of variants (also called CDR-H1/H2 diversification). In some embodiments, variable light chain CDR3 (e.g., CDR-L3) may be used to screen a library that contains variable light chain CDR1 and CDR2 (e.g., CDR-L1 and CDR-L2) repertoires of variants (also called CDR-L1/L2 diversification).

In some embodiments, affinity maturation involves screening an antibody library comprising light chain variants ("repertoire"), which may be combined with a heavy chain of a parent antibody (light-chain shuffling). For example, in some embodiments, selected heavy chains are introduced into an antibody library comprising light chain variants thereby producing a new library of antibodies that can be screened for improved affinity. In some embodiments, repertoires of naturally occurring variable region variants may be obtained from unimmunized donors. Examples of heavy or light-chain shuffling are described in the following documents: Marks et al., (1992) Nature Biotech 10: 779-78; Schier et al., (1996) J. Mol. Biol. 255, 28-43; Park et al., (2000) BBRC. 275. 553-557; and Chames et al., (2002) J. Immunol 1110-1118. In some embodiments, the light chain library comprises lambda light chains variants. In some embodiments, the light chain library comprises kappa light chains variants. In some embodiments, the light chain library comprises both lambda and kappa light chains variants.

It should be appreciated that the various methods for affinity maturation may be combined in any order. For example, in one embodiment, a select antibody may undergo heavy chain CDR diversification, followed by CDR-H3 mutagenesis. In another embodiment, a select antibody may undergo heavy chain CDR diversification, followed by CDR-H3 mutagenesis, followed by light chain shuffling. In another embodiment, a select antibody may undergo heavy chain CDR shuffling, followed by light chain shuffling, followed by CDR-H3 mutagenesis. In a preferred embodiment, a select antibody may undergo light chain shuffling, followed by CDR-H1/H2 diversification, followed by CDR-H3 mutagenesis.

In any of the methods for affinity maturation described above, the resulting new antibodies may be selected for binding to the target antigen (e.g., soluble RGMc) using known techniques (e.g., FACS). Binding specificity and affinity using FACS may be tested by varying antigen concentration and/or competition for unlabeled (cold) antigen. Binding affinity can be further assessed using other techniques known in the art, such as ELISA, BLI (e.g., OCTET), and SPR (e.g., BIACORE).

In addition to the affinity maturation process discussed above, further optimization may be performed to achieve desired product profiles. Thus, antibodies may be further subjected to a step of optimization and selected based on certain physicochemical properties that are advantageous. For therapeutic antibodies (biologics), physicochemical criteria for developability that may be evaluated include, but are not limited to: solubility, stability, immunogenicity, lack of self-association or aggregation, Fc functionality, internalization profiles, pH-sensitivity, glycosylation and manufacturability such as cell viability and/or gene expression. In some embodiments, the process of optimization involves mutagenesis of one or more amino acid sequences within the constant regions.

In one aspect, the invention provides a method for making a pharmaceutical composition comprising an antibody, or antigen-binding fragment thereof, that specifically binds a human RGMc, and does not bind a human RGMa or human RGMb; wherein the antibody, or antigen-binding fragment thereof, inhibits RGMc but does not inhibit RGMa or RGMb, the method comprising steps of i) providing at least one antigen comprising human RGMc (such as soluble human RGMc), ii) selecting a first pool of antibodies, or antigen-binding fragments thereof, that specifically bind human RGMc so as to provide specific binders of human RGMc; iii) selecting a second pool of antibodies, or antigen-binding fragments thereof, that inhibit RGMc-associated BMP6 signaling, so as to generate specific inhibitors of RGMc/BMP6 activity; iv) formulating an antibody, or antigen-binding fragment thereof, that is present in the first pool of antibodies and the second pool of antibodies into a pharmaceutical composition, thereby making the composition comprising the antibody, or antigen-binding fragment thereof.

In a preferred embodiment, the method further comprises a step of removing from the first pool of antibodies, or antigen-binding fragments thereof, any antibodies, or antigen-binding fragments thereof, that bind human RGMa and/or human RGMb. In one embodiment, the method further comprises a step of determining or confirming the specificity of the antibodies, or antigen-binding fragments thereof, selected in steps (ii) and/or (iii). In one embodiment, the method further comprises a step of selecting for antibodies, or antigen-binding fragments thereof, that are cross-reactive to human and rodent antigens. In one embodiment, the method further comprises a step of generating a fully human or humanized antibody, or antigen-binding fragment thereof, of the antibody, or antigen-binding fragment thereof, that is present in the first pool of antibodies and the second pool of antibodies. In one embodiment, the method further comprises a step of subjecting the antibody, or antigen-binding fragment thereof, that is present in the first pool of antibodies and the second pool of antibodies to affinity maturation and/or optimization, so as to provide an affinity matured and/or optimized antibody or fragment thereof.

In some embodiments, the method for making the pharmaceutical composition further includes a step of testing one or more candidate RGMc inhibitor(s) in at least one in vivo model to evaluate or confirm efficacy for achieving or correcting iron regulation. In some embodiments, the method for making the pharmaceutical composition further includes a step of testing one or more candidate RGMc inhibitor(s) (e.g., such antibodies that show in vivo efficacy) in at least one in vivo model to evaluate safety/tolerability at doses at or higher than therapeutically effective doses. Suitable therapeutic antibodies should show acceptable toxicities at dosage that is sufficiently greater than efficacious dosage in animal models. In some embodiments, in vivo efficacy and or safety studies may be performed with the use of antibody or antibodies that comprise non-CDR portion or portions that more closely match the particular species used in the preclinical study (e.g., murine counterpart, etc.).

In another embodiment, a monoclonal antibody is obtained from the non-human animal, and then modified, e.g., made chimeric, using suitable recombinant DNA techniques. A variety of approaches for making chimeric antibodies have been described. See e.g., Morrison et al., Proc.

Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

For additional antibody production techniques, see, e.g., Antibodies: A Laboratory Manual, eds. Harlow et al., Cold Spring Harbor Laboratory, 1988. The present disclosure is not necessarily limited to any particular source, method of production, or other special characteristics of an antibody.

Some aspects of the present disclosure relate to host cells transformed with a polynucleotide or vector. Host cells may be a prokaryotic or eukaryotic cell. The polynucleotide or vector which is present in the host cell may either be integrated into the genome of the host cell or it may be maintained extrachromosomally. The host cell can be any prokaryotic or eukaryotic cell, such as a bacterial, insect, fungal, plant, animal or human cell. In some embodiments, fungal cells are, for example, those of the genus *Saccharomyces*, in particular those of the species *S. cerevisiae*. The term "prokaryotic" includes all bacteria which can be transformed or transfected with a DNA or RNA molecules for the expression of an antibody or the corresponding immunoglobulin chains. Prokaryotic hosts may include gram negative as well as gram positive bacteria such as, for example, *E. coli, S. typhimurium, Serratia marcescens* and *Bacillus subtilis*. The term "eukaryotic" includes yeast, higher plants, insects and vertebrate cells, e.g., mammalian cells, such as NSO and CHO cells. Depending upon the host employed in a recombinant production procedure, the antibodies or immunoglobulin chains encoded by the polynucleotide may be glycosylated or may be non-glycosylated. Antibodies or the corresponding immunoglobulin chains may also include an initial methionine amino acid residue.

In some embodiments, once a vector has been incorporated into an appropriate host, the host may be maintained under conditions suitable for high level expression of the nucleotide sequences, and, as desired, the collection and purification of the immunoglobulin light chains, heavy chains, light/heavy chain dimers or intact antibodies, antigen-binding fragments or other immunoglobulin forms may follow; see, Beychok, Cells of Immunoglobulin Synthesis, Academic Press, N.Y., (1979). Thus, polynucleotides or vectors are introduced into the cells which in turn produce the antibody or antigen-binding fragments. Furthermore, transgenic animals, preferably mammals, comprising the aforementioned host cells may be used for the large scale production of the antibody or antibody fragments.

The transformed host cells can be grown in fermenters and cultured using any suitable techniques to achieve optimal cell growth. Once expressed, the whole antibodies, their dimers, individual light and heavy chains, other immunoglobulin forms, or antigen-binding fragments, can be purified according to standard procedures of the art, including ammonium sulfate precipitation, affinity columns, column chromatography, gel electrophoresis and the like; see, Scopes, "Protein Purification", Springer Verlag, N.Y. (1982). The antibody or antigen-binding fragments can then be isolated from the growth medium, cellular lysates, or cellular membrane fractions. The isolation and purification of the, e.g., microbially expressed antibodies or antigen-binding fragments may be by any conventional means such as, for example, preparative chromatographic separations and immunological separations such as those involving the use of monoclonal or polyclonal antibodies directed, e.g., against the constant region of the antibody.

Aspects of the disclosure relate to a hybridoma, which provides an indefinitely prolonged source of monoclonal antibodies. As an alternative to obtaining immunoglobulins directly from the culture of hybridomas, immortalized hybridoma cells can be used as a source of rearranged heavy chain and light chain loci for subsequent expression and/or genetic manipulation. Rearranged antibody genes can be reverse transcribed from appropriate mRNAs to produce cDNA. In some embodiments, heavy chain constant region can be exchanged for that of a different isotype or eliminated altogether. The variable regions can be linked to encode single chain Fv regions. Multiple Fv regions can be linked to confer binding ability to more than one target or chimeric heavy and light chain combinations can be employed. Any appropriate method may be used for cloning of antibody variable regions and generation of recombinant antibodies.

In some embodiments, an appropriate nucleic acid that encodes variable regions of a heavy and/or light chain is obtained and inserted into an expression vectors which can be transfected into standard recombinant host cells. A variety of such host cells may be used. In some embodiments, mammalian host cells may be advantageous for efficient processing and production. Typical mammalian cell lines useful for this purpose include CHO cells, 293 cells, or NSO cells. The production of the antibody or antigen-binding fragment may be undertaken by culturing a modified recombinant host under culture conditions appropriate for the growth of the host cells and the expression of the coding sequences. The antibodies or antigen-binding fragments may be recovered by isolating them from the culture. The expression systems may be designed to include signal peptides so that the resulting antibodies are secreted into the medium; however, intracellular production is also possible.

The disclosure also includes a polynucleotide encoding at least a variable region of an immunoglobulin chain of the antibodies described herein. In some embodiments, the variable region encoded by the polynucleotide comprises at least one complementarity determining region (CDR) of the VH and/or VL of the variable region of the antibody produced by any one of the above described hybridomas.

Polynucleotides encoding antibody or antigen-binding fragments may be, e.g., DNA, cDNA, RNA or synthetically produced DNA or RNA or a recombinantly produced chimeric nucleic acid molecule comprising any of those polynucleotides either alone or in combination. In some embodiments, a polynucleotide is part of a vector. Such vectors may comprise further genes such as marker genes which allow for the R the vector in a suitable host cell and under suitable conditions.

In some embodiments, a polynucleotide is operatively linked to expression control sequences allowing expression in prokaryotic or eukaryotic cells. Expression of the polynucleotide comprises transcription of the polynucleotide into a translatable mRNA. Regulatory elements ensuring expression in eukaryotic cells, preferably mammalian cells, are well known to those skilled in the art. They may include regulatory sequences that facilitate initiation of transcription and optionally poly-A signals that facilitate termination of transcription and stabilization of the transcript. Additional regulatory elements may include transcriptional as well as translational enhancers, and/or naturally associated or heterologous promoter regions. Possible regulatory elements permitting expression in prokaryotic host cells include, e.g., the PL, Lac, Trp or Tac promoter in *E. coli*, and examples of regulatory elements permitting expression in eukaryotic host cells are the AOX1 or GAL1 promoter in yeast or the CMV-promoter, SV40-promoter, RSV-promoter (Rous sarcoma virus), CMV-enhancer, SV40-enhancer or a globin intron in mammalian and other animal cells.

Beside elements which are responsible for the initiation of transcription such regulatory elements may also include transcription termination signals, such as the SV40-poly-A site or the tk-poly-A site, downstream of the polynucleotide. Furthermore, depending on the expression system employed, leader sequences capable of directing the polypeptide to a cellular compartment or secreting it into the medium may be added to the coding sequence of the polynucleotide and have been described previously. The leader sequence(s) is (are) assembled in appropriate phase with translation, initiation and termination sequences, and preferably, a leader sequence capable of directing secretion of translated protein, or a portion thereof, into, for example, the extracellular medium. Optionally, a heterologous polynucleotide sequence can be used that encode a fusion protein including a C- or N-terminal identification peptide imparting desired characteristics, e.g., stabilization or simplified purification of expressed recombinant product.

In some embodiments, polynucleotides encoding at least the variable domain of the light and/or heavy chain may encode the variable domains of both immunoglobulin chains or only one. Likewise, polynucleotides may be under the control of the same promoter or may be separately controlled for expression. Furthermore, some aspects relate to vectors, particularly plasmids, cosmids, viruses and bacteriophages used conventionally in genetic engineering that comprise a polynucleotide encoding a variable domain of an immunoglobulin chain of an antibody or antigen-binding fragment; optionally in combination with a polynucleotide that encodes the variable domain of the other immunoglobulin chain of the antibody.

In some embodiments, expression control sequences are provided as eukaryotic promoter systems in vectors capable of transforming or transfecting eukaryotic host cells, but control sequences for prokaryotic hosts may also be used. Expression vectors derived from viruses such as retroviruses, vaccinia virus, adeno-associated virus, herpes viruses, or bovine papilloma virus, may be used for delivery of the polynucleotides or vector into targeted cell population (e.g., to engineer a cell to express an antibody or antigen-binding fragment). A variety of appropriate methods can be used to construct recombinant viral vectors. In some embodiments, polynucleotides and vectors can be reconstituted into liposomes for delivery to target cells. The vectors containing the polynucleotides (e.g., the heavy and/or light variable domain(s) of the immunoglobulin chains encoding sequences and expression control sequences) can be transferred into the host cell by suitable methods, which vary depending on the type of cellular host.

Accordingly, in one aspect of the invention, method for making a pharmaceutical composition comprising an RGMc-selective inhibitor (e.g., neutralizing antibody) is provided, the method comprising the steps of: i) identifying antibodies or antigen-binding fragments for the ability to selectively bind RGMc over RGMa and RGMb; ii) identifying the antibodies or antigen-binding fragment based on step (i) for the ability to inhibit/neutralize RGMc activity in vivo; iii) selecting an inhibitory/neutralizing antibody based on steps (i) and (ii) for formulation into a pharmaceutical composition. In one embodiment, step (i) comprises a positive selection and optionally further comprises a negative selection. In some embodiments, the identification step (i) comprises screening a library. In some embodiments, the library is a phage library or a yeast library. In some embodiments, the identification step (ii) comprises measuring an iron parameter selected from the group consisting of: serum iron, total iron binding capacity (TIBC), unsaturated iron binding capacity (UIBC), and transferrin saturation. In some embodiments, step (ii) comprises measuring hepcidin expression. In some embodiments, the hepcidin expression is liver hepcidin levels and/or serum hepcidin levels. In some embodiments, step (ii) comprises identifying neutralizing antibodies or antigen-binding fragments capable of elevating serum iron levels and/or suppressing hepcidin expression in vivo. In some embodiments, step (i) comprises confirming selectively for RGMc over RGMa and RGMb.

In another embodiment, the antibodies or antigen-binding fragments produced by the methods disclosed herein bind an epitope that excludes a BMP6 binding site. In some embodiments, the epitope excludes a Neogenin-binding site. In some embodiments, the epitope excludes both a BMP6-binding site and a Neogenin-binding site. In some embodiments, the antibody or antigen-binding fragment preferentially binds membrane-bound RGMc over soluble RGMc. In some embodiments, the antibody induces internalization of an antibody-antigen complex.

In another embodiment, the pharmaceutical composition produced by the method disclosed herein is formulated for an intravenous or subcutaneous administration.

Modifications

Antibodies, or antigen-binding fragments thereof, of the disclosure may be modified with a detectable label or detectable moiety, including, but not limited to, an enzyme, prosthetic group, fluorescent material, luminescent material, bioluminescent material, radioactive material, positron emitting metal, nonradioactive paramagnetic metal ion, and affinity label for detection and isolation of RGMc. The detectable substance or moiety may be coupled or conjugated either directly to the polypeptides of the disclosure or indirectly, through an intermediate (such as, for example, a linker (e.g., a cleavable linker)) using suitable techniques. Non-limiting examples of suitable enzymes include horseradish peroxidase, alkaline phosphatase, β-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine (131I, 125I, 123I, 121I), carbon (14C), sulfur (35S), tritium (3H), indium (115mIn, 113mIn, 112In, 111In), and technetium (99Tc, 99mTc), thallium (201Ti), gallium (68Ga, 67Ga), palladium (103Pd), molybdenum (99Mo), xenon (133Xe), fluorine (18F), 153Sm, Lu, 159Gd, 149Pm, 140La, 175Yb, 166Ho, 90Y, 47Sc, 86R, 188Re, 142Pr, 105Rh, 97Ru, 68Ge, 57Co, 65Zn, 85Sr, 32P, 153Gd, 169Yb, 51Cr, 54Mn, 75Se, and tin (113Sn, 117Sn).

The detectable substance may be coupled or conjugated either directly to the antibodies of the disclosure that bind specifically to RGMc, or indirectly, through an intermediate (such as, for example, a linker) using suitable techniques. Any of the antibodies provided herein that are conjugated to a detectable substance may be used for any suitable diagnostic assays, such as those described herein.

In addition, antibodies, or antigen-binding fragments thereof, of the disclosure may also be modified with a drug. The drug may be coupled or conjugated either directly to the polypeptides of the disclosure, or indirectly, through an intermediate (such as, for example, a linker (e.g., a cleavable linker)) using suitable techniques.

Pharmaceutical Compositions, Formulations

Further provided are pharmaceutical compositions/formulations used as medicaments suitable for administration in human and non-human subjects. For example, one or more RGMc-specific antagonists (e.g., antibodies) encompassed by the invention can be formulated or admixed with a pharmaceutically acceptable carrier (excipient), including, for example, a buffer, to form a pharmaceutical composition. Such formulations may be used for the treatment of a disease or disorder that involves RGMc signaling. In particularly preferred embodiments, the formulations may be used for the treatment of anemia as described herein.

The pharmaceutical compositions of the invention may be administered to patients for alleviating an RGMc-related indication. For example, an RGMc-related indication can be an iron-restricted anemia. Examples of iron-restricted anemias encompassed by the present invention include, but are not limited to anemia of chronic disease (e.g., CKD), Iron-refractory iron deficiency anemia (IRIDA), cancer-induced anemia, and/or chemotherapy-induced anemia.

"Acceptable" means that the carrier is compatible with the active ingredient of the composition (and preferably, capable of stabilizing the active ingredient) and not deleterious to the subject to be treated. Examples of pharmaceutically acceptable excipients (carriers), including buffers, would be apparent to the skilled artisan and have been described previously. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions (Remington: The Science and Practice of Pharmacy 20th Ed. (2000) Lippincott Williams and Wilkins, Ed. K. E. Hoover).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g. antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenylsubstituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Other acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™ PLURONICS™ or polyethylene glycol (PEG). Pharmaceutically acceptable excipients are further described herein.

In some examples, the pharmaceutical composition described herein comprises liposomes containing an antibody that specifically binds RGMc, which can be prepared by any suitable method, such as described in Epstein et al., Proc. Natl. Acad. Sci. USA 82:3688 (1985); Hwang et al. Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies described herein may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Exemplary techniques have been described previously, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl-alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present disclosure, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 mg to about 500 mg of the active ingredient of the present disclosure. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%.

The emulsion compositions can be those prepared by mixing an antibody of the invention with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Therapeutic Use, Methods of Treatment, Patient Populations

Abnormalities in iron homeostasis are associated with a number of diseases that can be difficult to diagnose and treat. Such disorders can be broadly classified into two categories, i) iron-overload diseases that include cirrhosis, cardiomyopathy, diabetes, etc.; and, ii) iron-deficient diseases, including anemia, anemia of chronic disease ("ACD"), etc. Iron Deficiency Anemia (IDA) can be separated into two major forms: absolute iron deficiency (AID) and functional iron deficiency (FID). AID is defined by a decrease in the body iron stores, while FID is a disorder in which the total body iron stores are normal or increased but the iron supply to the bone marrow (e.g., iron mobilization) is dysregulated or inadequate.

Current treatment options for iron-related diseases include external iron supplementation such as IV iron, and ESA therapy (e.g., EPO and similar agents). However, these therapies are associated with unwanted side effects. For example, it has been shown that chronic anemia patients who receive frequent iron supplements, such as IV iron, may develop iron overload. Excess body iron can be highly toxic, which may affect a number of organs, leading to a variety of serious conditions such as liver disease, heart disease, diabetes mellitus, hormonal abnormalities, and dysfunctional immune system. Similarly, patients who receive blood transfusion are at risk of toxicities associated with iron overload. For example, in patients who receive numerous transfusions, notably those with thalassemia major, sickle cell disease, myelodysplastic syndrome, aplastic anemia, hemolytic anemia, and refractory sideroblastic anemias, who may become transfusion dependent, the excess iron from the transfused erythrocytes (approximately 250 mg per transfusion) gradually accumulates in various tissues, causing morbidity and mortality. Thus, treatment-induced excess iron in the body can cause severe adverse reactions including toxicities to cardiovascular, gastrointestinal, immune, bone/cartilage, reproductive, and renal systems.

As an added or alternative treatment option to IV iron, ESA therapy (e.g., EPO) has been extensively administered to a wide range of patient populations, including those suffering from cancer-related and chemotherapy-induced anemia in patients. Paradoxically, however, recent preclinical and clinical studies indicate that ESAs could potentially accelerate tumor growth and jeopardize survival in cancer patients.

HIF stabilizers, in lieu of exogenously added erythropoietin or its equivalents, are aimed to stimulate the body's ability to produce endogenous erythropoietin in order to increase red blood cells through the HIF signaling cascade. It has been hypothesized that this approach may potentially reduce risk factors associated with ESA therapies, such as increased cancer progression and major adverse cardiac events (e.g., stroke). To date, however, improved safety has not yet been clearly established.

More recently, monoclonal antibodies that specifically bind RGMa/RGMc were shown to increase serum iron in rats and cynomolgus monkeys by downregulating hepcidin (Boser et al. (2015) AAPS J. 2015 July; 17(4): 930-938). In this case, the investigators observed no obvious toxicities in healthy animals that received the RGMa/RGMc antibodies and normalization of blood parameters were seen after a recovery period (~12 week) following a dosing period. However, potential risks associated with concurrent inhibition of RGMa, for example, on the nervous system and immunomodulatory effects, are not discernable from the published work.

Thus, improved therapies for achieving iron homeostasis are needed that can be used effectively and safely to treat patients with diseases and disorders involving imbalance in iron homeostasis, for example, anemia.

Accordingly, in one aspect, the present invention provides improved methods for treating and/or preventing conditions associated with perturbations in iron metabolism, particularly conditions associated with iron deficiency (e.g., anemia). The RGMc-selective inhibitors (e.g., monoclonal antibodies and antigen-binding fragments thereof that selectively bind and inhibit RGMc but not RGMa/b) may be used in the treatment of conditions involving functional iron deficiency in subjects. The therapeutic use comprises administration of one or more the RGMc-selective inhibitors according to the present disclosure in an amount effective to treat the subject. The treatment may include relief, alleviation, normalization or maintenance of one or more symptoms/parameters of anemia, such as serum iron levels, transferrin saturation (TAST), reticulocyte hemoglobin content (CHr), reticulocyte count, red blood cell count, hemoglobin, and hematocrit. The RGMc-selective inhibitor may provide clinical benefits in terms of the degree of therapeutic effects and/or the kinetics or timing of such effects (such as faster relief, more prolonged effects, etc.). The RGMc-selective inhibitor may provide clinical benefits in terms of reducing toxicities or adverse events associated with therapy aimed to treat anemia or underlining disease causing the anemia.

Such conditions that may be treated and/or prevented using the methods of the present invention include any disease, disorder, or syndrome associated with perturbations in iron metabolism. Perturbations in iron metabolism may be associated with disturbances in one or more of iron uptake, iron absorption, iron transport, iron storage, iron processing, iron mobilization, and iron utilization. Generally, perturbations in iron metabolism result in iron overload or iron deficiency.

A disease or disorder of iron metabolism may be any disease or disorder in which iron homeostasis is perturbed in the subject. This homeostasis relies on the proper regulation of adequate plasma iron levels. Iron circulates in plasma bound to transferrin, which is a vehicle for iron delivery into cells. Plasma transferrin is normally about 30% saturated with iron. Accordingly, transferrin saturation must be maintained at appropriate physiological levels in response to a variety of signals from pathways involved in iron consumption.

Diseases associated with iron deficiency include, but are not limited to, anemia of chronic disease, iron deficiency anemias, absolute iron deficiency, functional iron deficiency, and microcytic anemia. This disruption of iron homeostasis may also result in anemia of chronic disease, wherein a subject with the disease exhibits high levels of blood hepcidin. The term "anemia of chronic disease" (ACD) refers to any anemia that develops as a result of, for example, extended infection, inflammation, neoplastic disorders, etc. The anemia that develops is often characterized by a shortened red blood cell life span and sequestration of iron in macrophages, which results in a decrease in the amount of iron available to make new red blood cells. Conditions associated with anemia of chronic disease include, but are not limited to, chronic bacterial endocarditis, osteomyelitis, rheumatic fever, ulcerative colitis, chronic kidney disease, and neoplastic disorders.

Additionally, subjects having a disease associated with iron deficiency (e.g., ACD) may have, or be at risk of, a disease or disorder such as fatigue, joint pain, bone or joint disease (osteoarthritis, osteoporosis), rheumatoid arthritis, inflammatory bowel disease, shortness of breath, irregular heartbeat, liver trouble, diabetes, infertility, impotence, depression, mood or mental disorders, poor cognitive skills or neurodegenerative diseases, iron-refractory iron-deficiency anemia, anemia of chronic kidney disease, resistance to erythropoiesis-stimulating agents, aplastic anemia, cancer, hypoplastic anemias, paroxysmal nocturnal hemoglobinuria, von Willebrand disease, and hemophilia hereditary hemorrhagic telangiectasia.

Further conditions include diseases and disorders associated with infection, inflammation, and neoplasms, including, for example, inflammatory infections (e.g., pulmonary abscess, tuberculosis, etc.), inflammatory noninfectious disorders (e.g., rheumatoid arthritis, systemic lupus erythrematosus, Crohn's disease, hepatitis, inflammatory bowel disease, etc.), and various cancers, tumors, and malignancies (e.g., carcinoma, sarcoma, lymphoma, etc.). Iron deficiency anemia may also result from chemotherapy treatment or conditions such as pregnancy, menstruation, infancy and childhood, blood loss due to injury, etc.

Conditions associated with iron overload include both primary and secondary iron overload diseases, syndromes or disorders, including, but not limited to, hereditary hemochromatosis, *porphyria* cutanea *tarda*, hereditary spherocytosis, hyprochromic anemia, hysererythropoietic anemia (CDAI), congenital dyserythropoietic anemia (CDAII), faciogenital dysplasia (FGDY), Aarskog syndrome, atransferrinemia, sideroblastic anemia (SA), pyridoxine-responsive sidero-blastic anemia, red cell enzymopathies such as glucose-6 phosphate dehydrogenase (G6PD) or pyruvate kinase deficiency (PKD), and hemoglobinopathies such as thalassemia and sickle cell. Some studies have suggested an association between iron metabolism disorders, such as thalassemia and hemochromatosis, and a number of disease states, such as type II (non-insulin dependent) diabetes mellitus and atherosclerosis (A. J. Matthews et al., J. Surg. Res., 1997, 73: 3540: T. P. Tuomainen et al., Diabetes Care, 1997, 20: 426-428).

Studies also suggest that iron metabolism plays a role in a number of other diseases states, including cardiovascular disease (see, for example, P. Tuo mainen et al., Circulation, 1997, 97: 1461-1466: J. M. McCord, Circulation, 1991, 83: 1112-1114; J. L. Sullivan, J. Clin. Epidemiol., 1996, 49: 1345-1352).

The role of hepcidin and iron in neurological conditions has recently been proposed. For example, increased hepcidin levels have been shown in various neurological diseases including, for example, focal brain ischemia/reperfusion, intracerebral hemorrhage, subarachnoid hemorrhage, acute ischemic stroke, ischemic stroke, Alzheimers disease, Parkinson disease, amyotrophic lateral sclerosis (ALS), and chronic mild stress (Vela et al., *J Transl Med* 2018; 16:25).

Additionally, iron metabolism may also play a key role in restless legs syndrome (Daubian-Nose P. et al., *Sleep Sci* 2014; 7(4):234-7 and Connor et al., *Sleep Medicine* 2017; 31:61-70). Indeed, increased pro-hepcidin levels have been shown in brain tissue of patients having restless leg syndrome, while decreased pro-hepcidin levels were observed in cerebrospinal fluid in early-onset disease (Clardy et al., *J Neurol Sci* 2006; 247:173-9). Iron depots in the brain of RLS patients are low and related with higher expression of brain hepcidin (Rizzo G. et al, *Mov Disord* 2013; 28:1886-90 and Clardy et al., *J Neurol Sci* 2006; 247:173-9). Low levels of iron in the brain of RLS patients persists even in the presence of HH (Haba-Rubio J. et al., *J Neurol Neurosurg Psychiatry* 2005; 76:1009-10). Furthermore, transferrin receptor expression in the brain microvasculature of RLS patients is low, suggesting low iron transport across the BBB (Connor J R et al., *Brain* 2011; 134:959-68). Interestingly, restless legs syndrome has been suggested as a comorbidity in rheumatoid arthritis—both diseases having links to iron dysregulation (John A. Gjevre and Regina M. Taylor Gjevre, Autoimmune Diseases 2013; Article ID 352782).

i. Iron-Refractory Iron Deficiency Anemia (IRIDA)

Iron-refractory iron deficiency anemia is an autosomal recessive disorder caused by mutations in Tmprss6. TMPRSS6 is a negative regulator of hepcidin by cleaving membrane bound RGMc to produce a soluble RGMc (s-RGMc) which acts as a decoy receptor for BMP6. Reduced BMP6 signaling leads to a reduction in Hepcidin expression. Thus, mutations that inhibit TMPRSS6 function promote the accumulation of membrane-bound RGMc, which leads to increases in Hepcidin expression and iron-deficiency anemia. Patients having IRIDA have too little iron in their blood, which causes red blood cells to be small in size (microcytic) and pale in color (hypochromic). Other phenotypes of the disease may include low transferrin saturation, low serum ferritin, and low serum iron levels. Unfortunately, the high levels of hepcidin in these patients render them refractory to oral iron administration.

Given the well-defined mechanism of IRIDA results in an increase in membrane-bound RGMc (and increased hepcidin levels), agents that specifically bind to RGMc and reduce hepcidin levels, while limiting potential side effects of targeting related RGM proteins (e.g., RGMa and RGMb), would be beneficial.

Accordingly, an RGMc-selective inhibitor (e.g., monoclonal antibodies disclosed herein, derivatives thereof, monoclonal antibodies that competes therewith, and engineered molecules comprising an antigen-binding fragment thereof) may be used for the treatment of IRIDA in a subject (e.g., human patient). Thus, in one aspect, methods for treating, preventing, or ameliorating symptoms associated with IRIDA are disclosed. In one embodiment, the method comprises administering an RGMc antagonist to a patient having IRIDA. In another embodiment, the method comprises administering to a patient having IRIDA antibodies that specifically bind to RGMc and inhibit its function. In another embodiment, the RGMc-specific antibody does not bind (or has reduced binding) to RGMa and/or RGMb. In another embodiment, the RGMc-specific antibody is any one of the RGMc-specific antibodies described herein or any derivatives thereof. In some embodiments, the RGMc-specific (RGMc-selective) antibody competes (e.g., cross-competes or cross-blocks) antigen binding with one or more of the RGMc antibodies disclosed herein.

ii. Anemia of Chronic Disease (ACD)

Anemia of chronic disease (e.g., anemia of chronic inflammation) is a form of anemia that is the result of chronic infection, chronic immune activation (e.g., inflammation), and/or malignancy, etc., and is the most common form of anemia in hospitalized patients.

Typically, ACD starts with an inflammatory response, followed by an inflammatory cytokine release mediating disease progression. The cytokines reduce production of erythrocytes, facilitate lysis of erythrocytes, and stimulate macrophages to store and retain iron as ferritin which ultimately leads to insufficient iron availability. Moreover, there is a massive elevation of interleukin-6 (IL-6) which stimulates hepcidin expression, which in turn induces degradation of ferroportin thereby blocking iron release from macrophages and enterocytes into the circulation. In addition to the inflammatory response, other mechanisms may also play a role in ACD, e.g., reduced erythropoiesis by decreasing the ability of the bone marrow to response to erythropoietin.

As suggested above, there are many conditions that can cause inflammation that leads to anemia, including: autoimmune diseases, e.g., rheumatoid arthritis (RA) or lupus, cancer, chronic infections, e.g., HIV/AIDS and tuberculosis, chronic kidney disease (CKD), gastrointestinal inflammatory conditions such as inflammatory bowel disease (IBD), including Crohn's disease and ulcerative colitis, diabetes, and heart failure. While inflammatory anemias are generally slow to develop, anemia of critical illness can develop quickly in patients who are hospitalized for severe acute infections, trauma, or other conditions that may cause inflammation. Moreover, particular drug treatments, such as chemotherapy, can quickly induce inflammation and anemia.

Other anemia-related inflammatory diseases may include, for example, Castleman's Syndrome, Chronic Kidney Disease, Diabetes, Heart Failure/Heart Disease, Idiopathic Autoimmune Hemolytic Anemia, Idiopathic Pulmonary Arterial Hypertension, Inflammatory Bowel Disease, Rheumatoid Arthritis, Systemic Lupus Erythematosus, and Systemic Juvenile Idiopathic Arthritis. Infectious diseases causing anemia may include, for example, endocarditis, *Helicobacter pylori* infection, hepatitis, human immunodeficiency virus, and malaria. Neurological diseases associate with anemia may include, for example, acute ischemic stroke, amyotrophic lateral sclerosis, focal brain ischemia/reperfusion, intracranial cerebral hemorrhage, and subarachnoid hemorrhage.

Accordingly, an RGMc-selective inhibitor (e.g., monoclonal antibodies disclosed herein, derivatives thereof, monoclonal antibodies that competes therewith, and engineered molecules comprising an antigen-binding fragment thereof) may be used for the treatment of ACD (such as one or more of the ACD indications included herein) in a subject (e.g., human patient). Thus, in one aspect, methods for treating (e.g., preventing, or ameliorating symptoms associated with) anemia of chronic disease (ACD) in human patients are disclosed. In some embodiments, the method comprises administering an RGMc antagonist to a patient having ACD. In some embodiments, the method comprises administering to a patient having ACD antibodies that specifically bind to RGMc and inhibit its function. In some embodiments, the RGMc-specific (RGMc-selective) antibody does not bind (or has reduced binding) to RGMa and/or RGMb. In some embodiments, the RGMc-specific antibody is any one of the RGMc-specific antibodies described herein, or any derivatives thereof. In some embodiments, the RGMc-specific (RGMc-selective) antibody competes (e.g., cross-competes or cross-blocks) antigen binding with one or more of the RGMc antibodies disclosed herein.

iii. Cancer-Related Anemia

Approximately 30-90% of cancer patients are affected by anemia (Knight et al., *Am J Med* 2004; 116 Suppl 7A:11S-26S). For example, approximately 32% of non-Hodgkin's lymphoma patients, and 49% of gynecologic cancer patients have anemia at diagnosis. (Moullet et al., *Ann Oncol* 1998; 8:1109-1115 and Ludwig et al., *Eur J Cancer* 2004; 40:2293-2306). The anemia may be caused by factors related to the cancer itself (Cancer-induced anemia), or as a consequence of chemotherapy (chemotherapy-induced anemia). Moreover, radiation therapy to the skeleton has been shown to be associated with hematologic toxicity (Jefferies et al., *Radiother Oncol* 1998; 48:23-27). The pathology of the anemia can be grouped into three categories: 1) decreased production of function red blood cells (RBCs); 2) increased destruction of RBCs; and 3) blood loss. However, the causes of anemia can be multifactorial, which may complicate evaluation and treatment. The anemia may be caused by bleeding, hemolysis, nutritional deficiencies, hereditary disease, renal insufficiency, hormone dysfunction and/or a combination thereof. Additionally, the cancer cells themselves may lead to and/or exacerbate anemia by infiltrating the bone marrow, produce cytokines that lead to iron sequestration (leading to reduced RBC production), shorten RBC survival, and/or changes in coagulation.

Moreover, cancer patients may also experience chronic blood loss at the tumor site from blood vessels or organ damage. Other contributing factors to anemia in cancer patients may include, loss of appetite, hemolysis by immune-mediated antibodies, or changes in coagulation capability.

Finally, anemia also has been identified as an adverse prognostic factor in cancer patients. For example, it has been predicted that there is a 65% increased risk of death and close to a four-fold higher average annual health care cost per patient. Accordingly, the goals of treating anemia in cancer patients are to improve patients' quality of life (QoL) and reduce reliance on blood transfusions. Blood transfusions are associated with the potential risk of transmission of infectious disease, transfusion reactions, lung injury, and alloimmunisation. Transfusions may also increase the risk of mortality and morbidity including stroke, myocardial infarction, acute renal failure and recurrence of cancer (Annals of Oncology 21 (Supplement 7): vii167-vii172, 2010; PLOS ONE, DOI: 10.1371/journal.pone.0163817 (Sep. 28, 2016); Annals of Oncology 23:1954-1962, 2012; and Annals of Clinical & Laboratory Science, vol. 47, no. 2, 2017).

The term "cancer" as used herein refers to the physiological condition in multicellular eukaryotes that is typically characterized by unregulated cell proliferation and malignancy. The term broadly encompasses, solid and liquid malignancies, including tumors, blood cancers (e.g., leukemias, lymphomas and myelomas), as well as myelofibrosis. Cancers causing anemia may include, for example, Acute Leukemia, Diffuse Large B-cell Lymphoma, Hodgkin's Lymphoma, lymphocytic leukemia, Multiple Myeloma, Myelodysplastic Syndrome, myeloproliferative disorders (e.g., myelofibrosis), Non-Hodgkin's Lymphoma, Waldenstrom macroglobulinemia, Bladder, Breast, Colorectal, Gastric, Head and Neck, Hepatocellular, Lung, Ovarian, Prostate, Pancreatic, Brain, Hepatocellular, Renal Cell, testicular, and thyroid (Maccio et al., *Haematologica* 2015; 100(1): 124-132 and Vela et al., *Exp & Mol Medicine* 2018; 50:e436.

Accordingly, an RGMc-selective inhibitor (e.g., monoclonal antibodies disclosed herein, derivatives thereof, monoclonal antibodies that competes therewith, and engineered molecules comprising an antigen-binding fragment thereof) may be used for the treatment of cancer-induced or cancer-associated anemia in a subject (e.g., human patient). Thus, in one aspect, methods for treating (e.g., preventing, or ameliorating symptoms associated with) cancer-induced anemia. In some embodiments, the method comprises administering an RGMc antagonist to a patient having cancer-induced anemia. In some embodiments, the cancer is Acute Leukemia, Diffuse Large B-cell Lymphoma, Hodgkin's Lymphoma, lymphocytic leukemia, Multiple Myeloma, Myelodysplastic Syndrome, Non-Hodgkin's Lymphoma, Waldenstrom macroglobulinemia, Bladder cancer, Breast cancer, Colorectal cancer, Gastric cancer, Head and Neck cancer, Hepatocellular cancer, Lung cancer, Ovarian cancer, Prostate cancer, Pancreatic cancer, Brain cancer, Renal Cell cancer, testicular cancer, thyroid cancer, or myelofibrosis. In some embodiments, the method comprises administering to the patient an antibodies that specifically bind to RGMc and inhibit its function. In some embodiments, the RGMc-specific antibody does not bind (or has reduced binding) to RGMa and/or RGMb. In some embodiments, the RGMc-specific antibody is any one of the RGMc-specific antibodies described herein or any derivatives thereof. In some embodiments, the RGMc-specific (RGMc-selective) antibody competes (e.g., cross-competes or cross-blocks) antigen binding with one or more of the RGMc antibodies disclosed herein.

iv. Treatment-Induced Anemia

Various therapies administered to patients are associated with unwanted side effects that include anemia in treated patients. In some cases, patients may already suffer from anemia but therapies they receive may further exacerbate the condition.

A significant fraction of patients who receive cancer treatment, such as chemotherapy and radiation therapy, experience treatment-induced anemia. Typically, these therapies are aimed to kill cancerous cells in the body but also affect healthy cells, including blood cells (e.g., hematopoietic cells and hematopoietic stem cells), which result in anemia.

Chemotherapeutic agents have been shown to induce anemia by directly impairing hematopoiesis in the bone marrow. Additionally, the effects of cytotoxic on kidney function can lead to anemia through decreased production of erythropoietin. In particular, platinum-based regimens which are commonly used in lung, ovarian, and head and neck cancers are known to induce anemia through bone marrow and kidney toxicities. (Groopman et al., *J Natl Cancer Inst* 1999; 91:1616-1634). Moreover, repeated cycles of chemotherapy have also been shown to increase the severity of anemia in these patients (Ludwig et al., *Eur J Cancer* 2004; 40:2293-2306).

Interestingly, recent data suggests that immunotherapies may also be causing (and/or increases the risk of) anemia in cancer patients. For example, a recent study identified hemolytic anemia as a potential complication of treatment with nivolumab (an anti-PD-1 antibody) (Palla et al., *Case Rep Oncol* 2016; 9:691-697). Other cases of autoimmune hemolytic anemia have been reported after use of nivolumab, including instances of anemia in patients receiving ipilimumab (an anti-CTLA-4 antibody) and pembrolizumab (an anti-PD-1 antibody). Accordingly, anemia that is caused, or has an increased chance/risk of occurring, by the administration of anti-cancer agents/drugs, including immunotherapies, are encompassed by the term "chemotherapy-induced anemia".

Finally, as noted above, the presence of anemia has been implicated as a prognostic factor for cancer survival (Caro J J et al., *Cancer* 2001 15; 91(12):2214-21). Accordingly, there is a strong rational to treat anemia in cancer patients, or patients undergoing chemotherapy, since it may result in improved outcomes. Moreover, in view of the well-described link between cancer, chemotherapy, and anemia, the National Comprehensive Cancer Network (NCCN) periodically releases guidelines for the diagnosis, evaluation, and treatment of cancer- and chemotherapy-induced anemia (see, e.g., Rodgers et al, Cancer- and Chemotherapy Induced Anemia, *JNCCN* 2012; 10:628-53).

Accordingly, an RGMc-selective inhibitor (e.g., monoclonal antibodies disclosed herein, derivatives thereof, monoclonal antibodies that competes therewith, and engineered molecules comprising an antigen-binding fragment thereof) may be used for the treatment of treatment-induced anemia (such as chemotherapy-induced anemia) in a subject (e.g., human patient).

Thus, in one aspect, methods for treating, preventing, or ameliorating symptoms associated with chemotherapy-induced anemia are provided. In one embodiment, the method comprises administering an RGMc antagonist to a patient having chemotherapy-induced anemia.

In another embodiment, the method comprises administering to the patient an antibodies that specifically bind to RGMc and inhibit its function. In another embodiment, the RGMc-specific antibody does not bind (or has reduced binding) to RGMa and/or RGMb. In another embodiment, the RGMc-specific antibody is any one of the RGMc-specific antibodies described herein or any derivatives thereof. In some embodiments, the RGMc-specific (RGMc-selective) antibody competes (e.g., cross-competes or cross-blocks) antigen binding with one or more of the RGMc antibodies disclosed herein.

v. Chronic Kidney Disease (CKD)

Anemia is a common complication associated with chronic kidney disease (CKD). Indeed, approximately 14% of the U.S. adult population had CKD in 2007-2010 and anemia was nearly twice as prevalent in people with CKD, 15.4% in CKD patient versus 8.4% in the general population (Stauffer and Fan, PLoS One 2014; 9:e84943).

While the kidneys are well-known to act as filters of the blood, removing waste products and controlling the balance of fluid and electrolytes, a lesser known role of the kidneys is to produce erythropoietin which stimulates red blood cell production. Thus, perturbations in kidney function have the potential to produce anemia. Moreover, the underlying inflammation in CKD patients may also cause and/or exacerbate anemia in these patients.

CKD is characterized by the gradual loss of kidney function over a period of time (months or years). Causes of CKD include, for example, diabetes, high blood pressure, glomerulonephritis, and polycystic kidney disease. However, there are also idiopathic cases (i.e., having unknown causes), which are often associated with small kidneys.

Treatment to slow or halt the progression of CKD usually entails treating the original diseases, however controlling blood pressure with angiotensin converting enzyme inhibitors or angiotensin II receptor antagonists are a common treatment since they have been found to slow the progression of disease. However, in severe cases (e.g., end-stage kidney disease), the patient will have to undergo dialysis or even kidney transplant. The patient may be dialysis-dependent (for example, chronic hemodialysis patients); the patient may be non-dialysis-dependent.

CKD patients with anemia may be treated with oral or intravenous iron. In certain cases, treatment may include injections of a genetically engineered form of erythropoietin (EPO) and/or blood transfusions. However, iron replacement is not always effective; for example, some patients are or develop hyporesponsiveness to ESA therapies. Moreover, ESAs such as EPO treatment have been associated with increased chance of cardiovascular events, such as heart attack and stroke. Thus, improved therapies that can regulate iron levels with reduced side effects are needed.

Accordingly, an RGMc-selective inhibitor (e.g., monoclonal antibodies disclosed herein, derivatives thereof, monoclonal antibodies that competes therewith, and engineered molecules comprising an antigen-binding fragment thereof) may be used for the treatment of cancer-induced or cancer-associated anemia in a subject (e.g., human patient). Thus, in one aspect, methods for treating, preventing, or ameliorating symptoms associated with chronic kidney disease (e.g., anemia) are provided. In one embodiment, the method comprises administering an RGMc antagonist to a patient having chronic kidney disease. In another embodiment, the method comprises administering to the patient an antibodies that specifically bind to RGMc and inhibit its function. In another embodiment, the RGMc-specific antibody does not bind (or has reduced binding) to RGMa and/or RGMb. In another embodiment, the RGMc-specific antibody is any one of the RGMc-specific antibodies described herein or any derivatives thereof. In some embodiments, the RGMc-specific (RGMc-selective) antibody competes (e.g., cross-competes or cross-blocks) antigen binding with one or more of the RGMc antibodies disclosed herein.

In any of the above embodiments in the treatment of anemia, or disease characterized by or associated with anemia, the RGMc inhibitor therapy described herein may partially or fully replace current or standard therapy or therapies administered to patients, such as ESAs, HIF stabilizers, iron supplements (e.g., IV iron) and blood transfusion. In some embodiments, addition of the RGMc inhibitor therapy in the therapeutic regiments in accordance with the present disclosure allows the patients to receive reduced dosage or administration frequency of such treatment. This may relieve or avoid unwanted side effects or other risks such as iron overload in the patients. In some embodiments, RGMc inhibitor therapy may fully replace other therapies to treat anemia in patients.

In any of the above embodiments in the treatment of anemia or disease characterized by or associated with anemia, the RGMc inhibitor therapy described herein may be used in conjunction with another therapy as an add-on or adjuvant therapy. In certain embodiments, patients may receive or continue to receive other therapy to treat anemia but at lower dose or less frequency. In some embodiments, patients who are resistant to or poorly responsive to such therapy may be rendered more responsive (e.g., sensitized) to the therapy when treated with the RGMc inhibitor in conjunction with the therapy.

Selection of Subjects for Treatment with RGMc Inhibitors

The methods of treatment described herein, may also include the step of measuring one or more factors to determine the presence and/or severity of disease (e.g., anemia) in a subject. Generally, the definition of anemia is Hb<12 g/dl in women and Hb<13 g/dl in males. While measuring hemoglobin is accepted as one measure of anemia, determining the type (AID or FID) and cause of the anemia may involve many different tests. For example, there are several well-known tests which can aid in determining the type and severity of anemia in a subject, including but not limited to, measurements of hemoglobin (Hb), serum ferritin (SF), transferrin saturation (TSAT), soluble transferrin receptor (sTfR), ferritin index (FI=sTfR/log SF), hypochromic reticulocytes (CHR) and C-reactive protein (CRP). Mean corpuscular volume (MCV) or mean corpuscular hemoglobin concentration (MCHC) are also measurements which may correlate with anemia type.

The exact criteria for defining AID and FID is the subject of debate and vary depending on the study, disease, sex and authority. For example, without being bound to a particular theory, FID may be defined as 1) serum transferrin saturation (TSAT)<20% and ferritin ≥100 ng/mL (Ludwig et al., *Ann Oncol* 2013; 24(7):1886-1892); 2) TSAT <16% and ferritin >100 ng/ml (mild) or serum ferritin 30-100 ng/ml (moderate) (Bach et al., *Clinical Interventions In Aging* 2014; 9:1187-1196); 3) TSAT 20-50% and ferritin 30-800 ng/ml (Gilreath et al., *Am J Hematol* 2014; 89(2):203-212); 4) TSAT <20% and ferritin >30 ng/ml and >100 ng/ml in cancer patients (Ludwig et al., *Wien Klin Wochenschr* 2015; 127:907-919) or 5) TSAT <20% and ferritin >30 ng/ml (women) or >40 ng/ml (men) (Hedenus et al., *Med Oncol* 2014; 31(12):302). In other cases, percent hypochromic red cells can be used to detect FID (see, e.g., Bovy et al., *Nephrol Dial Tranplant* 2007; 22(4):1156-1162 and Murphy et al., *Ann Hematol* 2006; 85(7):455-457). In other cases, FID is defined as when a patient had Hb<110 g/l, iron-restricted erythropoiesis (% hypochromia >5), systemic inflammation (CRP >10), and optionally ferritin value of 30-800 ng/ml (Neoh et al., *Support Care Cancer* 2017; 25:1209-1214).

On the other hand, without being bound by a particular theory, AID may be defined, for example, as 1) TSAT <20% and ferritin <30 ng/ml (Ludwig et al., *Ann Oncol* 2013; 24(7):1886-1892); 2) TSAT <20% and ferritin <100 ng/ml in cancer patients (Ludwig et al., *Wien Klin Wochenschr* 2015; 127:907-919); or 3) TSAT <20% and ferritin levels <40 ug/L (Hashemi et al., *Int J Hematol Oncol Stem Cell Res* 2017; 11(3):192-198).

The methods of treatment can also involve the measurement of other markers as discussed herein and known in the art. For example, measurement of hepcidin (see, e.g., US20150202224A1 and Kroot et al. *Clinical Chemistry* 2011; 57(12):1650-1669), neogenin, growth differentiation factor 15 (GDF-15), neutrophil gelatinase-associated lipocalin (NGAL), interleukin 6 (IL-6), and/or BMP6.

Additionally, the identification of other risk factors and/or diseases may aid in determining the presence and type of anemia, for example, the patient may have an infection, cancer, or chronic kidney disease. Genetic tests may also be helpful for determining particular iron-related diseases, for example, iron-refractory iron deficiency anemia (IRIDA), thalassemia, hereditary spherocytosis, hereditary elliptocytosis, abetalipoproteinemia, sickle cell anemia, congenital dyserythropoietic anemia, hereditary hemochromatosis (HH), and juvenile hemochromatosis.

The subject in any of the methods described herein, may be a subject having, diagnosed with, suspected of having, or at risk for developing iron deficiency anemia or a disease, disorder, or condition associated with iron deficiency anemia. The subject may be a mammal, which may be a human or anon-human. In a particular embodiment, the subject is a human subject. In another embodiment, the subject can be a human male subject. In another embodiment, the subject can be a human female subject. In another embodiment, the subject may be a critical care patient, undergoing chemotherapy, recovering from surgery, or may be at risk for, or have, an infection, cancer, an autoimmune disease or disorder, chronic organ disease and/or inflammation, and/or chronic rejection of an organ after solid organ transplantation. The infection may be acute or chronic. The infection may be viral, bacterial, parasitic, or fungal. The cancer may be any cancer, such as hematologic or a solid tumor. The autoimmune disease may be any autoimmune disease, such as rheumatoid arthritis, systemic lupus erythematosus and connective tissue diseases, vasculitis, sarcoidosis, and inflammatory bowel disease. The chronic organ disease may be chronic kidney disease, in which the subject may or may not be undergoing dialysis. The viral infection may be hepatitis B or C infection, or human immunodeficiency virus infection. Any of the diseases and disorders may be an underlying cause of ACD. The surgery may be perioperative or postoperative. The surgery may be oncologic surgery.

A subject in need for treatment will typically be assessed by a history and physical exam consistent with the disease or condition at issue. Diagnosis of the various conditions treatable by the methods described herein is within the skill of the art. An RGMc antagonist described herein can be administered to a subject where there is a clinical need to deliver iron or in subjects with functional iron deficiency such as those on erythropoietin therapy. A determination of the need for treatment with parenteral or i.v. iron is within the abilities of one skilled in the art. For example, need can be assessed by monitoring a subject's iron status. The diagnosis of iron deficiency can be based on appropriate laboratory tests, as described above, for example, Hg level according to Table 2 or >2 g/dl below baseline and/or red blood cells with an MCV of less than 80 femtoliters (fL).

Other measurements to diagnosis iron deficiency can be based on measurements of serum ferritin (SF), transferrin saturation (TSAT), soluble transferrin receptor (sTfR), ferritin index (FI =sTfR/log SF), hypochromic reticulocytes (CHR), C-reactive protein (CRP), mean corpuscular volume (MCV) and/or mean corpuscular hemoglobin concentration (MCHC).

TABLE 2

WHO hemoglobin thresholds as of 2011

| Age or gender group | Hb threshold (g/dl) |
| --- | --- |
| Children (0.5-5.0 yrs) | 11.0 |
| Children (5-12 yrs) | 11.5 |
| Teens (12-15 yrs) | 12.0 |
| Women, non-pregnant (>15 yrs) | 12.0 |
| Women, pregnant | 11.0 |
| Men (>15 yrs) | 13.0 |

A subject in need of treatment can be also be determined through diagnosis of a subject suffering from a disease, disorder, or condition that is associated with iron deficiency anemia. For example, many chronic renal failure patients receiving erythropoietin will require an iron agent to maintain target iron levels. As another example, most hemodialysis patients will require administration of an iron agent due to dialysis-associated blood loss and resulting negative iron balance.

Monitoring frequency can depend upon the disease, disorder, or condition the subject is afflicted with or at risk for. For example, in a subject initiating erythropoietin therapy, iron indices are monitored monthly. As another example, in subject who have achieved target range Hb or are receiving intravenous iron therapy, TSAT and ferritin levels can be monitored every 3 months.

A subject's iron status can be indicative of an absolute iron deficiency (AID) or a functional iron deficiency (FID), both of which can be treated with the compositions and therapeutic methods described herein. An absolute iron deficiency occurs when an insufficient amount of iron is available to meet the body's requirements. The insufficiency may be due to inadequate iron intake, reduced bioavailability of dietary iron, increased utilization of iron, or chronic blood loss. Prolonged iron deficiency can lead to iron deficiency anemia—a microcytic, hypochromic anemia in which there are inadequate iron stores. AID is generally indicated where TSAT <20% and Ferritin <100 ng/mL.

TSAT is the ratio of serum iron and total iron-binding capacity, multiplied by 100. Of the transferrin that is available to bind iron, the TSAT value tells a clinician how much serum iron is actually bound. For example, a value of 15% means that 15% of iron-binding sites of transferrin is being occupied by iron FID can occur where there is a failure to release iron rapidly enough to keep pace with the demands of the bone marrow for erythropoiesis, despite adequate total body iron stores. In these cases, ferritin levels may be normal or high, but the supply of iron to the erythron is limited, as shown by a low transferrin saturation and an increased number of microcytic, hypochromic erythrocytes. FID can be characterized by the following characteristics: Inadequate hemoglobin response to erythropoietin; Serum ferritin may be normal or high; Transferrin saturation (TSAT) usually <20%; and/or reduced mean corpuscular volume (MCV; e.g., less than 80 fL) or mean corpuscular hemoglobin concentration (MCHC; e.g., less than 34±2 g/dl) in severe cases. Functional iron deficiency (i.e., iron stores are thought to be adequate but unavailable for iron delivery) is generally indicated where TSAT<20% and Ferritin>100 ng/mL.

Assessing the need for iron therapy can be according to, for example, the National Kidney Foundation's Kidney Disease Outcomes Quality Initiative. See NKF-K/DOQI, Clinical Practice Guidelines for Anemia of Chronic Kidney Disease (2000); Am J Kidney Dis (2001) 37(supp 1), S182-S238. The DOQI provides optimal clinical practices for the treatment of anemia in chronic renal failure. The DOQI guidelines specify intravenous iron treatment of kidney disease based on hemoglobin, transferrin saturation (TSAT), and ferritin levels.

Additional guidelines for iron management and determining AID vs FID in cancer and/or chemotherapy patients have also been suggested, for example, see Steinmetz et al., *Ther Adv Hematol* 2012; 3(3):177-91, Mikhael et al., *Curr Oncol* 2007; 14:209-217, European Organization for Research and Treatment of Cancer (EORTC; Bokemeyer et al., *Eur J Cancer* 2007; 43:258-270; and Aapro and Link, *Oncologist* 2008; 13(Suppl. 3):33-36), American Society of Hematology (ASH) and the American Society of Clinical Oncology (ASCO) (see, e.g., Rizzo et al., *Blood* 2010; 100:2303-2320), National Comprehensive Cancer Network (NCCN) guidelines version 3.2018 Cancer- and Chemotherapy-induced Anemia, European Society for Medical Oncology (ESMO) (see, e.g., Aepro et al., *Annals of Oncology* 2018; 0:1-15) and National institute for Health and Care Excellence (NICE) (see, e.g., Technology appraisal guidance published 26 Nov. 2014; nice.org.uk/guidance/ta323).

A subject in need of treatment may be determined by a subject's target iron level. For example, the target hemoglobin level of a subject can be selected as 11.0 g/dL to 12.0 g/dL (hematocrit approximately 33% to 36%). To achieve target hemoglobin with optimum erythropoietin doses, sufficient iron, can be provided to maintain TSAT 20% and ferritin 100 ng/mL. Achievement of target hemoglobin levels with optimum erythropoietin doses is associated with providing sufficient iron to maintain TSAT above 20%.

Iron therapy can be given to maintain target hemoglobin while preventing iron deficiency and also preventing iron overload. Adjusting dosage of iron to maintain target levels of hemoglobin, hematocrit, and laboratory parameters of iron storage is within the normal skill in the art. For example, where a subject is anemic or iron deficient, an iron agent can be administered when a patient has a ferritin <800 ng/mL, a TSAT <50%, and/or a Hemoglobin <12 g/dL. Iron overload can be avoided by withholding iron for TSAT >50% and/or ferritin >800 ng/mL.

Where a subject is not anemic or iron deficient but is still in need of an RGMc antagonist, for example a subject suffering from Restless Leg Syndrome, hemoglobin and TSAT levels are not necessarily relevant, while ferritin >800 can still provide a general cut off point for administration.

Administration

To practice the method disclosed herein, an effective amount of the pharmaceutical composition described above can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, antibodies, or antigen-binding fragments thereof, that specifically bind a RGMc can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a RGMc-related indication, such as those noted above (e.g., anemia). A subject having a RGMc-related indication can be identified by routine medical examination, e.g., laboratory tests, organ functional tests, CT scans, or ultrasounds. A subject suspected of having any of such indication might show one or more symptoms of the indication. A subject at risk for the indication can be a subject having one or more of the risk factors for that indication.

As used herein, the terms "effective amount" and "effective dose" refer to any amount or dose of a compound or composition that is sufficient to fulfill its intended purpose(s), i.e., a desired biological or medicinal (clinical) response in a tissue or subject at an acceptable benefit/risk ratio. For example, in certain embodiments of the present invention, the intended purpose may be to inhibit RGMc activity in vivo, to achieve clinically meaningful outcome associated with the RGMc inhibition. For example, clinically meaning effects may include, increased serum iron, restoration or normalization of hemoglobin or red blood cell counts, increased transferrin saturation, etc. In some embodiments, clinically meaningful effects may include reduced toxicities or risk of harm such as cardiovascular risk (e.g., stroke or heart failure) and cancer. In some embodiments, clinically meaningful effects may include reduced needs for other therapies such as iron supplements. In some embodiments, clinically meaningful effects may include improved quality of life or general well being perceived by patients. In some embodiments, clinically meaningful effects may include accelerate or faster relief of one or more parameters indicative of anemia. Such relief may be achieved by an add-on or combination therapy comprising the RGMc inhibitor and another therapy (e.g., ESAs, HIF stabilizers, etc.). For instance, typically, when EPO therapy (e.g., monotherapy) is commenced, it takes 1-2 months (e.g., 6-8 weeks) for the treatment to show effects. For this reason, patients experiencing severe anemia may additionally require IV iron or transfusion during that time. Used in conjunction with an RGMc selective inhibitor such as those disclosed herein, however, the onset of therapeutic effects may be significantly more rapid (e.g., 1-4 weeks), which may reduce the need for additional IV iron or transfusion.

Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of an RGMc-related indication. Alternatively, sustained continuous release formulations of an antibody that specifically binds RGMc may be appropriate. Various formulations and devices for achieving sustained release would be apparent to the skilled artisan and are within the scope of this disclosure.

In one example, dosages for an antibody that specifically binds RGMc as described herein may be determined empirically in individuals who have been given one or more administration(s) of the antibody. Individuals are given incremental dosages of the RGMc antagonist. To assess efficacy, an indicator of the RGMc-related indication can be followed. For example, methods for measuring anemia are well known in the art and are described further herein.

The present invention encompasses the recognition that agents capable of specifically modulating RGMc signaling, as opposed to RGMa and/or RGMb, may provide improved safety profiles when used as a medicament. Accordingly, the invention includes antibodies and antigen-binding fragments thereof that specifically bind and inhibit activation of RGMc, but not RGMa and/or RGMb, thereby conferring specific inhibition of RGMc signaling in vivo while minimizing unwanted side effects from affecting RGMa and/or RGMb signaling.

In some embodiments, the antibodies, or antigen-binding fragments thereof, as described herein, are not toxic when administered to a subject. In some embodiments, the antibodies, or antigen-binding fragments thereof, as described herein, exhibit reduced toxicity when administered to a subject as compared to an antibody that specifically binds to both RGMc and RGMa. In some embodiments, the antibodies, or antigen-binding fragments thereof, as described herein, exhibit reduced toxicity when administered to a subject as compared to an antibody that specifically binds to both RGMc and RGMb. In some embodiments, the antibodies, or antigen-binding fragments thereof, as described herein, exhibit reduced toxicity when administered to a subject as compared to an antibody that specifically binds to RGMa, RGMb and RGMc.

Generally, for administration of any of the antibodies described herein, an initial candidate dosage can be about 0.1-20 mg/kg, for example, 1-20 mg/kg per administration, e.g., weekly, every 2 weeks, every 3 weeks, monthly, every three months, etc. For example, patients may receive an injection of about 1-10 mg/kg per 1 week, per 2 weeks, per 3 weeks, or per 4 weeks, etc., in an amount effective to treat a disease (e.g., cancer) wherein the amount is well-tolerated (within acceptable toxicities or adverse events).

For the purpose of the present disclosure, a typical dosage (per administration, such as an injection and infusion) might range from about any of 0.1 mg/kg to 1 mg/kg to 2 mg/kg to 3 mg/kg to 5 mg/kg to 10 mg/kg to 20 mg/kg to 30 mg/kg or more, depending on the factors mentioned above. For repeated administrations over several days or longer, depending on the condition, the treatment is sustained until a desired suppression of symptoms occurs or until sufficient therapeutic levels are achieved to alleviate an RGMc-related indication, or a symptom thereof.

An exemplary dosing regimen comprises administering an initial dose, followed by one or more of maintenance doses, wherein the latter is typically lower than the former. For example, an initial dose may be between about 2 and 30 mg/kg, for instance, once a week or twice a week. Thereafter, maintenance dose(s) may follow, for example, between about 0.1 and 20 mg/kg (e.g., 1, 2, 3, 5, 10, 15 mg/kg), for instance, once a week, every other week, once a month, etc. However, other dosage regimens may be useful, depending on the pattern of pharmacokinetic decay that the practitioner wishes to achieve. Pharmacodynamic (PD) experiments have shown that there is a sustained PD effect (e.g., increased serum iron levels) for at least 3 weeks after administration of an antibody disclosed herein (e.g., Ab8; 20 mg/kg) to a preclinical animal model (e.g., a rat model). Without wishing to be bound by any particular theory, this sustained effect post-administration may be advantageous since the antibody may be administered less frequently while maintaining a clinically effective serum concentration in the subject to whom the antibody is administered (e.g., a human subject). In some embodiments, dosing frequency is once every week, every 2 weeks, every 3 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

In some embodiments, for an adult patient of normal weight, doses ranging from about 0.3 to 5.00 mg/kg may be administered. The particular dosage regimen, e.g., dose, timing and repetition, will depend on the particular individual and that individual's medical history, as well as the properties of the individual agents (such as the half-life of the agent, and other relevant considerations).

For the purpose of the present disclosure, the appropriate dosage of an antibody that specifically binds RGMc will depend on the specific antibody (or compositions thereof) employed, the type and severity of the indication, whether the antibody is administered for preventive or therapeutic purposes, previous therapy, the patient's clinical history and response to the antagonist, and the discretion of the attending physician. In some embodiments, a clinician will administer an antibody that specifically binds RGMc, until a dosage is reached that achieves the desired result. Administration of an antibody that specifically binds RGMc can be continuous or intermittent, depending, for example, upon the recipient's physiological condition, whether the purpose of the administration is therapeutic or prophylactic, and other factors known to skilled practitioners. The administration of antibody that specifically binds RGMc may be essentially continuous over a preselected period of time or may be in a series of spaced dose, e.g., either before, during, or after developing a RGMc-related indication (e.g., anemia).

As used herein, the term "treating" refers to the application or administration of a composition including one or more active agents to a subject, who has an RGMc-related indication, a symptom of the indication, or a predisposition toward the indication, with the purpose to cure, heal, alleviate, relieve, alter, remedy, ameliorate, improve, or affect the indication, the symptom of the indication, or the predisposition toward the indication.

Alleviating a RGMc-related indication with an antibody that specifically binds RGMc includes delaying the development or progression of the indication, or reducing indication's severity. Alleviating the indication does not necessarily require curative results. As used therein, "delaying" the development of an indication associated with a RGMc-related indication means to defer, hinder, slow, retard, stabilize, and/or postpone progression of the indication. This delay can be of varying lengths of time, depending on the history of the indication and/or individuals being treated. A method that "delays" or alleviates the development of an indication, or delays the onset of the indication, is a method that reduces probability of developing one or more symptoms of the indication in a given time frame and/or reduces extent of the symptoms in a given time frame, when compared to not using the method. Such comparisons are typically based on clinical studies, using a number of subjects sufficient to give a statistically significant result.

Combination Therapies

The disclosure further encompasses pharmaceutical compositions and related methods used as combination therapies for treating subjects who may benefit from RGMc inhibition in vivo. In any of these embodiments, such subjects may receive combination therapies that include a first composition comprising at least one RGMc antagonist, e.g., antibody or antigen-binding fragment thereof, described herein, in conjunction with a second composition comprising at least one additional therapeutic intended to treat the same or overlapping disease or clinical condition. The first and second compositions may both act on the same cellular target, or discrete cellular targets. In some embodiments, the first and second compositions may treat or alleviate the same or overlapping set of symptoms or aspects of a disease or clinical condition. In some embodiments, the first and second compositions may treat or alleviate a separate set of symptoms or aspects of a disease or clinical condition. To give but one example, the first composition may treat a disease or condition (e.g., CKD or cancer), while the second composition may treat inflammation, reduced erythropoiesis, or anemia associated with the same disease, etc. Such combination therapies may be administered in conjunction with each other. The phrase "in conjunction with," in the context of combination therapies, means that therapeutic effects of a first therapy overlaps temporarily and/or spatially with therapeutic effects of a second therapy in the subject receiving the combination therapy. Thus, the combination therapies may be formulated as a single formulation for concurrent administration, or as separate formulations, for sequential administration of the therapies.

In preferred embodiments, combination therapies produce synergistic effects in the treatment of a disease. The term "synergistic" refers to effects that are greater than additive effects (e.g., greater efficacy) of each monotherapy in aggregate.

In some embodiments, combination therapies may achieve faster therapeutic effects than monotherapy.

In some embodiments, combination therapies comprising a pharmaceutical composition described herein produce efficacy that is overall equivalent to that produced by another therapy (such as monotherapy of a second agent) but are associated with fewer unwanted adverse effect or less severe toxicity associated with the second agent, as compared to the monotherapy of the second agent. In some embodiments, such combination therapies allow lower dosage of the second agent but maintain overall efficacy. Such combination therapies may be particularly suitable for patient populations where a long-term treatment is warranted and/or involving pediatric patients.

Accordingly, in one aspect, the invention provides pharmaceutical compositions and methods for use in combination therapies for the reduction of RGMc activity and the treatment or prevention of diseases or conditions associated with RGMc signaling, as described herein. Accordingly, the methods or the pharmaceutical compositions further comprise a second therapy. In some embodiments, the second therapy may be useful in treating or preventing diseases or conditions associated with RGMc signaling. The second therapy may diminish or treat at least one symptom(s) associated with the targeted disease. The first and second therapies may exert their biological effects by similar or unrelated mechanisms of action; or either one or both of the first and second therapies may exert their biological effects by a multiplicity of mechanisms of action. For example, in the context of anemia, an RGMc inhibitor could be administered in combination (e.g., sequentially or concurrently) with a second therapy that increases erythropoiesis (e.g., an EPO therapy, transfusion, etc.). Alternatively, in the context of anemia of chronic disease, an RGMc inhibitor could be administer in combination (e.g., sequentially or concurrently) with a second therapy that treats the underlying disease such as cancer and immune disorders (e.g., chemotherapy, radiation therapy, immunotherapy, etc.).

It should be understood that the pharmaceutical compositions described herein may have the first and second therapies in the same pharmaceutically acceptable carrier or in a different pharmaceutically acceptable carrier for each described embodiment. It further should be understood that the first and second therapies may be administered simultaneously or sequentially within described embodiments.

The one or more RGMc inhibitors (e.g., antibodies or antigen-binding fragments thereof) of the invention may be may be administered to patients who have received or are receiving one or more of additional therapeutic agents. An example of additional therapeutic agents which can be used with an RGMc antibody or the invention include, but are not limited to, erythropoietin stimulating agents (ESAs), Hypoxia-Inducible Factor (HIF) stabilizers, hepcidin antagonists, iron supplements (e.g., oral or intravenous), anti-inflammatories, and/or anti-cancer drugs.

ESAs are medications that stimulate the bone marrow to make red blood cells and are useful in treating various types of anemia in patients. However, even in the presence of increased red blood cell production, without sufficient iron anemia will persist. This is because red blood cells need hemoglobin to transport oxygen and iron is critical in hemoglobin synthesis. Thus, without sufficient iron, the newly produced red blood cells will lack hemoglobin and will be hypochromic (lacking the red hemoglobin pigment) and microcytic (smaller than normal).

Accordingly, in one embodiment, the RGMc antagonists (e.g., RGMc antibodies) described herein may be administered to patients who have received or are receiving an ESA to treat an iron-related disease. Examples of ESAs include, but are not limited to, epoetin alfa, epoetin beta, epoetin delta (e.g., Dynepo®), epoetin omega (e.g., Epomax®), darbepoetin alfa (Aranesp®), Epocept® (Lupin pharma), Nanokine® (Nanogen Pharmaceutical biotechnology), Epofit® (Intas pharma), Epogen® (made by Amgen), Epogin® (Chugai Pharma), Eprex® (made by Janssen-Cilag), Binocrit® (made by Sandoz), PDpoetin® (made by Pooyeshdarou Biopharmaceutical company), Procrit®, Bioyetin® (made by Probiomed), NeoRecormon® (made by Hoffmann-La Roche), Silapo®/Retacrit® (made by Stada/Hospira), EPOTrust® (made by Panacea Biotec Ltd), Erypro Safe™ (made by Biocon Ltd.), Repoitin® (made by Serum Institute of India Limited), Vintor® (made by Emcure Pharmaceuticals), Erykine (made by Intas Biopharmaceutica), Wepox® (made by Wockhardt Biotech), Espogen™ (made by LG life sciences), ReliPoietin™ (made by Reliance Life Sciences), Shanpoietin™ (made by Shantha Biotechnics Ltd), Zyrop® (made by Cadila Healthcare Ltd.), EPIAO® (rHuEPO) (made by Shenyang Sunshine Pharmaceutical Co. LTD.), and China Cinnapoietin® (made by CinnaGen biopharmaceutical Iran).

ESAs are generally efficacious, but there is evidence that a subset of patients does not respond to treatment even at high doses (Solak Y, et al. *Blood Purification.* 2016; 42(2): 160-7). In addition, several studies have shown that use of ESAs may lead to higher rates of cerebrovascular and cardiovascular (CV) events and mortality (Biggar P. et al., *Kidney Research and Clinical Practice* 2017 September; 36(3):209-223). ESAs may also be associated with an increased risk of cancer in some patients, and, in some cases, a poorer response to anticancer treatment. Accordingly, without being bound by a particular theory, use of an RGMc inhibitor in patients who have received or are receiving an ESA, may improve response rates and reduce the required dose of ESA to have an effect, and thereby reducing the occurrence adverse toxicities.

Hypoxia-inducible factor (HIF) prolyl hydroxylase (PH) enzyme inhibitors (a.k.a. HIF-PHIs or HIF stabilizers) are a class of agents for the treatment of anemia. These agents work by stabilizing the HIF complex and stimulating endogenous erythropoietin production. Thus, HIF-PH inhibitors which increase erythropoietin production may be complimented by a drug that increases serum iron levels (e.g., an RGMc inhibitor). Accordingly, in some embodiments, the RGMc inhibitors (e.g., RGMc antibodies) described herein may be administered to patients who have received or are receiving a HIF stabilizer or prolyl hydroxylase (PH) enzyme inhibitor to treat an iron-related disease. Examples of HIF stabilizers or HIF-PH inhibitors include, but are not limited to, Roxadustat (FG-4592), Vadadustat (AKB-6548), Daprodustat (GSK-1278863), Molidustat (BAY 85-3934), Desidustat (ZYAN1), DMOG (N-(2-Methoxy-2-oxoacetyl) glycine methyl ester), IOX2 (N-[[1,2-Dihydro-4-hydroxy-2-oxo-1-(phenylmethyl)-3-quinolinyl]carbonyl]glycine), JNJ-42041935 (1-[6-chloro-5-(trifluoromethoxy)-1H-benzimidazol-2-yl]-1H-pyrazole-4-carboxylic acid), N-Oxalylglycine (2-(Carboxymethylamino)-2-oxoacetic acid), 1,4-dihydrophenonthrolin-4-one-3-Carboxylic acid, and Adaptaquin (7-[(4-Chlorophenyl)[(3-hydroxy-2-pyridinyl)amino]methyl]-8-quinolinol).

In some embodiments, the RGMc-specific inhibitors described herein may be administered to patients who have received or are receiving iron supplements (e.g., oral or intravenous (i.v.) iron). Examples of i.v. iron formulations include, but are not limited to, iron dextran, ferric hydroxide-dextran complex, ferric hydroxid-sucrose complex, ferric gluconate, sodium ferric gluconate, iron sucrose, Fe saccharate, ferumoxytol, ferric carboxymaltose, and iron isomaltoside. Examples of oral iron supplements may include, but are not limited to, ferric pyrophosphate, ferrous gluconate, ferrous sulfate, ferrous fumarate, ferrous carbonate, and carbonyl iron.

Intravenous and oral iron supplemental are also generally efficacious, but studies have demonstrated a variety of toxicities or adverse events associated with iron. Examples of adverse events include cytotoxicity, renal tubular failure, alterations in neutrophil function, promotion of atherosclerosis, promotion of tumor growth, and the generation of free radicals (Cancado and Munoz, *Rev Bras Hematol Hemoter* 2011; 33(6):461-9). Accordingly, without being bound by a particular theory, use of an RGMc-specific inhibitor with i.v. or oral iron, may improve response rates and reduce the required dose iron to have a therapeutic effect, and thereby reducing the occurrence and/or degrees of adverse events/toxicities.

It is recognized that certain drugs which are designed to treat various disease conditions, often induce or exacerbate anemia in the patient being treated (e.g., treatment- or drug-induced anemia, such as chemotherapy-induced anemia and radiation therapy-induced anemia). In some embodiments, the patient is treated with a myelosuppressive drug that may cause side effects that include anemia. Such patient may benefit from the RGMc inhibitor of the present disclosure used in conjunction with the myelosuppressive therapy. Examples of myelosuppressive therapies include but are not limited to: peginterferon alfa-2a, interferon alfa-n3, peginterferon alfa-2b, aldesleukin, gemtuzumab ozogamicin, interferon alfacon-1, rituximab, ibritumomab tiuxetan, tositumomab, alemtuzumab, bevacizumab, L-Phenylalanine, bortezomib, cladribine, carmustine, amsacrine, chlorambucil, raltitrexed, mitomycin, bexarotene, vindesine, floxuridine, tioguanine, vinorelbine, dexrazoxane, sorafenib, streptozocin, gemcitabine, teniposide, epirubicin, chloramphenicol, lenalidomide, altretamine, zidovudine, cisplatin, oxaliplatin, cyclophosphamide, fluorouracil, propylthiouracil, pentostatin, methotrexate, carbamazepine, vinblastine, linezolid, imatinib, clofarabine, pemetrexed, daunorubicin, irinotecan, methimazole, etoposide, dacarbazine, temozolomide, tacrolimus, sirolimus, mechlorethamine, azacitidine, carboplatin, dactinomycin, cytarabine, doxorubicin, hydroxyurea, busulfan, topotecan, mercaptopurine, thalidomide, melphalan, fludarabine, flucytosine, capecitabine, procarbazine, arsenic trioxide, idarubicin, ifosfamide, mitoxantrone, lomustine, paclitaxel, docetaxel, dasatinib, decitabine, nelarabine, everolimus, vorinostat, thiotepa, ixabepilone, nilotinib, belinostat, trabectedin, trastuzumab emtansine, temsirolimus, bosutinib, bendamustine, cabazitaxel, eribulin, ruxolitinib, carfilzomib, tofacitinib, ponatinib, pomalidomide, obinutuzumab, tedizolid phosphate, blinatumomab, ibrutinib, palbociclib, olaparib, dinutuximab, and colchicine.

In some embodiments, the RGMc-specific inhibitors described herein may be administered to patients who have received or are receiving cancer therapy. Such cancer therapy may include, but are not limited to, chemotherapy, radiotherapy/radiation therapy, small molecule drugs, or therapeutic antibodies, e.g., cancer vaccines; engineered immune cell therapies; chemotherapies; radiation therapies; a VEGF agonist; an IGF1 agonist; an FXR agonist; a CCR2 inhibitor; a CCR5 inhibitor; a dual CCR2/CCR5 inhibitor; a lysyl oxidase-like-2 inhibitor; an ASK1 inhibitor; an Acetyl-CoA Carboxylase (ACC) inhibitor; a p38 kinase inhibitor; Pirfenidone; Nintedanib; an M-CSF inhibitor (e.g., M-CSF receptor antagonist and M-CSF neutralizing agents); a MAPK inhibitor (e.g., Erk inhibitor), an immune checkpoint agonist or antagonist (e.g., anti-PD-1 and anti-PD-L1); an IL-11 antagonist; and IL-6 antagonist, and the like. Other examples of the additional therapeutic agents which can be used with the RGMc-specific inhibitors include, but are not limited to, an indoleamine 2,3-dioxygenase (IDO) inhibitor, a tyrosine kinase inhibitor, Ser/Thr kinase inhibitor, a dual-specific kinase inhibitor. In some embodiments, such an agent may be a PI3K inhibitor, a PKC inhibitor, or a JAK inhibitor. In some embodiments, the JAK inhibitor may be a JAK1 inhibitor and/or JAK2 inhibitor, which can be used in the treatment of myeloproliferative disorders, such as primary myelofibrosis.

It is also understood that other cancer treatments, such as radiotherapy, can cause anemia in cancer patients. Accordingly, in one embodiment, the RGMc-specific inhibitors described herein can be used in conjunction with radiotherapy.

In some embodiments, the additional agent to be administered as a combination therapy or used in conjunction with the RGMc inhibitor, is or comprises an inhibitor of a member of the TGFβ superfamily of growth factors or regulators thereof. In some embodiments, such inhibitor is or comprises a TGFβ inhibitor, such as TGFβ neutralizing antibodies. In some embodiment, the TGFβ inhibitor is an antibody that inhibits TGFβ1 and TGFβ 2. In some embodiment, the TGFβ inhibitor is an antibody that inhibits TGFβ1 and TGFβ 3. In some embodiment, the TGFβ inhibitor is an isoform-selective inhibitor of TGFβ1, such as TGFβ1 activation inhibitors. In some embodiment, the TGFβ inhibitor is an isoform-selective inhibitor of TGFβ3, such as TGFβ3 activation inhibitors.

In some embodiments, combination therapy to be used in the treatment of cancer in a subject comprises a cancer immunotherapy (such as a checkpoint inhibitor), a TGFβ1T-selective inhibitor, and the RGMc-selective inhibitor disclosed herein, wherein optionally, the checkpoint inhibitor is a PD-(L)1 antibody, and further optionally, the TGFβ1-selective inhibitor is a TGFβ1-selective activation inhibitor.

In some embodiments, the RGMc-specific inhibitors described herein can be used in conjunction with other compounds, drugs, and/or agents used for the treatment of inflammation-associated diseases or chronic kidney disease. Such compounds, drugs, and/or agents can include, but are not limited to, non-steroidal anti-inflammatory drugs (NSAIDs), angiotensin-converting enzyme (ACE) inhibitors, angiotensin II receptor blockers (ARBs), diuretics, β-blockers, calcium channel blockers, central sympatholytic agents, bicarbonate supplements, insulin, vitamin D supplements, uric acid reducers (e.g., allopurinol), HMG-CaA reductase inhibitors (statins), pirfenidone, TGFβ pathway inhibitors, anti-inflammatories (including nonsteroidal anti-inflammatory drugs), antioxidant inflammation modulators (e.g., bardoxolone methyl), endothelin-1 antagonists (e.g., avosentan and atrasentan), advanced glycan end product inhibitors, aspirin, metformin, aminoguanidine, calcitriol, erythropoietins, androgens, phosphate binders, vitamin B12, and vitamin B6 and derivatives thereof (e.g., pyridoxamine).

In some embodiments, the RGMc-specific inhibitors described herein can be used in conjunction with a granulocyte-colony stimulating factor (G-CSF) or derivative thereof, e.g., Neupogen®, Granix®, or Zarxio®. G-CSFs are glycoproteins used to stimulate the production of blood cells (e.g., white blood cells or hematopoietic stem cells) and promote their ability to function. Thus, G-CSFs are useful for reducing the risk of a patient developing infections, anemia, and bleeding problems after receiving a myelosuppressive treatment (e.g., chemotherapy). However, there are side effects to the use of G-CSFs, which include: thrombocytopenia, nausea, fever, bone pain, elevated lactate dehydrogenase, elevated alkaline phosphatase, petechial, back pain, epistaxis (nosebleeds), cough, and/or dyspnea (shortness of breath). Accordingly, it is contemplated that an RGMc-specific inhibitors as described herein may complement the pharmacological effects of G-CSFs (e.g., reduce anemia and promote red blood cell production) and/or to reduce the effective dosage of G-CSF so as to reduce side effects and increase tolerability. Accordingly, in one embodiment, the RGMc-specific inhibitors as described herein may be administered to patients who have received or are receiving a G-CSF therapy. In another embodiment, the RGMc-specific inhibitors as described herein reduce the effective dosage of G-CSF necessary to achieve a favorable pharmacological effect, e.g., promote blood cell production and/or reduce anemia. In another embodiment, the RGMc-specific inhibitors as described herein complement the effects of G-CSFs, e.g., further increase red blood cell production and/or reduce anemia.

Combination therapies contemplated herein may advantageously utilize lower dosages of the administered therapeutic agents, thus avoiding possible toxicities or complications associated with the various monotherapies. In some embodiments, use of an RGMc-specific inhibitor described herein may render those who are poorly responsive or not responsive to a therapy (e.g., standard of care) more responsive. In some embodiments, use of an RGMc-specific inhibitor described herein may allow reduced dosage of the therapy (e.g., standard of care) which still produces equivalent clinical efficacy in patients but fewer or lesser degrees of drug-related toxicities or adverse events.

Inhibition of RGMc Activity

Methods of the present disclosure include methods of inhibiting RGMc activity in one or more biological systems. Such methods may include contacting one or more biological systems with an antibody and/or composition of the disclosure. Inhibitors (e.g., antibodies) and/or compositions according to such methods may include, but are not limited to biomolecules, including, but not limited to recombinant proteins, protein complexes and/or antibodies, or antigen fragments thereof, as described herein.

The inhibitors, e.g., antibodies and antigen-binding fragments thereof, described herein that selectively bind an RGMc can be used in a wide variety of applications in which modulation of RGMc activity is desired. In one embodiment, the invention provides a method of inhibiting RGMc activation by exposing an RGMc peptide or protein to an inhibitor, e.g., antibody, or antigen-binding fragment thereof, which selectively binds RGMc. The foregoing method can be performed in vitro, e.g., to inhibit RGMc activity in cultured cells. The foregoing method can also be performed in vivo, e.g., in a subject in need of RGMc inhibition, or in an animal model in which the effect of RGMc inhibition is to be assessed.

Any inhibitor, e.g., antibody, or antigen-binding fragment thereof, described herein which selectively binds RGMc, and any pharmaceutical composition comprising such inhibitor or antibody, is suitable for use in the methods of the invention.

Accordingly, in one aspect of the invention, a method of inhibiting RGMc activity by exposing a RGMc to an inhibitor, e.g., an antibody, or antigen-binding fragment there, which selectively binds to RGMc, is provided. In some embodiments, the inhibitors (e.g., antibodies or antigen-binding fragments thereof) compete with BMP for binding to RGMc. In some embodiments, the BMP is BMP2 and/or BMP6. In some embodiments, the BMP is BMP6.

In another embodiment, the inhibitors (e.g., antibodies or antigen-binding fragments thereof) inhibit neogenin binding to RGMc. In some embodiments, the inhibitors (e.g., antibodies or antigen-binding fragments thereof) compete with neogenin for binding to RGMc.

In some embodiments, the inhibitors (e.g., antibodies or antigen-binding fragments thereof) do not inhibit neogenin binding to RGMc. In some embodiments, the inhibitors (e.g., antibodies or antigen-binding fragments thereof) do not compete with neogenin for binding to RGMc.

In another embodiment, the inhibitors (e.g., antibodies or antigen-binding fragments thereof) inhibit the binding of RGMc to other binding partners or proteins that complex with RGMc. For example, other binding partners that complex with RGMc, BMP, and/or neogenin include HFE, TFR2, ALK2, ALK3, BMPR2, ACVR2A and TMPRSS6.

In another embodiment, the antibodies, or antigen-binding fragments thereof, that inhibit RGMc activity can also modulate other biological processes (e.g., downstream effects). For example, the antibodies, or antigen-binding fragments thereof, that inhibit RGMc activity reduce hepcidin expression in a subject. In some embodiments, the antibodies, or antigen-binding fragments thereof, that inhibit RGMc activity increase ferroportin expression in a subject. In some embodiments, the antibodies, or antigen-binding fragments thereof, that inhibit RGMc activity increase transferrin saturation in a subject. In some embodiments, the antibodies, or antigen-binding fragments thereof, that inhibit RGMc activity increase erythropoiesis in a subject. In some embodiments, the antibodies, or antigen-binding fragments thereof, that inhibit RGMc activity decrease unsaturated iron binding capacity (UIBC) in a subject. In some embodiments, the antibodies, or antigen-binding fragments thereof, that inhibit RGMc activity decrease total iron binding capacity (TIBC) in a subject. In some embodiments, the antibodies, or antigen-binding fragments thereof, that inhibit RGMc activity increase serum ferritin levels in a subject.

In some embodiments, the methods described herein can be performed in a subject. The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having an RGMc-related indication, such as those noted above (e.g., anemia).

Accordingly, in one embodiment, a method for increasing serum iron levels in a subject is provided, the method comprising administering to the subject a pharmaceutical composition of the invention (e.g., a RGMc-specific inhibitor as disclosed herein) in an amount effective to downregulate hepcidin in the subject. In some embodiments, a method for downregulating hepcidin in a subject is provided, the method comprising administering to the subject a pharmaceutical composition of the invention (e.g., a RGMc-specific inhibitor as disclosed herein) in an amount effective to downregulate hepcidin in the subject. In some embodiments, the pharmaceutical composition reduces liver hepcidin mRNA levels. In some embodiments, the pharmaceutical composition reduces liver hepcidin protein levels, serum (circulating) hepcidin protein levels, or both.

In one embodiment, a method for increasing serum iron levels in a subject is provided, the method comprising administering to the subject a pharmaceutical composition of the invention (e.g., an RGMc-specific inhibitor as disclosed herein) in an amount effective to increase ferroportin expression in the subject, as compared to baseline. In some embodiments, a method for increases ferroportin expression in a subject is provided, the method comprising administering to the subject a pharmaceutical composition of the invention (e.g., an RGMc-specific inhibitor as disclosed herein) in an amount effective to increases ferroportin expression in the subject. In some embodiments, the pharmaceutical composition increases enterocyte (intestinal) ferroportin protein levels. In some embodiments, the pharmaceutical composition increases hepatocyte (liver) ferroportin protein levels. In some embodiments, the pharmaceutical composition increases macrophage ferroportin protein levels. In some embodiments, the pharmaceutical composition increases adipocyte ferroportin protein levels.

In some embodiments, a method for increasing transferrin saturation in a subject is provided, the method comprising administering to the subject a pharmaceutical composition of the invention (e.g., a RGMc-specific inhibitor as disclosed herein) in an amount effective to increase transferrin saturation (TSAT) in the subject. In some embodiments, the method increases transferrin saturation by 1%, ≥2%, ≥3%, ≥4%, ≥5%, ≥6%, ≥7%, ≥8%, ≥9%, or ≥10%, as compared to baseline. In some embodiments, the method increases transferrin saturation by ≥1%. In some embodiments, the method increases transferrin saturation by ≥2%, as compared to baseline. In some embodiments, the method increases transferrin saturation by ≥3%, as compared to baseline. In some embodiments, the method increases transferrin saturation by ≥4%, as compared to baseline. In some embodiments, the method increases transferrin saturation by ≥5%, as compared to baseline. In some embodiments, the method increases transferrin saturation by ≥6%, as compared to baseline. In some embodiments, the method increases transferrin saturation by ≥7%, as compared to baseline. In some embodiments, the method increases transferrin saturation by ≥8%, as compared to baseline. In some embodiments, the method increases transferrin saturation by ≥9%, as compared to baseline. In some embodiments, the method increases transferrin saturation by 10%, as compared to baseline.

In some embodiments, the method increases transferrin saturation in a subject to a level of ≥15%, ≥16%, ≥17%, ≥18%, ≥19%, ≥20%, ≥21%, ≥22%, ≥23%, ≥24%, or ≥25%. In some embodiments, the method increases transferrin saturation in a subject to a level of ≥15%. In some embodiments, the method increases transferrin saturation in a subject to a level of ≥16%. In some embodiments, the method increases transferrin saturation in a subject to a level of ≥17%. In some embodiments, the method increases transferrin saturation in a subject to a level of ≥18%. In some embodiments, the method increases transferrin saturation in a subject to a level of ≥19%. In some embodiments, the method increases transferrin saturation in a subject to a level of ≥20%. In some embodiments, the method increases transferrin saturation in a subject to a level of ≥21%. In some embodiments, the method increases transferrin saturation in a subject to a level of ≥22%. In some embodiments, the method increases transferrin saturation in a subject to a level of ≥23%. In some embodiments, the method increases transferrin saturation in a subject to a level of ≥24%. In some embodiments, the method increases transferrin saturation in a subject to a level of ≥25%.

In some embodiments, a method for increasing erythropoiesis in a subject is provided, the method comprising administering to the subject a pharmaceutical composition of the invention (e.g., a RGMc-specific inhibitor as disclosed herein) in an amount effective to increase erythropoiesis in the subject.

In some embodiments, a method for increasing hemoglobin (Hb) levels in a subject is provided, the method comprising administering to the subject a pharmaceutical composition of the invention (e.g., an RGMc-specific inhibitor as disclosed herein) in an amount effective to increase hemoglobin levels. In some embodiments, the method increases Hb levels by ≥1, ≥2, or ≥3 g/dl, as compared to baseline. In some embodiments, the method increases Hb levels by ≥1 g/dl, as compared to baseline. In some embodiments, the method increases Hb levels by ≥2 g/dl, as compared to baseline. In some embodiments, the method increases Hb levels by ≥3 g/dl, as compared to baseline. In some embodiments, the method increases Hb in a subject to a level of ≥10 g/dl. In some embodiments, the method increases Hb to a level of ≥11 g/dl. In some embodiments, the method increases Hb to a level of ≥12 g/dl. In some embodiments, the method increases Hb to a level of ≥13 g/dl.

In some embodiments, a method for decreasing unsaturated iron binding capacity (UIBC) in a subject is provided, the method comprising administering to the subject a pharmaceutical composition of the invention (e.g., a RGMc-specific inhibitor as disclosed herein) in an amount effective to decrease unsaturated iron binding capacity in the subject. A typical range for UIBC in a subject is 120-470 ug/dL (21-84 umol/L), although levels may vary among populations. Accordingly, in some embodiments, the subject has a UIBC of ≥400, ≥450, ≥500, ≥550, ≥600, ≥650, ≥700, ≥750, or ≥800 ug/dL. In other embodiments, the effective amount of RGMc-specific inhibitor decreases UIBC in the subject by ≥50, ≥100, ≥150, ≥200, ≥250, ≥300, ≥350, or ≥450 ug/dL.

In some embodiments, a method for decreasing total iron binding capacity (TIBC) in a subject is provided, the method comprising administering to the subject the pharmaceutical composition of the invention (e.g., a RGMc-specific inhibitor as disclosed herein) in an amount effective to decrease total iron binding capacity in the subject. A typical range for TIBC is 255-450 ug/dL, although levels will vary among populations. Accordingly, in some embodiments, the subject has a TIBC of ≥400, ≥450, ≥500, ≥550, ≥600, ≥650, ≥700, ≥750, or ≥800 ug/dL. In other embodiments, the effective amount of RGMc-specific inhibitor decreases TIBC in the subject by ≥50, ≥100, ≥150, ≥200, ≥250, ≥300, ≥350, or ≥450 ug/dL.

In some embodiments, a method for increasing serum ferritin levels in a subject is provided, the method comprising administering to the subject the pharmaceutical composition of the invention (e.g., RGMc-specific inhibitor as disclosed herein) in an amount effective to increase serum ferritin levels in the subject. In some embodiments, the method increases serum ferritin levels in a subject by ≥5, ≥10, ≥15, ≥20, ≥30, ≥40, ≥50, ≥60, ≥70, ≥80, ≥90, or ≥100 ng/ml as compared to baseline. In some embodiments, the method increases serum ferritin levels in a subject by ≥5 ng/ml as compared to baseline. In some embodiments, the method increases serum ferritin levels in a subject by ≥10 ng/ml as compared to baseline. In some embodiments, the method increases serum ferritin levels in a subject by ≥15 ng/ml as compared to baseline. In some embodiments, the method increases serum ferritin levels in a subject by ≥20 ng/ml as compared to baseline. In some embodiments, the method increases serum ferritin levels in a subject by ≥30 ng/ml as compared to baseline. In some embodiments, the method increases serum ferritin levels in a subject by ≥40 ng/ml as compared to baseline. In some embodiments, the method increases serum ferritin levels in a subject by ≥50 ng/ml as compared to baseline. In some embodiments, the method increases serum ferritin levels in a subject by ≥60 ng/ml as compared to baseline. In some embodiments, the method increases serum ferritin levels in a subject by ≥70 ng/ml as compared to baseline. In some embodiments, the method increases serum ferritin levels in a subject by ≥80 ng/ml as compared to baseline. In some embodiments, the method increases serum ferritin levels in a subject by ≥90 ng/ml as compared to baseline. In some embodiments, the method increases serum ferritin levels in a subject by ≥100 ng/ml as compared to baseline.

In some embodiments, the method increases serum ferritin in a subject to a level of ≥30 ng/ml. In some embodiments, the method increases serum ferritin in a subject to a level of ≥40 ng/ml. In some embodiments, the method increases serum ferritin in a subject to a level of ≥50 ng/ml. In some embodiments, the method increases serum ferritin in a subject to a level of ≥60 ng/ml. In some embodiments, the method increases serum ferritin in a subject to a level of ≥70 ng/ml. In some embodiments, the method increases serum ferritin in a subject to a level of ≥80 ng/ml. In some embodiments, the method increases serum ferritin in a subject to a level of ≥90 ng/ml. In some embodiments, the method increases serum ferritin in a subject to a level of ≥100 ng/ml.

In some embodiments, a method for treating a disease associated with RGMc in a subject is provided, the method comprising administering to the subject the pharmaceutical composition of the invention (e.g., a RGMc-specific inhibitor as disclosed herein) in an amount effective to treat the disease. In some embodiments, the disease associated with RGMc is anemia. In some embodiments, the anemia is iron-refractory iron-deficiency anemia (IRIDA). In some embodiments, the anemia is anemia of chronic disease (ACD). In some embodiments, the ACD is a cancer-related anemia. In another embodiments, the ACD is anemia associated with chronic kidney disease (CKD). In some embodiments, the anemia is a chemotherapy-induced anemia.

Kits for Use in Alleviating Diseases/Disorders Associated with a RGMc-Related Indication The present disclosure also provides kits for use in alleviating diseases/disorders associated with a RGMc-related indication (e.g., anemia). Such kits can include one or more containers comprising an inhibitor, e.g., antibody, or antigen-binding fragment thereof, that selectively binds RGMc.

In some embodiments, the kit can comprise instructions for use in accordance with any of the methods described herein. The included instructions can comprise a description of administration of the inhibitor, e.g., antibody, or antigen-binding fragment thereof, that selectively binds RGMc to treat, delay the onset, or alleviate a target disease as those described herein. The kit may further comprise a description of selecting an individual suitable for treatment based on identifying whether that individual has the target disease. In still other embodiments, the instructions comprise a description of administering an antibody, or antigen-binding fragment thereof, to an individual at risk of the target disease.

The instructions relating to the use of inhibitors, e.g., antibodies, or antigen-binding fragments thereof, that selectively bind RGMc generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert (e.g., a paper sheet included in the kit), but machine-readable instructions (e.g., instructions carried on a magnetic or optical storage disk) are also acceptable. The label or package insert can indicate that the composition is used for treating, delaying the onset and/or alleviating a disease or disorder associated with a TGFβ-related indication. Instructions may be provided for practicing any of the methods described herein.

The kits of this disclosure can be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an inhibitor, e.g., antibody, or antigen-binding fragment thereof, that selectively binds RGMc, as described herein.

Kits may optionally provide additional components such as buffers and interpretive information. Normally, the kit comprises a container and a label or package insert(s) on or associated with the container. In some embodiments, the disclosure provides articles of manufacture comprising contents of the kits described above.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present disclosure.

LIST OF PREFERRED EMBODIMENTS

1. An isolated antibody that specifically binds human Repulsive Guidance Molecule C (RGMc), wherein:
   a) the antibody is a full-length antibody or antigen-binding fragment thereof;
   b) the antibody does not bind human Repulsive Guidance Molecule A (RGMa) and human Repulsive Guidance Molecule B (RGMb); and
   c) the antibody inhibits or reduces RGMc interaction with BMP6.
3. The antibody of embodiment 1 or embodiment 2, wherein the antibody binds to a discontinuous epitope comprising at least a fragment of each a first and second binding region within human RGMc, wherein the first binding region comprises the amino acid sequence as set forth in SEQ ID NO: 46, wherein optionally the second binding region comprises the amino acid sequence as set forth in SEQ ID NO: 47.

4. An isolated antibody that binds an epitope within human RGMc, wherein:
   a) the antibody is a full-length antibody or antigen-binding fragment thereof; and
   b) the antibody binds an epitope comprising at least one amino acid residue of YVSSTLSL (SEQ ID NO: 46) and/or at least one amino acid residue of FHSAVHGIEDL (SEQ ID NO: 47).

5. The antibody of embodiment 4, wherein the epitope comprises at least one amino acid residue of YVSSTLSL (SEQ ID NO: 46) and at least one amino acid residue of FHSAVHGIEDL (SEQ ID NO: 47).

6. The antibody of embodiment 4 or 5, wherein the antibody does not bind human RGMa and human RGMb.

7. The antibody of any one of embodiments 4-76, wherein the antibody inhibits or reduces RGMc interaction with BMP6.

8. The antibody of any one of embodiments 4-7, wherein the antibody does not inhibit or reduce RGMc interaction with neogenin.

9. An isolated antibody that specifically binds human RGMc, wherein the antibody is a full-length antibody or antigen-binding fragment thereof, and wherein the antibody comprises at least three of the following six CDRs:
   a) CDR-H1: SEQ ID NO: 14, with the proviso that:
      i. the serine residue at position 4 of SEQ ID NO: 14 may be substituted with an arginine;
      ii. the alanine residue at position 7 of SEQ ID NO: 14 may be substituted with a serine; and/or
      iii. the serine residue at position 9 of SEQ ID NO: 14 may be substituted with a glutamine;
   b) CDR-H2: SEQ ID NO: 15, with the proviso that:
      i. the threonine residue at position 8 of SEQ ID NO: 15 may be substituted with a valine; and/or
      ii. the asparagine residue at position 10 of SEQ ID NO: 15 may be substituted with a serine;
   c) CDR-H3: SEQ ID NO: 16, with the proviso that:
      i. the isoleucine residue at position 5 of SEQ ID NO: 16 may be substituted with a tyrosine; and/or
      ii. the alanine residue at position 6 of SEQ ID NO: 16 may be substituted with a valine;
   d) CDR-L1: SEQ ID NO: 17;
   e) CDR-L2: SEQ ID NO: 18; and,
   f) CDR-L3: SEQ ID NO: 19.

10. The antibody of any one of the preceding embodiments, wherein the antibody comprises heavy chain CDR1 (H-CDR1), heavy chain CDR2 (H-CDR2), and heavy chain CDR3 (H-CDR3) sequences as set forth in SEQ ID NOs: 30, 31, and 32, respectively, and light chain CDR1 (L-CDR1), light chain CDR2 (L-CDR2), and light chain CDR3 (L-CDR3) sequences as set forth in SEQ ID Nos: 33, 34, and 35, respectively; wherein optionally:
   the R residue at position 4 of the H-CDR1 is replaced with a K or S; the S residue at position 5 of the H-CDR1 is replaced with a T; the S residue at position 7 of the H-CDR1 is replaced with an A; and/or, the S residue at position 9 of the H-CDR1 is replaced with a Q;
   wherein further optionally:
   the V residue at position 8 of the H-CDR2 is replaced with a H or T; and/or the N residue at position 10 of the H-CDR2 is replaced with a S, T or E.

11. The antibody of any one of the preceding embodiments, wherein the antibody comprises:
   a) a heavy chain variable region having an amino acid sequence that is at least 90% identical to SEQ ID NO: SEQ ID NO: 36; and/or
   b) a variable light chain variable region having an amino acid sequence that is at least 90% identical to SEQ ID NO: 37.

12. The antibody of any one of the preceding embodiments, wherein the antibody comprises:
   a) a heavy chain variable region sequence as set forth in SEQ ID NO: 36; and
   b) a light chain variable region sequences as set forth in SEQ ID NO: 37.

13. The antibody of any one of the preceding embodiments, wherein the antibody comprises heavy chain CDR1, CDR2, and CDR3 sequences as set forth in SEQ ID NOs: 38, 39, and 40, respectively, and light chain CDR1, CDR2, and CDR3 sequences as set forth in SEQ ID NOs: 41, 42, and 43, respectively.

14. The antibody of any one of the preceding embodiments, wherein the antibody comprises:
   c) a heavy chain variable region having an amino acid sequence that is at least 90% identical to SEQ ID NO: SEQ ID NO: 44; and/or
   d) a variable light chain variable region having an amino acid sequence that is at least 90% identical to SEQ ID NO: 45.

15. The antibody of any one of the preceding embodiments, wherein the antibody comprises:
   a) a heavy chain variable region sequence as set forth in SEQ ID NO: 44; and
   b) a light chain variable region sequences as set forth in SEQ ID NO: 45.

16. The antibody of any one of the preceding embodiments, wherein the antibody is a fully human or humanized antibody.

17. The antibody of any one of the preceding embodiments, which is a human IgG1, IgG2, or IgG4 antibody.

18. The antibody of any one of the preceding claims, which is a human IgG4 antibody, wherein optionally the human IgG4 antibody comprises a backbone substitution of Ser to Pro that produces an IgG1-like hinge.

19. The antibody of any one of the preceding embodiments, wherein the antibody binds to a cell expressing membrane-bound human RGMc.

20. The antibody of any one of the preceding embodiments, wherein the antibody binds to RGMc with a $K_D$ value of less than $0.1 \times 10^{-9}$ (0.1 nM).

21. The antibody of any one of the preceding embodiments, wherein the antibody modulates interaction of RGMc with one or more of the following interacting proteins; HFE, TFR2, ALK2, ALK3, BMPR2, ACVR2A and TMPRSS6.

22. An isolated antibody that specifically binds human RGMc, wherein the antibody competes for binding to human RGMc with, and/or binds to the same epitope as, an antibody of any one of embodiments 4-21.

23. A pharmaceutical composition comprising the antibody of any one of the preceding embodiments and a pharmaceutically acceptable carrier.

24. The composition of embodiment 23 for use in a method for the treatment of a disease associated with RGMc in a human subject, wherein the treatment comprises administration of the composition to the subject in an amount effective to treat the condition.

25. The composition for use according to embodiment 24, wherein the disease associated with RGMc is anemia.

26. The composition for use according to embodiment 25, wherein the anemia is iron-refractory iron-deficiency anemia (IRIDA) or anemia of chronic disease (ACD).
27. The composition for use according to embodiment 26, wherein the ACD is a cancer-related anemia.
28. The composition for use according to embodiment 25, wherein the anemia is a chemotherapy-induced anemia.
29. The composition for use according to embodiment 26, wherein the ACD is anemia associated with chronic kidney disease (CKD).
30. The composition for use according to any one of embodiment 24-29, wherein the composition is administered in combination with an additional therapeutic agent.
31. The composition for use according to embodiment 30, wherein the additional therapeutic agent is an Erythropoietin Stimulating Agent (ESA), HIF stabilizer, iron supplement or transfusion.
32. The composition for use according to embodiment 31, wherein the method reduces toxicities associated with ESAs, HIF stabilizers, iron supplement or transfusion.
33. The composition for use according to embodiment 32, wherein the toxicities include iron overload, a risk of cancer and/or risk of cardiovascular events (e.g., major cardiac adverse events such as stroke).
34. The composition for use according to any one of embodiments 24-33, wherein the subject is:
    a) on the iron therapy but benefits from reduced dosing of the iron therapy;
    b) has received the iron therapy but discontinued due to toxicities;
    c) has received the iron therapy and benefits from reduced dosing of the iron therapy;
    d) is at risk of cancer; and/or
    e) has been diagnosed with cancer.
35. A method for treating a disease associated with RGMc in a subject, the method comprising administering to the subject the pharmaceutical composition of embodiment 23 in an amount effective to treat the disease.
36. A method for increasing serum iron levels in a subject, the method comprising administering to the subject the pharmaceutical composition of embodiment 23 in an amount effective to increase serum iron levels in the subject.
37. A method for downregulating hepcidin in a subject, the method comprising administering to the subject the pharmaceutical composition of embodiment 23 in an amount effective to downregulate hepcidin in the subject.
38. The method of embodiment 37, wherein the pharmaceutical composition reduces liver hepcidin mRNA levels.
39. The method of embodiment 37, wherein the pharmaceutical composition reduces liver hepcidin protein levels, serum (circulating) hepcidin protein levels, or both.
40. A method for increasing transferrin saturation in a subject, the method comprising administering to the subject the pharmaceutical composition of embodiment 23 in an amount effective to increase transferrin saturation in the subject.
41. A method for increasing erythropoiesis in a subject, the method comprising administering to the subject the pharmaceutical composition of embodiment 23 or 24 in an amount effective to increase erythropoiesis in the subject.
42. A method for decreasing unsaturated iron binding capacity (UIBC) in a subject, the method comprising administering to the subject the pharmaceutical composition of embodiment 23 in an amount effective to decrease unsaturated iron binding capacity in the subject.
43. A method for decreasing total iron binding capacity (TIBC) in a subject, the method comprising administering to the subject the pharmaceutical composition of embodiment 23 in an amount effective to decrease total iron binding capacity in the subject.
44. A method for increasing serum ferritin levels in a subject, the method comprising administering to the subject the pharmaceutical composition of embodiment 23 in an amount effective to increase serum ferritin levels in the subject.
45. The method of embodiment 44, wherein the amount is an amount effective to achieve the serum ferritin levels of ≥20 nanograms per milliliter of blood.
46. The pharmaceutical composition for use according to any one of embodiments 24-34 or the method according to any one of embodiments 35-45, wherein the subject has received an erythropoietin (e.g., EPO) therapy, HIF stabilizer therapy, IV iron supplementation, or combination thereof.
47. The pharmaceutical composition for use according to any one of embodiments 24-34 or the method according to any one of embodiments 35-45, wherein the subject has manifested or is at risk of an adverse event associated with the EPO therapy or the IV iron supplementation.
48. A method for making a pharmaceutical composition comprising an RGMc-selective inhibitor (e.g., neutralizing antibody), the method comprising the steps of
    i) identifying antibodies or antigen-binding fragments for the ability to selectively bind RGMc over RGMa and RGMb;
    ii) identifying the antibodies or antigen-binding fragment based on step (i) for the ability to inhibit/ neutralize RGMc activity in vivo;
    iii) selecting an inhibitory/neutralizing antibody based on steps (i) and (ii) for formulation into a pharmaceutical composition.
49. The method of embodiment 48, wherein step (i) comprises a positive selection and optionally further comprises a negative selection.
50. The method of embodiment 48 or 49, wherein the epitope excludes a Neogenin-binding site.
51. The method of embodiment 48 or embodiment 49, wherein the antibody preferentially binds membrane-bound RGMc over soluble RGMc.
52. The method of embodiment 48 or embodiment 49, wherein the antibody induces internalization of an antibody-antigen complex.
53. The method of any one of embodiments 48-52, wherein the identification step (i) comprises screening a library.
54. The method of embodiment 53, wherein the library is a phage library or a yeast library.
55. The method of any one of embodiments 48-54, wherein the identification step (ii) comprises measuring an iron parameter selected from the group consisting of: serum iron, total iron binding capacity (TIBC), unsaturated iron binding capacity (UIBC), and transferrin saturation.

56. The method of any one of embodiments 48-55, wherein step (ii) comprises measuring hepcidin expression.
57. The method of embodiment 56, wherein the hepcidin expression is liver hepcidin levels and/or serum hepcidin levels.
58. The method of any one of embodiments 48-57, wherein step (ii) comprises identifying neutralizing antibodies or antigen-binding fragments capable of elevating serum iron levels and/or suppressing hepcidin expression in vivo.
59. The method of any one of embodiments 48-58, wherein the pharmaceutical composition is formulated for an intravenous or subcutaneous administration.
60. The method of any one of embodiments 48-59, wherein step (i) comprises confirming selectively for RGMc over RGMa and RGMb.
61. An RGMc-selective inhibitor for use in a method for treating iron disorder in a subject, wherein the RGMc-specific inhibitor does not inhibit RGMa and RGMb, and wherein the iron disorder causes anemia in the subject.
62. An RGMc-selective inhibitor for use in a method for reducing toxicities associated with an iron therapy, wherein the method comprises administrating an effective amount of the RGMc-selective inhibitor to the subject.
63. The RGMc-selective inhibitor for use according to embodiment 62, wherein the iron therapy is an EPO therapy, iron supplement or transfusion.
64. The RGMc-selective inhibitor for use according to embodiment 62 or 63, wherein the toxicities include iron overload or a risk of cancer.
65. The RGMc-selective inhibitor for use according to any one of embodiments 62-64, wherein the subject is a) on the iron therapy but benefits from reduced dosing of the iron therapy; b) has received the iron therapy but discontinued due to toxicities; c) has received the iron therapy and benefits from reduced dosing of the iron therapy; d) is at risk of cancer; e) has been diagnosed with cancer.
66. The RGMc-selective inhibitor for use according to any one of embodiments 61-65, wherein the RGMc-selective inhibitor is an RGMc-selective antibody, wherein optionally the RGMc-selective antibody is a neutralizing antibody.
67. The RGMc-selective inhibitor for use according to embodiment 66, wherein the RGMc-selective antibody binds an extracellular portion of RGMc or a complex comprising the same.
68. The RGMc-selective inhibitor for use according to embodiment 67, wherein the RGMc-selective antibody binds an extracellular portion of RGMc or a complex comprising the same present on cell-surface.
69. An RGMc-selective inhibitor for use in the treatment of functional iron deficiency in a subject, wherein the subject has received an ESA and/or HIF stabilizer.
70. An RGMc-selective inhibitor and an erythropoietin therapy (e.g., ESAs, HIF stabilizers) for use in the treatment of functional iron deficiency in a subject.
71. The RGMc-selective inhibitor and the erythropoietin therapy (e.g., ESAs, HIF stabilizers) for use according to embodiment 70, wherein the treatment achieves faster relief or onset of therapeutic benefit as compared to the erythropoietin therapy alone, wherein optionally the therapeutic benefit comprises increased serum iron, increased transferrin saturation, increased hemoglobin, or any combination thereof.
72. The RGMc-selective inhibitor for use according to embodiment 70, wherein the RGMc-selective inhibitor sensitizes the erythropoietin therapy.
73. An RGMc-selective inhibitor for use in reducing the dosage or frequency of an iron therapy selected from oral or IV iron supplements, transfusion, ESAs and HIF stabilizers, wherein the RGMc-selective inhibitor achieves therapeutic benefits when administered in conjunction with the iron therapy.
74. An RGMc-selective inhibitor for use in treating anemia in a subject who has cancer.
75. The RGMc-selective inhibitor for use according to embodiment 74, wherein the subject is a candidate or receiving chemotherapy.
76. The RGMc-selective inhibitor for use according to embodiment 74, wherein the subject has received chemotherapy.
77. The RGMc-selective inhibitor for use according to embodiment 74, wherein the subject is not a candidate for receiving an ESA therapy or HIF stabilizer therapy.
78. An RGMc-selective inhibitor for use in the treatment of functional iron deficiency in a subject who is hyporesponsive to an erythropoietin therapy or iron supplement.
79. An RGMc-selective inhibitor for use in the treatment of functional iron deficiency in a subject who is intolerant to an erythropoietin therapy or iron supplement.

The present invention is further illustrated by the following examples, which are not intended to be limiting in any way. The entire contents of all references, patents and published patent applications cited throughout this application, as well as the Figures, are hereby incorporated herein by reference.

EXAMPLES

RGMc is a liver-expressed obligate co-receptor for certain BMPs, such as BMP6, that enhance hepcidin expression and, consequently, inhibit iron transport. On the other hand, other RGM family members such as RGMa and RGMb are more widely expressed, e.g., in the nervous system, brain, skin, heart, liver, lung, kidney, testis, and gut. Additionally, BMP6 has wide expression through the body, e.g., brain, bone, liver, lung, kidney, pancreas testis, and gut. Accordingly, by targeting RGMc, whose expression is more restrictive than that of RGMa, RGMb, and BMP6, more tissue-specific effects may be achieved while reducing off-target effects. This approach presents the potential to address both iron-restricted anemias and iron overload conditions without broadly inhibiting RGM and BMP6 functions throughout the body, which could lead to non-desirable toxicities.

Accordingly, the present invention includes the recognition that selective targeting of RGMc provides an advantageous approach to achieve both efficacy and safety (reduced toxicities) as compared to conventional approaches, such as direct BMP6 antagonists and non-selective inhibitors of RGMa/RGMb/RGMc.

Example 1: Identification of RGMc-Specific Antibodies

Antibodies that are selective for RGMc were generated using known techniques as describe herein. RGMc specificity over RGMa and RGMb was verified using an in vitro binding assay (i.e., Octet®). The binding affinity of test antibodies to their target was performed by taking each antibody at 7.5 ug/ml (or 50 nM) in 1× Kinetics Buffer, and loading it onto an Anti-hIgG Fc Capture (AHC) biosensor from Pall ForteBio®. After loading, a baseline reading was obtained by placing the tips into 1× Kinetics Buffer before calculating the on rate, or association, of the antibodies by presenting them to histidine tagged hRGMc, hRGMa, or hRGMb, at varying concentrations (900 nM, 300 nM, 100 nM, and 33 nM). After reaching binding saturation, a dissociation step was performed to calculate the off rate by moving the tips back into 1× Kinetics Buffer. The rate of binding and dissociation can then be used to calculate the $K_D$, or binding affinity of each antibody to the main target (RGMc) while ensuring no cross binding to RGM family members (RGMa and RGMb).

Figure 2:
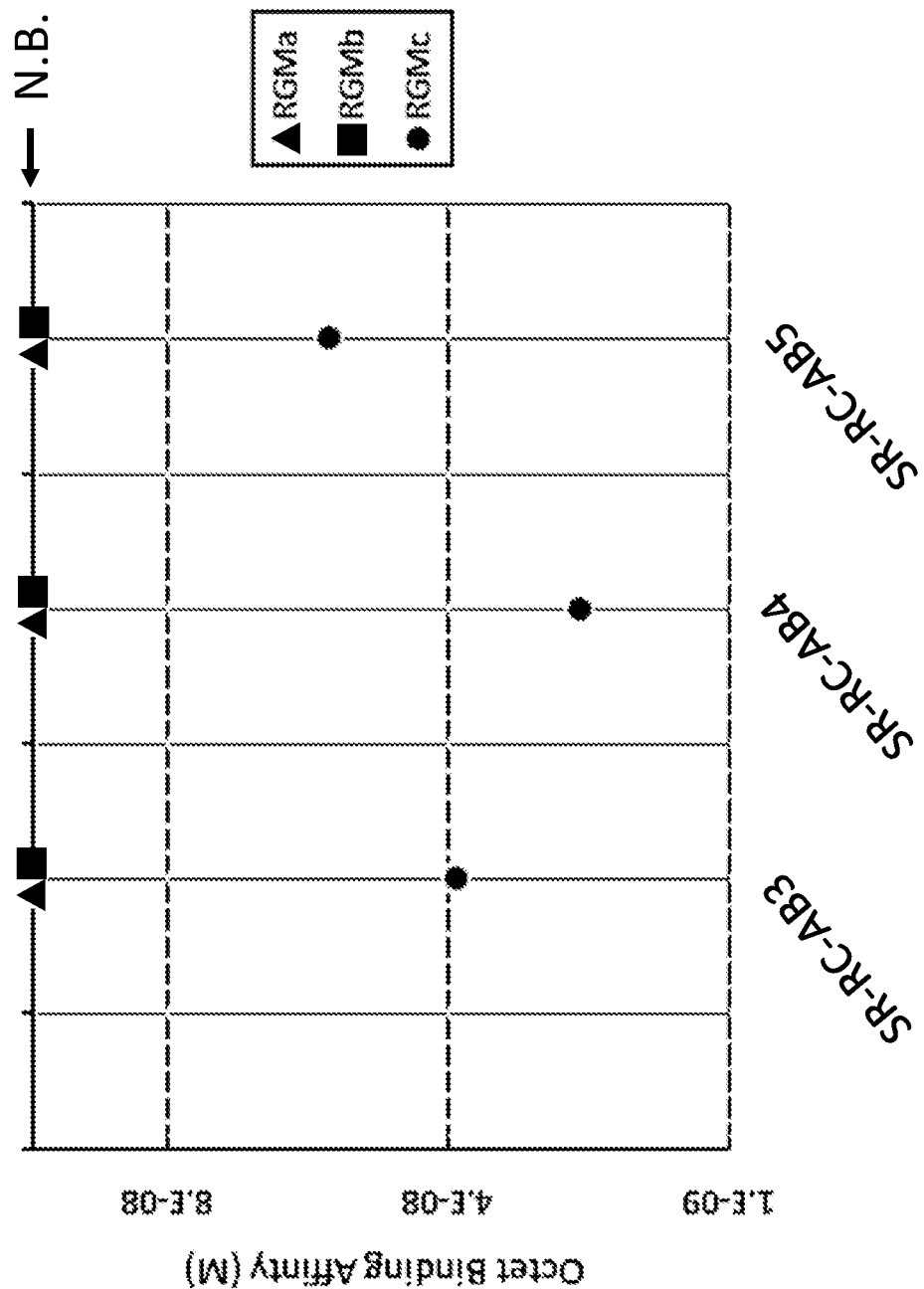
FIG. 2 is a graph that shows Octet® binding affinity of first generation RGMc-specific antibodies to RGMa, RGMb, and RGMc.
Figure 3A:
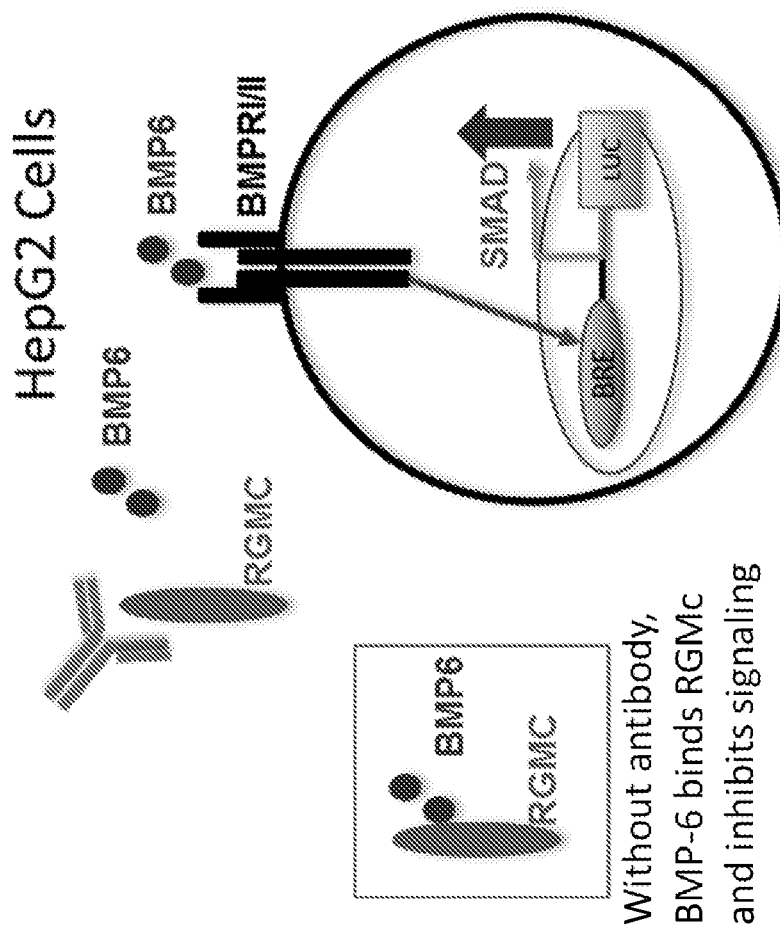
FIG. 3A is a depiction of the in vitro BMP6 activity assay using HepG2 cells. Increased BMP6 activity (mean±SD) indicates antibody-mediated inhibition of BMP6 binding to RGMc.
Figure 3B:
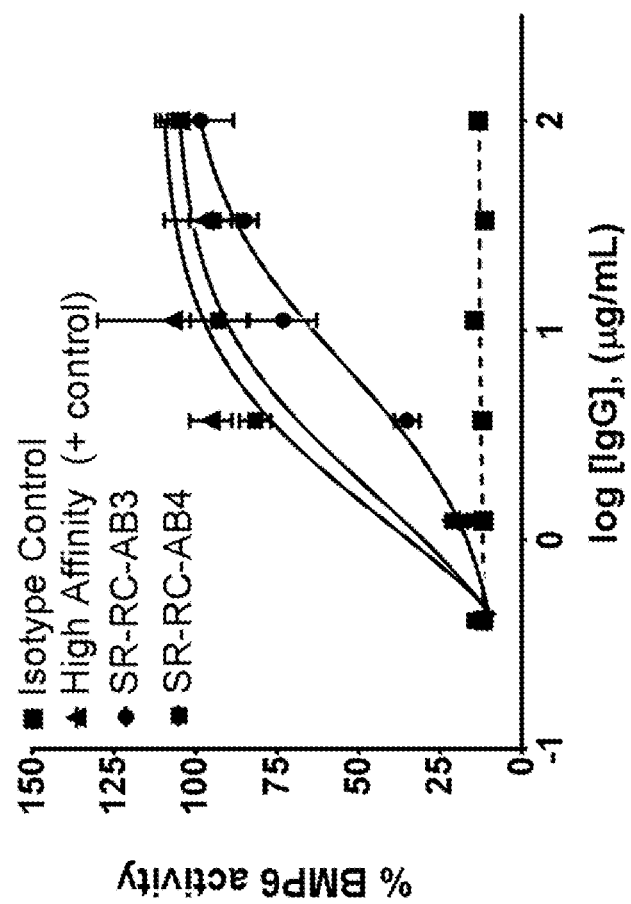
FIG. 3B is a graph that shows increased BMP6 activity (mean±SD) in the presence of SR-RC-AB3 and SR-RC- AB4. A high affinity non-specific RGM binding protein was used as a positive control, along with a negative isotype control.

FIG. 2 presents the binding profiles and affinity data ($K_D$) for RGMc-specific antibodies SR-RC-AB3, SR-RC-AB4, and SR-RC-AB5. Notably, all three antibodies bind RGMc with nanomolar affinity, while none of the antibodies displayed any detectable binding to RGMa or RGMb.

Example 2: RGMc-Selective Antibodies Inhibit BMP6 Activity In Vitro

A modified BMP reporter assay was utilized to assess antibody inhibition of BMP activity. Briefly, HEPG2BRA reporter cells were seeded at 10,000 cells/well in 96 well plates. 24 hour later, antibodies were separately pre-incubated with recombinant, soluble human RGMc fused to an Fc (CF~40 nM) for one hour in DMEM/0.1% BSA, followed by the addition of BMP6 (CF=0.2 nM) to the solution for one hour. 100 uL/well of the resulting antibody-RGMc-BMP6 complex was added to HEPG2BRA plates in triplicate, and returned to the incubator for 18 hours. 100 ul of BrightGlo™ luciferase substrate (Promega®) was added to each well and RLU was determined using a plate reader (Biotek®). Because soluble RGMc sequesters BMP6 and inhibits its downstream transcriptional activity, antibodies that block BMP6 binding to soluble RGMc activate BMP6 reporter activity in this assay, and are referred to as BMP6 competitive antibodies. Dose response titrations of SR-RC-AB3 and SR-RC-AB4 revealed them have a demonstrated potency in the BRE reporter assay with EC50's of 6.83 nM and 1.68 nM, respectively.

Example 3: Development of Affinity Matured RGMc-Selective Antibodies

SR-RC-AB3 and SR-RC-AB4 were selected for affinity maturation. Affinity maturation was conducted using known techniques, e.g., yeast display as described herein.

Figure 4A:
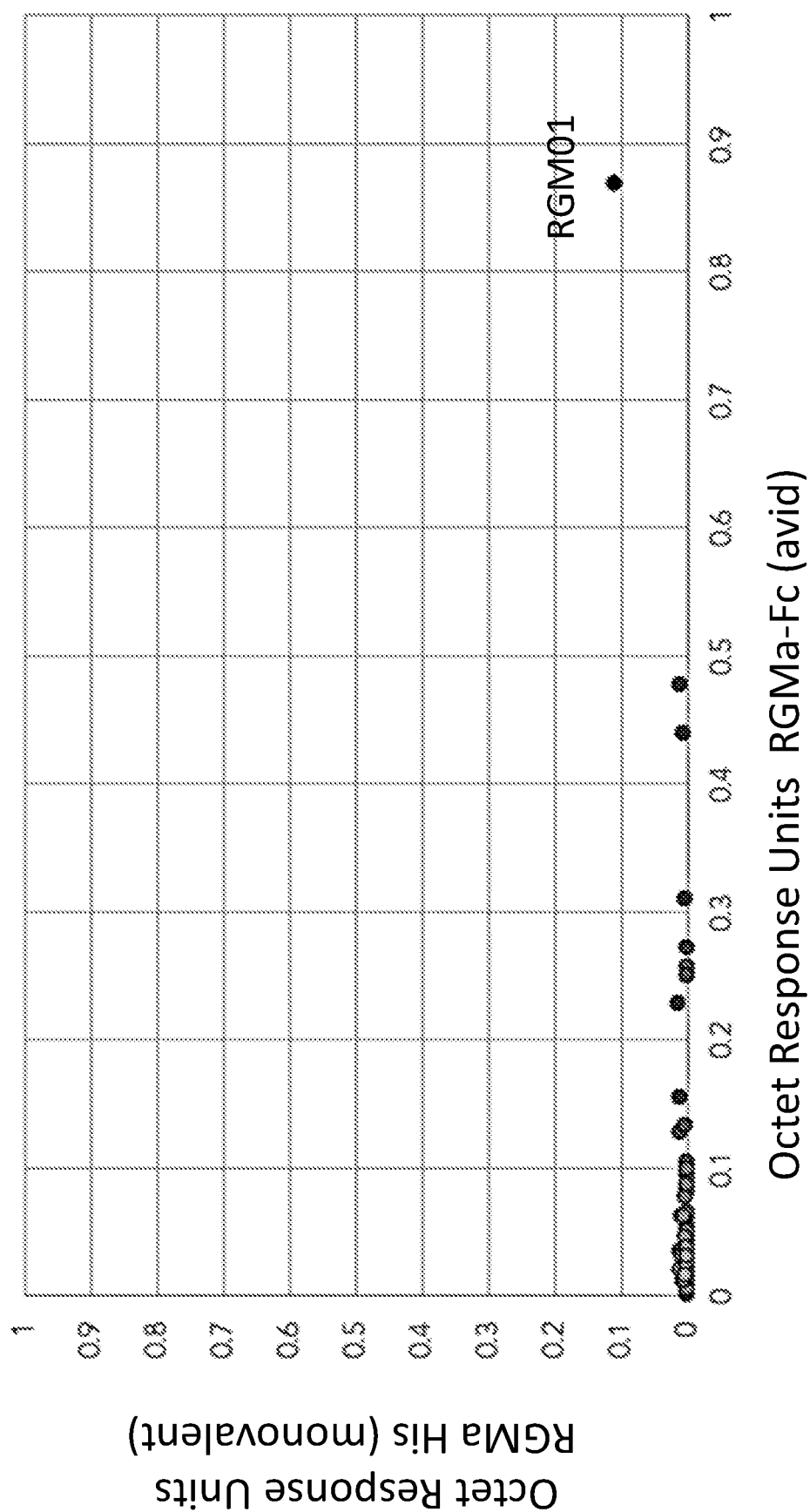
FIG. 4A is a graph that shows binding of affinity matured RGMc antibodies to RGMa-his (monovalent form) or RGMa-Fc (avid form). RGMO1 (high affinity non-specific RGM binding protein) was used as a positive control.

To determine binding affinities to either the RGMa-his (monovalent) or RGMa-Fc (avid) test antibodies were immobilized to the surface of anti-human Fc capture biosensors (AHC) (ForteBio®) and the sensors were then blocked with an excess of a negative control antibody. Binding was then tested to Fc or histidine tagged RGMa, at 100 nM. The antigens were allowed to associate for 3 minutes followed by a 3-minute dissociation. Kinetics buffer (ForteBio®) was used throughout the experiment, and $K_D$ was determined using a 1:1 fitting model for each antibody antigen pair. None of the antibodies showed binding to the histidine tagged RGMa protein while some clones did show a response to the avid (Fc-tagged form) (FIG. 4A). The clones which showed binding to the RGMa-Fc were all from the same lineage indicating a potentially cross-reactive epitope within this family. Clones having binding to RGMa-Fc where not selected for further testing.

Figure 4B:
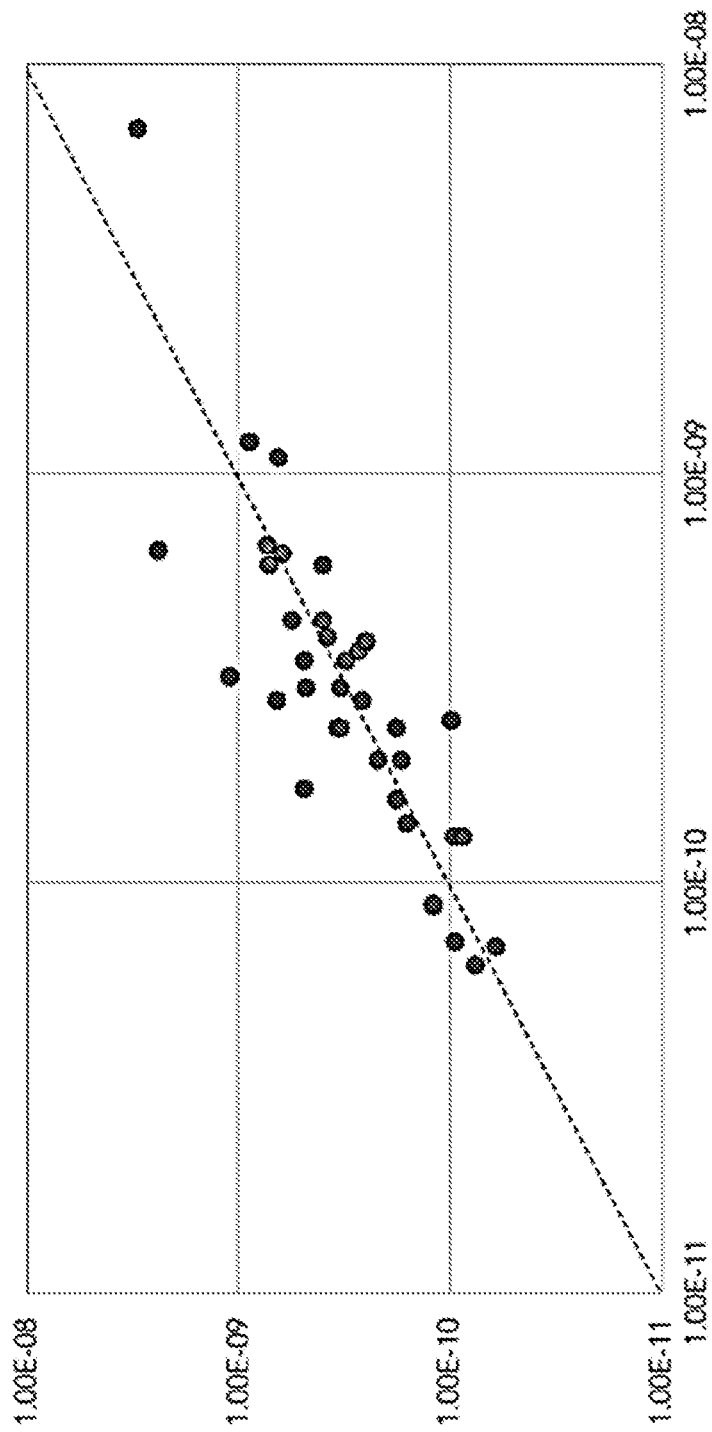
FIG. 4B shows that cross-reactivity to both the human and mouse RGMc antigens was maintained throughout the affinity maturation process

To measure affinities by MSD-SET (Mesoscale determination-solution equilibrium titration) a titration of RGMc-specific antibodies (in this case in the Fab form of the antibodies) was pre-incubated with a constant concentration of antigen for 20-24 hrs to reach equilibrium. The titration was then added to a pre-coated plate with a capture antibody (pre-labeled with an NHS-sulfotag) that depletes any free antigen from solution. After a 150 second incubation, the plate was washed 3 times and an SA-sulfotag reagent was added and incubated for 3 min. After additional washes the plate was read on a MesoQuickPlex® SQ120. Fab affinities to both the human and mouse RGMc antigens were determined and show that cross-reactivity to both species was maintained throughout the affinity maturation process (FIG. 4B).

A similar MSD-SET assay was performed with the full-length antibodies against the human RGMc-his antigen to determine binding affinity ($K_D$)). As shown in Table 3, select progeny antibodies reached sub-nanomolar affinities as compared to the parental antibodies.

The BRE-luciferase activity (which measures BMP-6 competition in vitro) was performed as described above in Example 2. As shown in Table 4, the affinity matured antibodies also showed an improvement in BMP competition, as compared to the parental antibodies.

TABLE 3

$K_D$ of RGMc affinity matured antibodies

|  |  | $K_D$ (M) |
|---|---|---|
| Parental antibodies | SR-RC-AB3 | 4.30E−9 |
|  | SR-RC-AB4 | 4.00E−9 |
| Affinity matured antibodies | SR-RC-AB7 | 2.10E−11 |
|  | SR-RC-AB8 | 3.90E−11 |
|  | SR-RC-AB9 | 2.40E−11 |

Figure 5A:
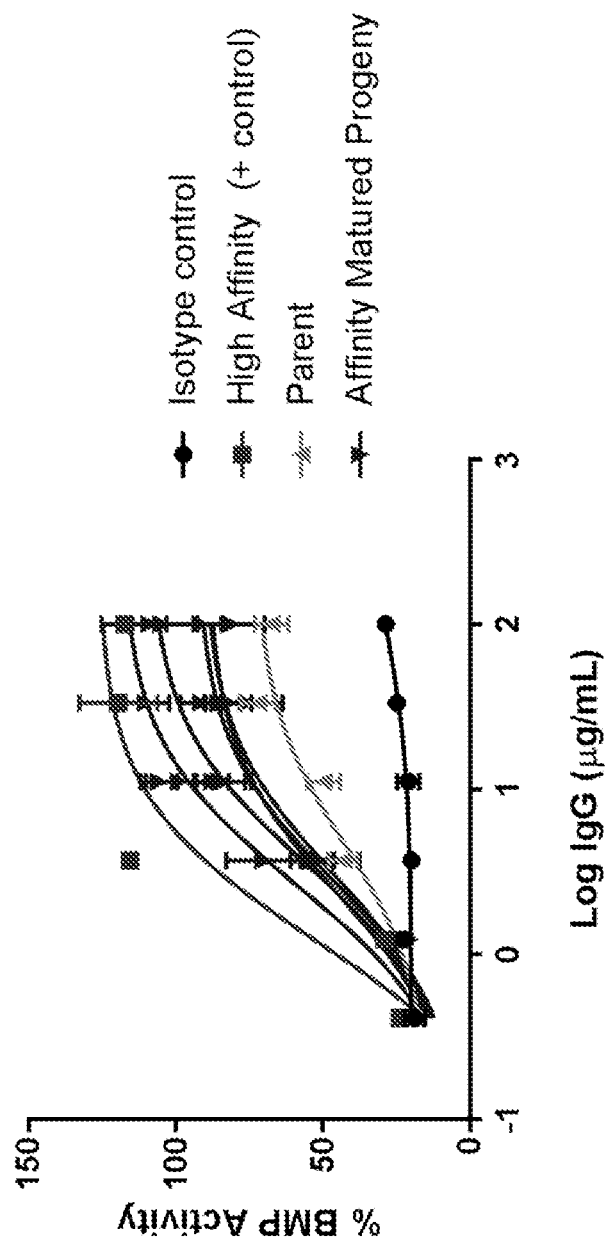
FIG. 5A is a graph that shows activity (mean±SD) of the SR-RC-AB3 family of affinity matured antibodies in the in vitro BMP6 assay.
Figure 5B:
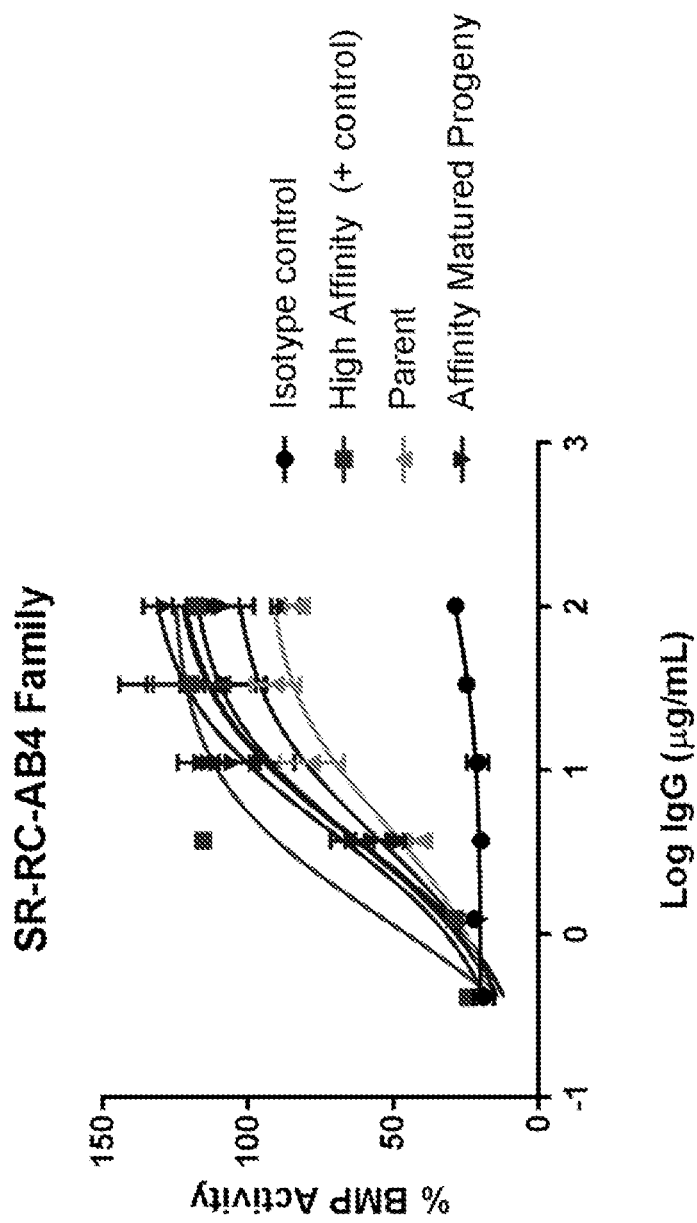
FIG. 5B is a graph that shows activity (mean±SD) of the SR-RC-AB4 family of affinity matured antibodies in the in vitro BMP6 assay. A high affinity non-specific RGM binding protein was used as a positive control, along with a negative isotype control.

Example 4: Affinity Matured RGMc-Selective Antibodies Inhibit BMP6 Activity In Vitro To determine whether the affinity matured RGMc-selective antibodies inhibited BMP6 binding to RGMc, a BMP6 assay was conducted as described above in Example 2. As shown in FIG. 5A, the SR-RC-AB3 family of affinity matured antibodies display improved ability to inhibit BMP binding to RGMc (as shown by increased BMP activity) as compared to the parent antibody (i.e., SR-RC-AB3). As shown in FIG. 5B, the SR-RC-AB4 family of affinity matured antibodies display improved ability to inhibit BMP binding to RGMc (as shown by increased relative BMP activity) as compared to the parent antibody (i.e., SR-RC-AB3). A high affinity RGM binder was used as a control, along with an isotype control. Table 4 shows the calculated EC50 values in the BMP activity assay. Together, these results indicate that the affinity-matured antibodies have improved ability to inhibit RGMc activity through BMP.

TABLE 4

Affinity matured antibodies show increased BMP competition.

|  |  | EC50 (ug/mL) |
|---|---|---|
| Parental antibodies | SR-RC-AB3 | 4.83 |
|  | SR-RC-AB4 | 5.25 |

TABLE 4-continued

Affinity matured antibodies show increased BMP competition.

|  |  | EC50 (ug/mL) |
|---|---|---|
| Affinity matured antibodies | SR-RC-AB7 | 3.87 |
|  | SR-RC-AB8 | 3.63 |
|  | SR-RC-AB9 | 3.45 |

Figure 6A:
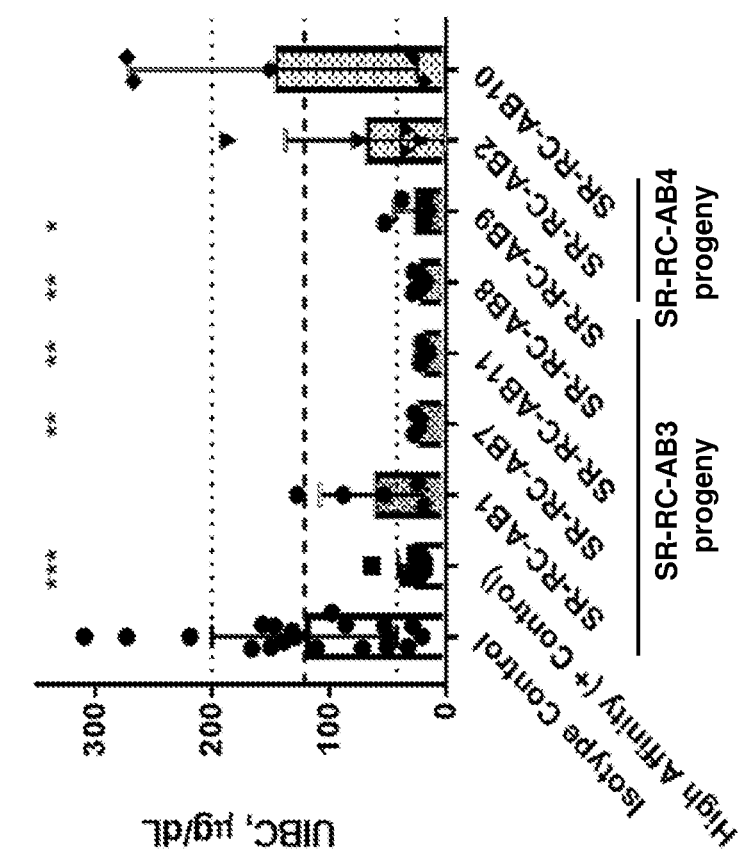
FIG. 6A is a graph that shows the effects of affinity matured antibodies on serum iron levels (mean±SD) in rats.
Figure 6B:
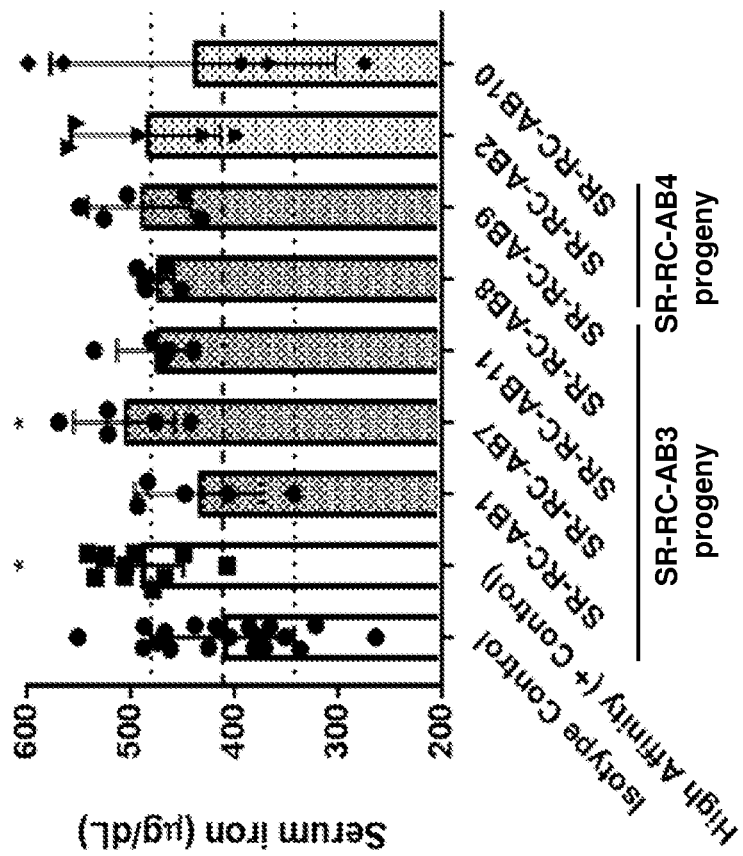
FIG. 6B is a graph that shows the effects of affinity matured antibodies on unbound iron binding capacity (UIBC) (mean±SD) in rats. A high affinity non-specific RGM binding protein was used as a positive control, along with a negative isotype control. Significance was determined by 1-way ANOVA versus isotype control; *p-value<0.05, p-value<0.01, *p-value<0.001.

Example 5: Affinity Matured RGMc-Selective Antibodies Modulate Iron Homeostasis In Vivo To evaluate in vivo effects of the antibodies, iron parameters (serum iron, Unsaturated Iron Binding Capacity (UIBC), and transferrin saturation) were measured 24 hours following a single antibody administration (0.2 mg/kg, n=5 animals/group) in rodents. Female Sprague Dawley rats (7 to 9 weeks of age, Charles River Laboratories) were administered a single i.v. dose of antibody. 24 hours later, animals were sacrificed, serum was collected for either iron analysis on a ModP or Cobas clinical chemistry analyzer or for hepcidin ELISA, and livers were harvested for analysis of hepcidin RNA expression. Select BMP-competitive antibodies robustly repressed hepcidin and increased the mobilization of iron in rodents. More specifically, as shown in FIGS. 6A and 6B, SR-RC-AB1, SR-RC-AB7, SR-RC-11, SR-RC-AB8, SR-RC-AB9, SR-RC-AB2, and SR-RC-AB10, increased serum iron in rats as compared to control and reduced unsaturated iron binding capacity (UIBC) in healthy rats. Data demonstrate that RGMc-selective inhibitors according to the present invention are effective in mobilizing iron in vivo (FIG. 6A), by significantly reducing unsaturated iron binding capacity (UIBC) (FIG. 6B) and achieving significant increase in transferrin saturation at 0.2 mg/kg after 24 hours in rats.

To examine the pharmacokinetic (PK) and pharmacodynamic (PD) relationship of RGMc selective antibodies, single dose PK/PD studies were conducted in female Sprague Dawley rats. Animals were administered a single intravenous (IV) dose of antibody at 0.6, 2, 6 and 20 mg/kg and serum iron parameters (e.g., serum iron and UIBC levels) were determined as pharmacodynamic measures whereas antibody serum concentrations were measured to determine the PK profile of the antibody. Serum iron and UIBC were determined by RX Daytona Clinical Chemistry Analyzer and antibody concentrations were measured by ELISA.

Figure 7A:
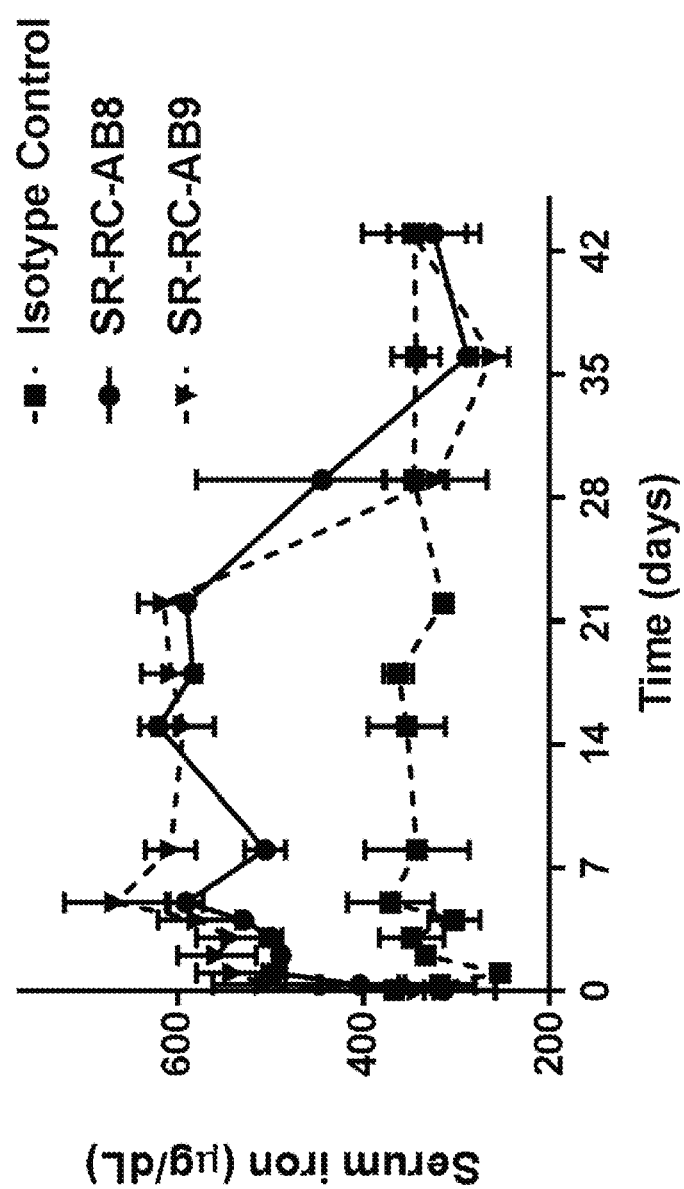
FIG. 7A is a graph that shows serum iron levels (mean±SEM) in female Sprague-Dawley rats over time when treated with a single dose of SR-RC-AB8 or SR-RC-AB9 at 20 mg/kg. An isotype antibody was used as a control.
Figure 7B:
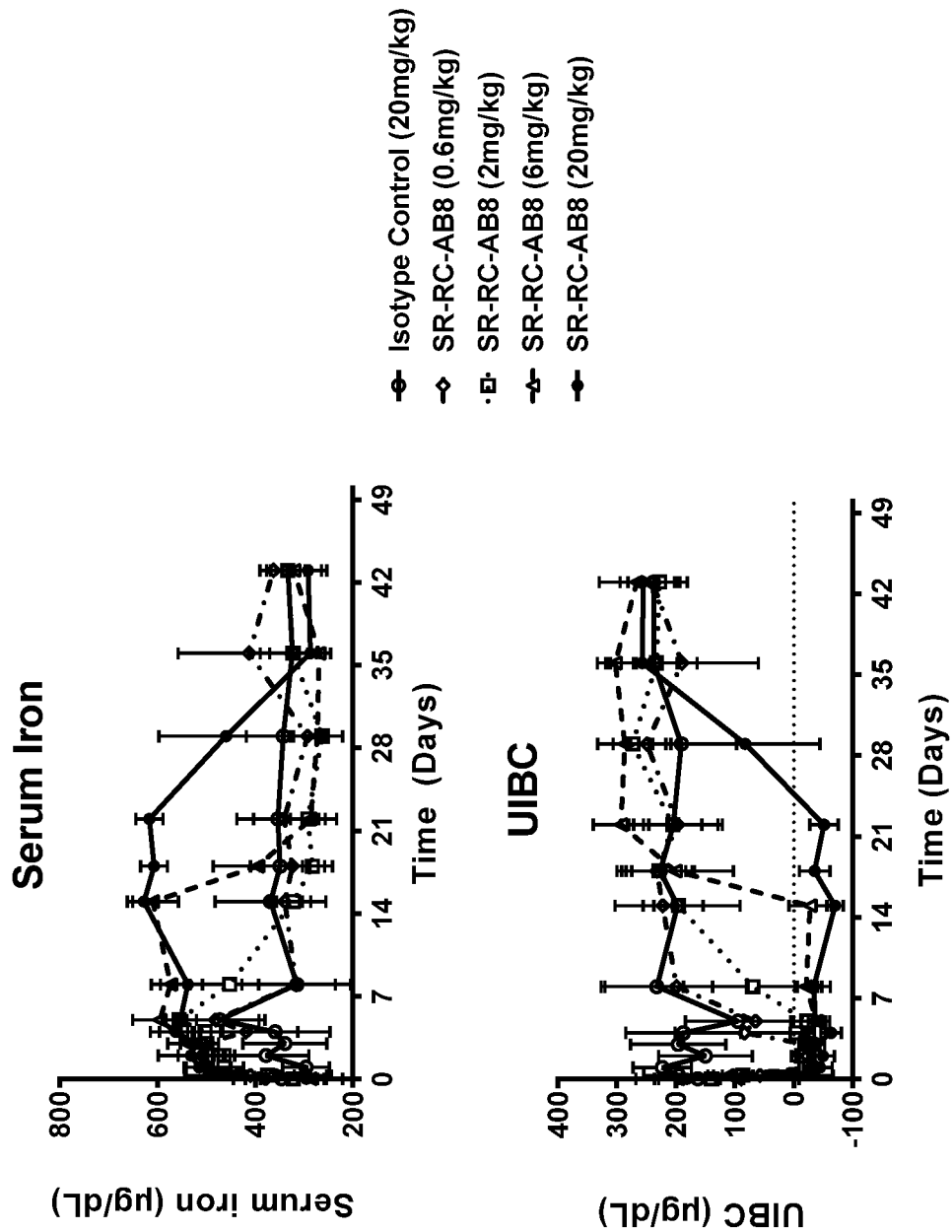
FIG. 7B shows serum iron (top) and UIBC (bottom) measurements (mean±SEM) in PK/PD studies wherein female Sprague-Dawley rats were administered single IV dose of SR-RC-AB8 at 0.6 mg/kg to 20 mg/kg (n=5-11 animals/group).
Figure 7D:
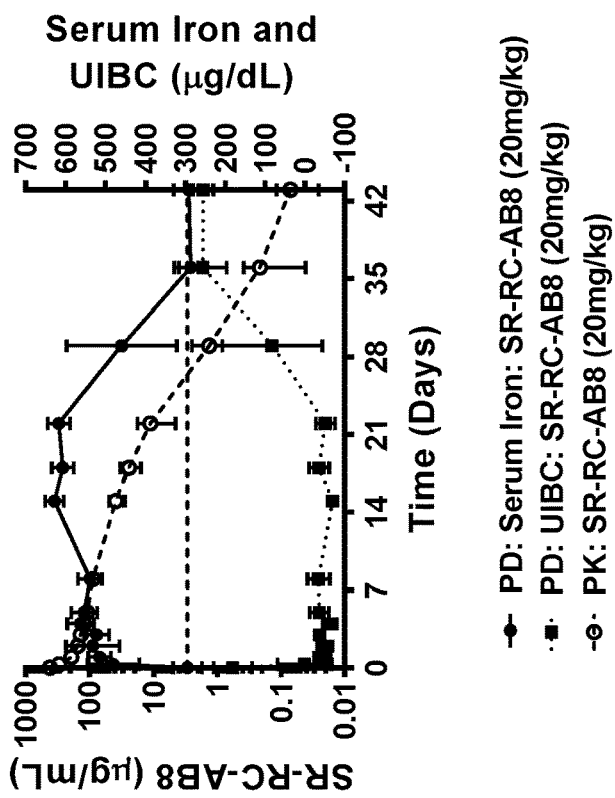
FIG. 7D illustrates the relationship between antibody exposure (PK) and iron parameters (PD) at 20 mg/kg (all values are mean±SEM).
Figure 7C:
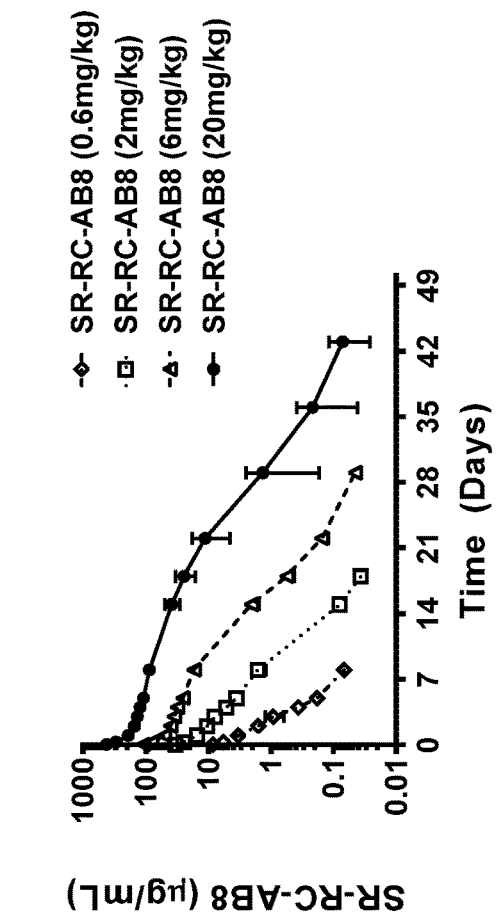
FIG. 7C shows the antibody serum concentrations (mean±SEM) within the same animals as in FIG. 7B.

FIG. 7A shows serum iron levels (mean±SEM) in animals over time when treated with a single dose of SR-RC-AB8 (n=2) or SR-RC-AB9 (n=5) at 20 mg/kg. SR-RC-AB8 and SR-RC-AB9 increased serum iron levels and reduced UIBC levels compared to control. FIG. 7B shows serum iron (top) and UIBC (bottom) measurements in follow up PK/PD studies wherein female Sprague-Dawleyere administered single IV dose of SR-RC-AB8 at 0.6 mg/kg to 20 mg/kg (n=5-11 animals/group). SR-RC-AB8 increased serum iron levels and reduced UIBC levels at all doses evaluated compared to control The duration of the changes in serum iron parameters was dose-dependent wherein the effects were sustained as long as 21 days following single dose of 20 mg/kg. FIG. 7C shows the antibody serum concentrations within the same animals. PK parameters were calculated using Phoenix WinNonlin software and summarized in Table 5. Target-mediated drug disposition (TMDD) is observed at all dose levels, however at higher doses of 6 and 20 mg/kg the target appears to be saturated at early time points and the observation of TMDD and the timing of change in clearance is noted at later timepoints in the PK profile. The maximum concentration is achieved at 1 hr post-dose, and the $C_{max}$ demonstrated a dose proportional increase. The half-life of the antibody ranges from 1.2-6.7 days, indicating the faster clearance and shorter residence times observed at lower doses. This is consistent with human IgG4 molecules with target-mediated drug disposition (TMDD). Lastly, as expected with a molecule that exhibits TMDD, a more than dose proportional increase in exposure as measured by $AUC_{0-8}$ was observed. FIG. 7D illustrates the relationship between antibody exposure (PK) and serum iron parameters (PD) at 20 mg/kg. Data suggests that the concentrations above 3p g/mL are needed for continuous PD effect.

| Dose (mg/kg) | n | $T_{1/2}$ Mean (SD) (Days) | $C_{max}$ (SD) (μg/mL) | $T_{max}$ (Day) | $AUC_{0-8}$ (SD) (day*μg/mL) |
|---|---|---|---|---|---|
| 0.6 | 5 | 1.18 (0.0926) | 8.54 (0.696) | 0.004 | 10.3 (0.353) |
| 2 | 5 | 2.22 (0.223) | 33.9 (4.42) | 0.004 | 63.4 (6.5) |
| 6 | 5 | 4.7 (0.207) | 111 (3.78) | 0.004 | 284 (11.7) |
| 20 | 7 | 6.62 (1.13) | 420 (46.6) | 0.004 | 1140 (80.2) |

Together, these data demonstrate that targeted disruption of the BMP6-hepcidin signaling pathway by RGMc-specific antibodies increases the availability of iron in vivo. These results support the notion that liver-selective inhibition of BMP6 signaling may provide a safe and effective way to target a variety of iron-restricted anemias, including anemia of CKD and cancer- or chemotherapy-induced anemia.

Example 6: HDX Epitope Mapping to Determine RGMc-Selective Antibody Binding Regions Hydrogen/Deuterium exchange mass spectrometry (HDX-MS) is a widely used technique for exploring protein conformation in solution. HDX-MS methodology is described in Wei et al., Drug Discov Today, 2014 January; 19(1): 95-102, incorporated by reference in its entirety herein. Briefly, HDX-MS relies on the exchange of the protein backbone amide hydrogens with deuterium in solution. The backbone amide hydrogens involved in weak hydrogen bonds or located at the surface of the protein may exchange rapidly while those buried in the interior or those involved in stabilizing hydrogen bonds exchange more slowly. By measuring hydrogen/deuterium (H/D) exchange rates of backbone amide hydrogens, one can obtain information on protein dynamics and conformation.

HDX-MS was carried out to determine where in the RGMc SR-RC-AB9 is binding. In HDX-MS, the regions of an antigen that are tightly bound by an antibody are protected from H/D exchange, due to protein-protein interaction, while regions that are exposed to solvent can readily undergo H/D exchange. Based on this, binding regions of the antigen were identified. FIG. 8A shows two H/D exchange protected regions suggesting that SR-RC-AB9 potentially binds to a unique epitope comprising two binding regions (region A and region B) in the α1 and α3 helices of RGMc, respectively. The α3 helix includes part of the BMP binding domain. FIG. 8B is an alignment of RGMa/b/c peptides corresponding to region A and region B. FIG. 8C shows the structure of the RGMc modeled after the known RGMa structure bound to BMP2.

Indeed, the RGMc-specific antibodies may bind to the α3 helix (e.g., region B) based on the presence of potential contact residues (see, e.g., FIG. 8D). Moreover, there are several amino acid variations among the isoforms, particularly in the al helix, that likely contribute to the isoform specificity of SR-RC-AB3 progeny antibodies (e.g., SR-RC-AB8 and SR-RC-AB9). Likewise, there are several residues within region A that may serve as structural determinant of RGMc specificity over RGMa and RGMb (FIG. 8E).

Example 7: RGMC-Selective Antibodies Modulate Iron Homeostasis in Non-Human Primates To evaluate the ability of RGMC-selective antibodies to modulate iron homeostasis in non-human primates, serum iron parameters were measured following a single I.V. dose of SR-RC-AB8 at 10 mg/kg in female Cynomolgus macaques (2-7 years of age, Covance). Serum was collected from animals at regular intervals for 10 weeks following the single antibody dose. Serum iron and UIBC were measured on a Cobras blood analyzer, and serum antibody exposure determined by ELISA.

SR-RC-AB8 effectively increased serum iron and decreased UIBC following antibody administration and serum iron levels remained elevated through 6 weeks following dosing as shown in FIG. 9A. By 8 weeks, the serum iron in all animals dosed with SR-RC-AB8 had returned to baseline. FIG. 9B shows the average serum concentration of SR-RC-AB8 up to 10 weeks after dosing. PK profile was as expected for a monoclonal antibody with $C_{max}$ of 242 µg/mL (±21.3) achieved 1 hr post-dose. The PK/PD relationship evaluated by comparing antibody exposure (PK) to serum iron parameters (PD) suggests that the concentrations above 3p g/mL can produce continuous or prolonged PD effect (FIG. 9C).

These results confirm that RGMC-selective antibodies can have a sustained effect on serum iron in non-human primates following a single dose of antibody, which may enable opportunities for infrequent IV infusion (for example every 3 months or 6 months) and/or subcutaneous dosing regimens.

Example 8: RGMC-Selective Antibodies Modulate Serum Iron and Increase Hemoglobin when Dosed in Combination with an ESA in a Rat Model of Anemia of Chronic Disease To examine the effect of RGMC-selective antibodies on serum iron and blood parameters in a model of anemia of chronic disease (ACD), the Lewis PG-APS ACD model was used. This is a long-lasting model of anemia of chronic disease in rats, thus enabling the investigation of the effect of hepcidin modulating drugs on erythropoiesis. Due to the potential of RGMC-selective antibodies to enhance the function of ESAs, antibodies were dosed alone and in combination with epoetin alpha (EPO). Arthritis was induced in rats with PG-APS [15 mg/kg] i.p. and after 14 days blood and serum iron parameters were determined. Based on these results, rats were randomized into groups for dosing, with the first day of dosing labeled as day 0. Animals (n=6-8 per group) were treated with isotype control or SR-RC-AB8 antibodies (20 mg/kg) and/or EPO (10 ug/kg) weekly. Animals were dosed for a total of 4 weeks (day 0, 7, 14, 21), and serum iron and blood parameters were measured weekly at days 3, 10, 17, 24 and 28.

Figure 10A:
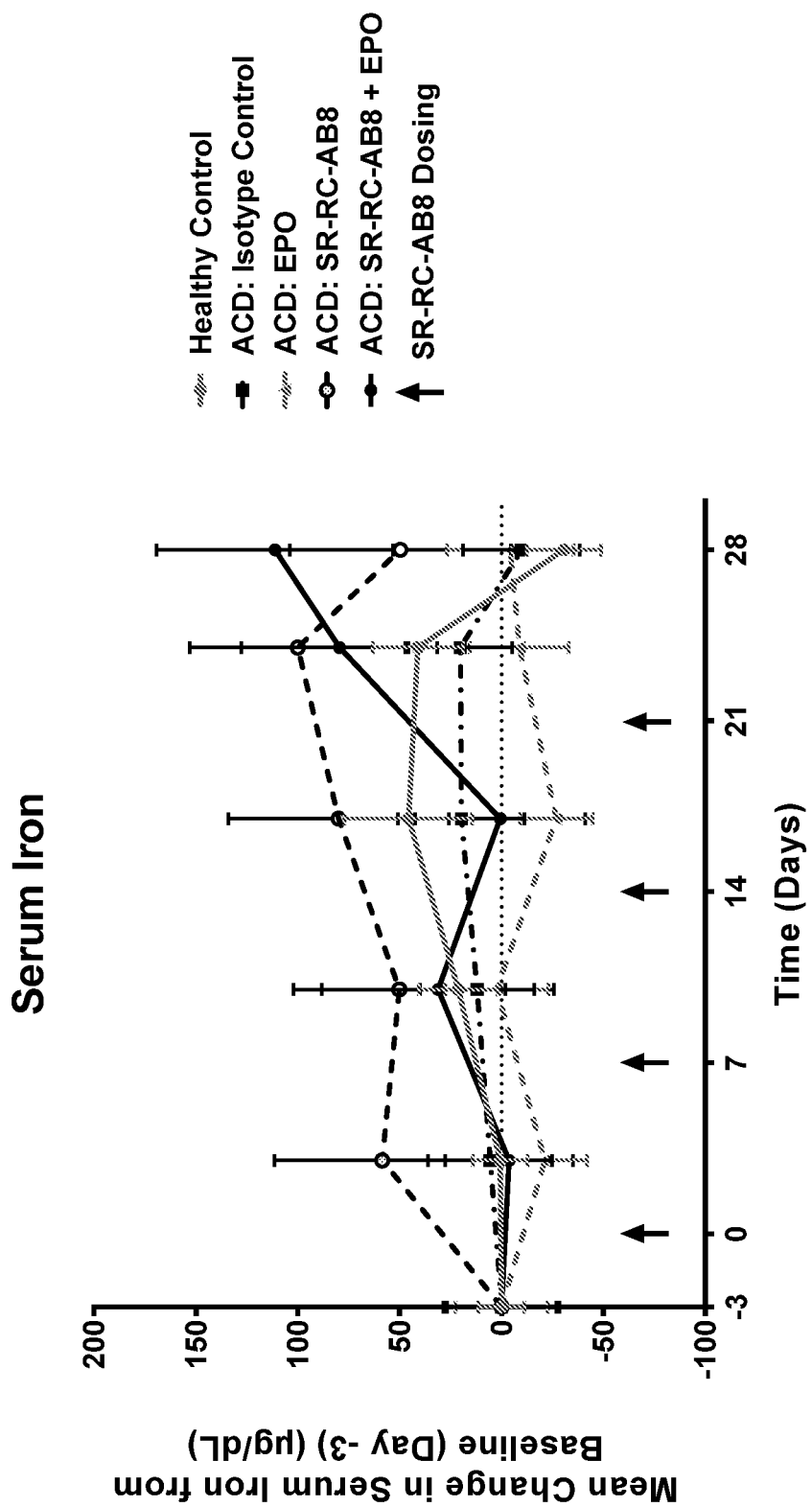
FIG. 10A shows the change in serum iron from baseline at day −3 (mean±SEM) with weekly injection of SR-RC-AB8 at 20 mg/kg alone or in combination with epoietin alpha (EPO) (10 µg/kg) in the PGPS model of Anemia of Chronic Disease (ACD) in female Lewis rats.
Figure 10B:
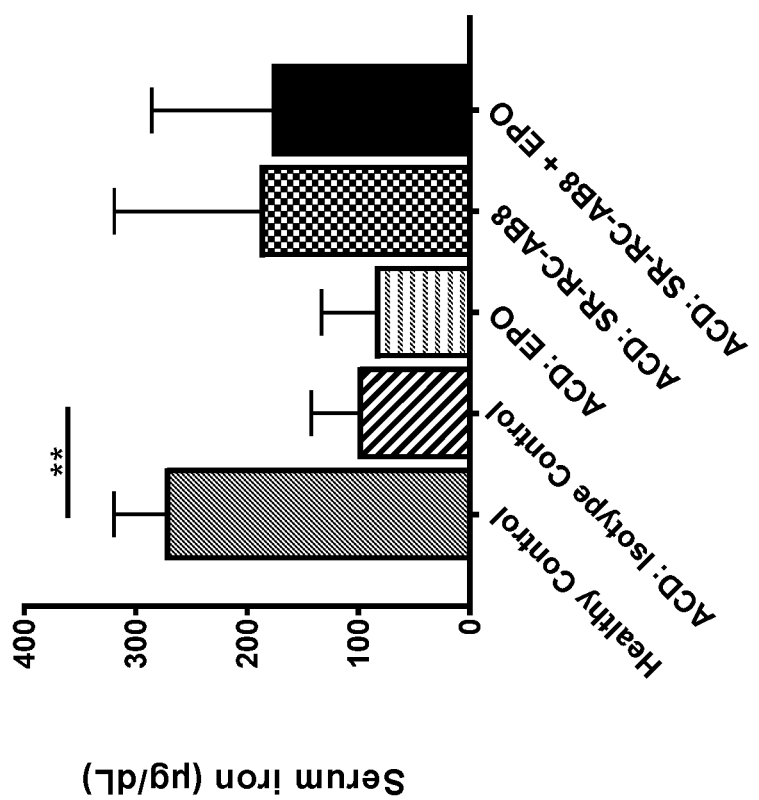
FIG. 10B (mean±SD) shows the absolute serum iron levels at day 24. Significance was determined by 1-way ANOVA versus ACD isotype control; p-value<0.01.
Figure 10C:
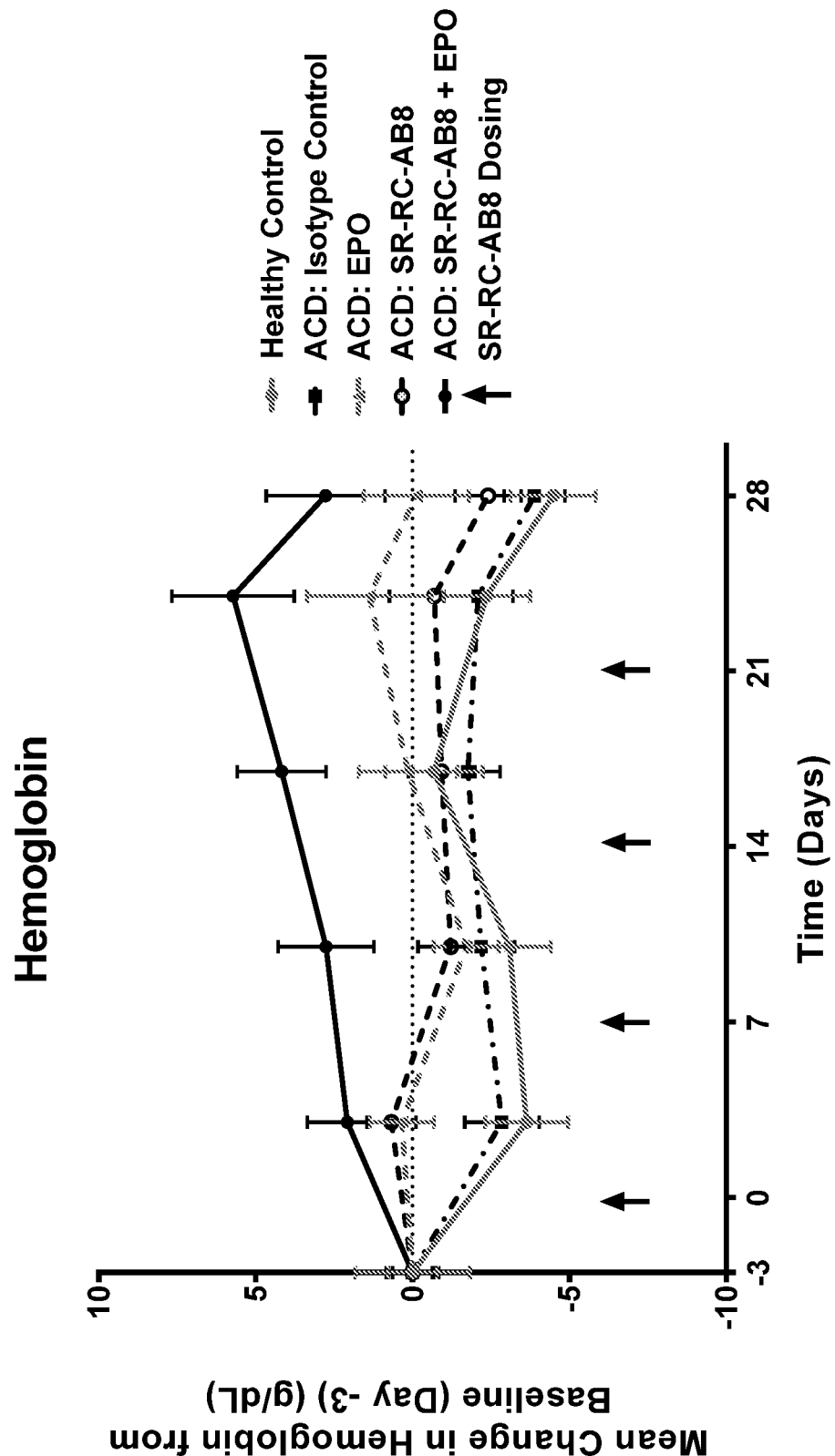
FIG. 10C demonstrates the change in hemoglobin from baseline measurement at day −3 (mean±SEM) in response to weekly dosing of SR-RC-AB8 (20 mg/kg), EPO (10 µg/kg) or both. The absolute hemoglobin levels (mean±SD) on day 24 are shown in FIG. 10D. Significance was determined by 1-way ANOVA versus ACD isotype control; p-value<0.01.

FIG. 10A shows the change in serum iron from baseline measurements at day −3 for each dose group. Dosing weekly with SR-RC-AB8 alone and in combination with EPO increased serum iron compared to IgG alone in ACD animals. FIG. 10B shows the absolute serum iron (µg/dL) data from day 24 of the study. Note the significant difference in serum iron between healthy controls and ACD animals and the increased serum iron in animal groups dosed with SR-RC-AB8. FIG. 10C illustrates the change in hemoglobin from baseline measurements at day −3 for each dose group. The data show that when dosed in combination with EPO, SR-RC-AB8 had a robust effect on hemoglobin, increasing levels faster and higher on average than EPO or antibody alone. Absolute hemoglobin (g/dL) data from day 24 alone is illustrated in FIG. 10D. There was a 58% increase in hemoglobin in the ACD: SR-RC-AB8+EPO dose group when compared to ACD: Isotype control group. Together these data show that in a model of ACD, SR-RC-AB8 can modulate serum iron and when dosed in combination with EPO, SR-RC-AB8 may have an even greater effect than EPO alone in modulating Hgb.

Listing of certain sequences included in the present disclosure is provided below.

SEQUENCE LISTING

| NAME | AMINO ACID SEQUENCE | SEQ ID NO: |
|------|---------------------|------------|
| Human RGMc isoform a (NP_998818) | mgepgqspsp rsshgspptl stltllllllc ghahsqckil rcnaeyvsst lslrgggssg alrggggggr gggvgsgglc ralrsyalct rrtartcrgd lafhsavhgi edlmiqhncs rqgptapppp rgpalpgags glpapdpcdy egrfsrlhgr ppgflhcasf gdphvrsfhh hfhtcrvqga wplldndflf vqatsspmal ganatatrkl tiifknmqec idqkvyqaev dnlpvafedg singgdrpgg sslsiqtanp gnhveiqaay igttiiirqt agqlsfsikv aedvamafsa eqdlqlcvgg cppsqrlsrs ernrrgaiti dtarrlckeg lpvedayfhs cvfdvlisgd pnftvaaqaa ledaraflpd leklhlfpsd agvplssatl lapllsglfv lwlciq | 1 |
| Human RGMc isoform b (NP_660320) | miqhncsrqg ptappprgp alpgagsglp apdpcdyegr fsrlhgrppg flhcasfgdp hvrsfhhhfh tcrvqgawpl ldndflfvqa tsspmalgan atatrkltii fknmqecidq kvyqaevdnl pvafedgsin ggdrpggssl siqtanpgnh veiqaayigt tiiirqtagq lsfsikvaed vamafsaeqd lqlcvggcpp sqrlsrsern rrgaitidta rrlckeglpv edayfhscvf dvlisgdpnf tvaaqaaled araflpdlek lhlfpsdagv plssatllap llsglfvlwl ciq | 2 |

SEQUENCE LISTING

| NAME | AMINO ACID SEQUENCE | SEQ ID NO: |
|---|---|---|
| Human RGMc isoform c (NP_998817) | mqecidqkvy qaevdnlpva fedgsinggd rpggsslsiq tanpgnhvei qaayigttii irqtagqlsf sikvaedvam afsaeqdlql cvggcppsqr lsrsernrrg aitidtarrl ckeglpveda yfhscvfdvl isgdpnftva aqaaledara flpdleklhl fpsdagvpls satllaplls glfvlwlciq | 3 |
| Human RGMa (NP_001159755) | mgglgprrag tsrerlvvtg ragwmgmgrg agrsalgfwp tlafllcsfp aatspckilk cnsefwsats gshapasddt pefcaalrsy alctrrtart crgdlayhsa vhgiedlmsq hncskdgpts qprlrtlppa gdsgersdsp eichyeksfh khsatpnyth cglfgdphlr tftdrfqtck vqgawplidn nylnvqvtnt pvlpgsaata tskltiifkn fqecvdqkvy qaemdelpaa fvdgsknggd khganslkit ekvsgqhvei qakyigttiv vrqvgryltf avrmpeevvn avedwdsqgl ylclrgcpin qqidfqafht naegtgarrl aaaspaptap etfpyetava kckeklpved lyyqacvfdl lttgdvnftl aayyaledvk mlhsnkdklh lyertrdlpg raaaglplap rpllgalvpl lallpvfc | 4 |
| Human RGMNb (NP_001012779) | mirkkrkrsa ppgpershgp rpatapappp speptrpawt gmglraapss aaaaaaeveq rrspglcppp lellllllfs lgllhagdcq qpaqcriqkc ttdfvsltsh lnsavdgfds efckalraya gctqrtskac rgnlvyhsav lgisdlmsqr ncskdgptss tnpevthdpc nyhshagare hrrgdqnpps ylfcglfgdp hlrtfkdnfq tckvegawpl idnnylsvqv tnvpvvpgss atatnkitii fkahhectdq kvyqavtddl paafvdgtts ggdsdakslr iveresghyv emharyigtt vfvrqvgryl tlairmpedl amsyeesqdl qlcvngcpls eriddgqgqv sailghslpr tslvqawpgy tletantqch ekmpvkdiyf qscvfdlltt gdanftaaah saledvealh prkerwhifp ssgngtprgg sdlsyslglt clilivfl | 5 |
| SR-RC-AB1 CDR-H1 | GTFSSYSIS | 6 |
| SR-RC-AB1 CDR-H2 | GIIPIFGVASYAQKFQG | 7 |
| SR-RC-AB1 CDR-H3 | ARGAIAATYGLGMDV | 8 |
| SR-RC-AB1 CDR-L1 | QASQDISNYLN | 9 |
| SR-RC-AB1 CDR-L2 | DASNLET | 10 |
| SR-RC-AB1 CDR-L3 | QQLVDLPPT | 11 |
| SR-RC-AB1 Variable heavy chain | QVQLVQSGAE VKKPGSSVKV SCKASGGTFS SYSISWVRQA PGQGLEWMGG IIPIFGVASY AQKFQGRVTI TADESTSTAY MELSSLRSED TAVYYCARGA IAATYGLGMD VWGQGTTVTV SS | 12 |
| SR-RC-AB1 Variable light chain | DIQMTQSPSS LSASVGDRVT ITCQASQDIS NYLNWYQQKP GKAPKLLIYD ASNLETGVPS RFSGSGSGTD FTFTISSLQP EDIATYYCQQ LVDLPPTFGG GTKVEIK | 13 |
| SR-RC-AB3 CDR-H1 | GTFSSYAIS | 14 |
| SR-RC-AB3 CDR-H2 | GIIPIFGTANYAQKFQG | 15 |
| SR-RC-AB3 CDR-H3 | ARGAIAATYGLGMDV | 16 |
| SR-RC-AB3 CDR-L1 | QASQDISNYLN | 17 |
| SR-RC-AB3 CDR-L2 | DASNLET | 18 |

| SEQUENCE LISTING | | |
|---|---|---|
| NAME | AMINO ACID SEQUENCE | SEQ ID NO: |
| SR-RC-AB3 CDR-L3 | QQLVDLPPT | 19 |
| SR-RC-AB3 Variable heavy chain | QVQLVQSGAE VKKPGSSVKV SCKASGGTFS SYAISWVRQA PGQGLEWMGG IIPIFGTANY AQKFQGRVTI TADESTSTAY MELSSLRSED TAVYYCARGA IAATYGLGMD VWGQGTTVTV SS | 20 |
| SR-RC-AB3 Variable light chain | DIQMTQSPSS LSASVGDRVT ITCQASQDIS NYLNWYQQK PGKAPKLLIY DASNLETGVP SRFSGSGSGT DFTFTISSLQ PEDIATYYCQ QLVDLPPTFG GGTKVEIK | 21 |
| SR-RC-AB7 CDR-H1 | GTFSSYAIQ | 22 |
| SR-RC-AB7 CDR-H2 | GIIPIFGVASYAQKFQG | 23 |
| SR-RC-AB7 CDR-H3 | ARGAIVATYGLGMDV | 24 |
| SR-RC-AB7 CDR-L1 | QASQDISNYLN | 25 |
| SR-RC-AB7 CDR-L2 | DASNLET | 26 |
| SR-RC-AB7 CDR-L3 | QQLVDLPPT | 27 |
| SR-RC-AB7 Variable heavy chain | QVQLVQSGAE VKKPGSSVRV SCKASGGTFS SYAIQWVRQA PGQGLEWMGG IIPIFGVASY AQKFQGRVTI TADESTSTAY MELSSLRSED TAVYYCARGA IVATYGLGMD VWGQGTTVTV SS | 28 |
| SR-RC-AB7 Variable light chain | DIQMTQSPSS LSASVGDRVT ITCQASQDIS NYLNWYQQKP GKAPKLLIYD ASNLETGVPS RFSGSGSGTD FTFTISSLQP EDIATYYCQQ LVDLPPTFGG GTKVEIK | 29 |
| SR-RC-AB8 CDR-H1 | GTFRSYSIS | 30 |
| SR-RC-AB8 CDR-H2 | GIIPIFGVANYAQKFQG | 31 |
| SR-RC-AB8 CDR-H3 | ARGAYEATYGLGMDV | 32 |
| SR-RC-AB8 CDR-L1 | QASQDISNYLN | 33 |
| SR-RC-AB8 CDR-L2 | DASNLET | 34 |
| SR-RC-AB8 CDR-L3 | QQLVDLPPT | 35 |
| SR-RC-AB8 Variable heavy chain | QVQLVQSGAE VKKPGSSVKV SCKASGGTFR SYSISWVRQA PGQGLEWMGG IIPIFGVANY AQKFQGRVTI TADESTSTAY MELSSLRSED TAVYYCARGA YEATYGLGMD VWGQGTTVTV SS | 36 |
| SR-RC-AB8 Variable light chain | DIQMTQSPSS LSASVGDRVT ITCQASQDIS NYLNWYQQKP GKAPKLLIYD ASNLETGVPS RFSGSGSGTD FTFTISSLQP EDIATYYCQQ LVDLPPTFGG GTKVEIK | 37 |
| SR-RC-AB9 CDR-H1 | GTFSSYSIQ | 38 |
| SR-RC-AB9 CDR-H2 | GIIPIFGVASYAQKFQG | 39 |
| SR-RC-AB9 CDR-H3 | ARGAIAATYGLGMDV | 40 |

-continued

| NAME | AMINO ACID SEQUENCE | SEQ ID NO: |
|---|---|---|
| SR-RC-AB9 CDR-L1 | QASQDISNYLN | 41 |
| SR-RC-AB9 CDR-L2 | DASNLET | 42 |
| SR-RC-AB9 CDR-L3 | QQLVDLPPT | 43 |
| SR-RC-AB9 Variable heavy chain | QVQLVQSGAE VKKPGSSVKV SCKASGGTFS SYSIQWVRQA PGQGLEWMGG IIPIFGVASY AQKFQGRVTI TADESTSTAY MELSSLRSED TAVYYCARGA IAATYGLGMD VWGQGTTVTV SS | 44 |
| SR-RC-AB9 Variable light chain | DIQMTQSPSS LSASVGDRVT ITCQASQDIS NYLNWYQQKP GKAPKLLIYD ASNLETGVPS RFSGSGSGTD FTFTISSLQP EDIATYYCQQ LVDLPPTFGG GTKVEIK | 45 |
| RGMc binding region A | YVSSTLSL | 46 |
| RGMc binding region B | FHSAVHGIEDL | 47 |
| IgG1 like hinge sequence | CPPCP | 48 |

The invention claimed is:

1. An antibody or antigen-binding fragment thereof that binds to Repulsive Guidance Molecule C (RGMc) comprising three heavy chain complementarity determining regions (H-CDRs), H-CDR1, H-CDR2, and H-CDR3, and three light chain CDRs, L-CDR1, L-CDR2, and L-CDR3, wherein:

i) the H-CDR1 comprises the amino sequence of SEQ ID NO: 30, the H-CDR2 comprises the amino sequence of SEQ ID NO: 31, the H-CDR3 comprises the amino sequence of SEQ ID NO: 32, the L-CDR1 comprises the amino sequence of SEQ ID NO: 33, the L-CDR2 comprises the amino sequence of SEQ ID NO: 34, and the L-CDR3 comprises the amino sequence of SEQ ID NO: 35;

ii) the H-CDR1 comprises the amino sequence of SEQ ID NO: 6, the H-CDR2 comprises the amino sequence of SEQ ID NO: 7, the H-CDR3 comprises the amino sequence of SEQ ID NO: 8, the L-CDR1 comprises the amino sequence of SEQ ID NO: 9, the L-CDR2 comprises the amino sequence of SEQ ID NO: 10, and the L-CDR3 comprises the amino sequence of SEQ ID NO: 11;

iii) the H-CDR1 comprises the amino sequence of SEQ ID NO: 14, the H-CDR2 comprises the amino sequence of SEQ ID NO: 15, the H-CDR3 comprises the amino sequence of SEQ ID NO: 16, the L-CDR1 comprises the amino sequence of SEQ ID NO: 17, the L-CDR2 comprises the amino sequence of SEQ ID NO: 18, and the L-CDR3 comprises the amino sequence of SEQ ID NO: 19;

iv) the H-CDR1 comprises the amino sequence of SEQ ID NO: 22, the H-CDR2 comprises the amino sequence of SEQ ID NO: 23, the H-CDR3 comprises the amino sequence of SEQ ID NO: 24, the L-CDR1 comprises the amino sequence of SEQ ID NO: 25, the L-CDR2 comprises the amino sequence of SEQ ID NO: 26, and the L-CDR3 comprises the amino sequence of SEQ ID NO: 27; or v) the H-CDR1 comprises the amino sequence of SEQ ID NO: 38, the H-CDR2 comprises the amino sequence of SEQ ID NO: 39, the H-CDR3 comprises the amino sequence of SEQ ID NO: 40, the L-CDR1 comprises the amino sequence of SEQ ID NO: 41, the L-CDR2 comprises the amino sequence of SEQ ID NO: 42, and the L-CDR3 comprises the amino sequence of SEQ ID NO: 43; and wherein the antibody or antigen-binding fragment is an RGMc-selective inhibitor.

2. The antibody or antigen binding fragment of claim 1, wherein the H-CDR1 comprises the amino sequence of SEQ ID NO: 30, the H-CDR2 comprising the amino sequence of SEQ ID NO: 31, the H-CDR3 comprising the amino sequence of SEQ ID NO: 32, the L-CDR1 comprises the amino sequence of SEQ ID NO: 33, the L-CDR2 comprises the amino sequence of SEQ ID NO: 34, and the L-CDR3 comprises the amino sequence of SEQ ID NO: 35.

3. The antibody or antigen-binding fragment of claim 1, comprising a heavy chain variable region comprising an amino acid sequence that is at least 90% identical to SEQ ID NO: 36 and a light chain variable region comprising an amino acid sequence that is at least 90% identical to SEQ ID NO: 37.

4. The antibody or antigen-binding fragment of claim 3, wherein the heavy chain variable region comprises the amino acid sequence of SEQ ID NO: 36 and the light chain variable region comprises the amino acid sequence of SEQ ID NO: 37.

5. The antibody of claim 1, wherein the antibody is a fully human antibody or a humanized antibody.

6. The antibody of claim 1, wherein the antibody is a human IgG1 antibody, a human IgG2 antibody, or a human IgG4 antibody.

7. The antibody of claim 6, wherein the human IgG4 antibody comprises a backbone substitution of Ser to Pro that produces an IgG1-like hinge.

8. The antibody or antigen-binding fragment of claim 1, wherein the antibody binds an epitope within human RGMc, wherein the epitope comprises at least one of the amino acid residues of YVSSTLSL (SEQ ID NO: 46) and at least one amino acid residue of FHSAVHGIEDL (SEQ ID NO: 47).

9. The antibody or antigen-binding fragment of claim 1, wherein the antibody or antigen-binding fragment inhibits or reduces RGMc interaction with BMP6.

10. The antibody or antigen-binding fragment of claim 1, wherein the antibody binds to RGMc to form an antibody-antigen complex, and wherein the antibody induces internalization of the antibody-antigen complex.

11. The antibody or antigen-binding fragment of claim 1, wherein the antibody or antigen-binding fragment binds to RGMc with a $K_D$ value of less than 0.1 nM as determined by Biolayer Interferometry (BLI), surface plasmon resonance (SPR), or solution equilibrium titration-based assay.

12. A pharmaceutical composition comprising the antibody or antigen-binding fragment of claim 1 and a pharmaceutically acceptable carrier.

13. A method for increasing serum iron levels in a subject, the method comprising administering to the subject the pharmaceutical composition of claim 12 in an amount effective to:

i) increase serum iron levels in the subject;

ii) downregulate hepcidin in the subject;

iii) reduce liver hepcidin mRNA levels in the subject;

iv) reduce liver hepcidin protein levels, serum (circulating) hepcidin protein levels, or both in the subject;

v) increase transferrin saturation in the subject;

vi) increase erythropoiesis in the subject;

vii) decrease unsaturated iron binding capacity in the subject;

viii) decrease total iron binding capacity in the subject; and/or, ix) increase serum ferritin levels in the subject.

14. The method of claim 13, wherein the subject has received an erythropoietin (EPO/ESA) therapy, a hypoxia-inducible factor (HIF) stabilizer therapy, an intravenous (IV) iron supplementation, or a combination thereof.

15. The method of claim 14, wherein the subject has manifested or is at risk of an adverse event associated with the EPO therapy, the HIF stabilizer therapy, or the IV iron supplementation.

16. A method of treating an iron disorder in a subject, comprising administering the pharmaceutical composition of claim 12 to the subject in an amount effective to treat the iron disorder in the subject.

17. The method of claim 16, wherein the iron disorder is anemia.

18. The method of claim 17, wherein the anemia is iron-refractory iron-deficiency anemia (IRIDA), anemia of chronic disease (ACD), iron deficiency anemia, cancer-related anemia, chemotherapy-related anemia, anemia of critical illness, or microcytic anemia.

19. The method of claim 18, wherein the anemia of chronic disease (ACD) is associated with chronic bacterial endocarditis, osteomyelitis, rheumatic fever, ulcerative colitis, chronic kidney disease (CKD), or a neoplastic disorder.

20. The method of claim 19, wherein the ACD is associated with CKD, and wherein the subject is dialysis-dependent.

21. The method of claim 19, wherein the ACD is associated with CKD, and wherein the subject is non-dialysis-dependent.

22. The method of claim 16, wherein the iron disorder is a condition involving a functional iron deficiency.

23. The method of claim 16, wherein the subject has cancer.

24. The method of claim 23, wherein the cancer is a myeloproliferative disorder.

25. The method of claim 24, wherein the myeloproliferative disorder is myelofibrosis.

26. The method of claim 23, wherein the subject has received or is receiving a Janus kinase (JAK) inhibitor.

27. The method of claim 26, wherein the JAK inhibitor is a JAK1 inhibitor and/or a JAK2 inhibitor.

28. The method of claim 16, wherein the subject has received or is receiving chemotherapy.

29. The method of claim 16, wherein the subject has or is at risk of having: fatigue, joint pain, bone or joint disease, rheumatoid arthritis, inflammatory bowel disease, shortness of breath, irregular heartbeat, liver trouble, diabetes, infertility, impotence, depression, mood or mental disorders, poor cognitive skills or neurodegenerative diseases, iron-refractory iron-deficiency anemia, anemia of chronic kidney disease, resistance to erythropoiesis-stimulating agents, aplastic anemia, hypoplastic anemias, paroxysmal nocturnal hemoglobinuria, von Willebrand disease, hemophilia hereditary hemorrhagic telangiectasia, a cardiovascular disease, heart failure, restless leg syndrome, absolute iron deficiency, an inflammatory disease, an infectious disease, a neurological disease, and/or a cardiovascular disease.

30. The method of claim 16, wherein the pharmaceutical composition is administered in conjunction with an additional therapeutic agent.

31. The method of claim 30, wherein the additional therapeutic agent is an erythropoietin stimulating agent (ESA), a HIF stabilizer, an iron supplement, and/or a transfusion.

32. The method of claim 31, wherein the method reduces one or more toxicities associated with the ESA, the HIF stabilizer, the iron supplement, or the transfusion.

33. The method of claim 32, wherein the toxicities include iron overload and/or a risk of cancer.

34. The method of claim 16, wherein the amount is an amount effective to achieve a serum ferritin level of 20 nanograms per milliliter of blood.

35. The method of claim 16, wherein the subject:
a) is currently on an iron therapy and benefits from reducing the dosing of the iron therapy;
b) has previously received an iron therapy and discontinued the iron therapy due to one or more toxicities;
c) has previously received an iron therapy and benefits from reducing dosing of the iron therapy;
d) is at risk of cancer; and/or
e) has been diagnosed with cancer.

* * * * *

UNITED STATES PATENT AND TRADEMARK OFFICE
CERTIFICATE OF CORRECTION

PATENT NO. : 12,297,262 B2  
APPLICATION NO. : 17/285952  
DATED : May 13, 2025  
INVENTOR(S) : Samantha Nicholls et al.

Page 1 of 1

It is certified that error appears in the above-identified patent and that said Letters Patent is hereby corrected as shown below:

In the Claims

In Claim 34, Column 140, Lines 7-8, "ferritin level of 20 nanograms" should read --ferritin level of ≥20 nanograms--.

Signed and Sealed this  
Fifteenth Day of July, 2025

Coke Morgan Stewart  
*Acting Director of the United States Patent and Trademark Office*